(12) United States Patent
Lockett et al.

(10) Patent No.: US 9,397,341 B2
(45) Date of Patent: *Jul. 19, 2016

(54) PRINTED ENERGY STORAGE DEVICE

(71) Applicant: NthDegree Technologies Worldwide Inc., Tempe, AZ (US)

(72) Inventors: Vera N. Lockett, Phoenix, AZ (US); Leila Daneshi, Phoenix, AZ (US); William J. Ray, Fountain Hills, AZ (US); John G. Gustafson, Chandler, AZ (US)

(73) Assignee: NthDegree Technologies Worldwide Inc., Tempe, AZ (US)

( * ) Notice: Subject to any disclaimer, the term of this patent is extended or adjusted under 35 U.S.C. 154(b) by 48 days.

This patent is subject to a terminal disclaimer.

(21) Appl. No.: 14/249,316

(22) Filed: Apr. 9, 2014

(65) Prior Publication Data

US 2014/0302373 A1 Oct. 9, 2014

Related U.S. Application Data

(63) Continuation-in-part of application No. 14/050,145, filed on Oct. 9, 2013, and a continuation-in-part of application No. PCT/US2013/064309, filed on Oct. 10, 2013.

(60) Provisional application No. 61/712,219, filed on Oct. 10, 2012.

(51) Int. Cl.
*H01M 4/62* (2006.01)
*C07D 233/58* (2006.01)
(Continued)

(52) U.S. Cl.
CPC .............. *H01M 4/625* (2013.01); *C07D 233/58* (2013.01); *H01M 2/1653* (2013.01); *H01M 4/06* (2013.01);
(Continued)

(58) Field of Classification Search
CPC .................................................. H01M 10/0569
See application file for complete search history.

(56) References Cited

U.S. PATENT DOCUMENTS

| 6,379,835 B1 | 4/2002 | Kucherovsky et al. |
| 6,728,096 B1 | 4/2004 | Smith et al. |

(Continued)

FOREIGN PATENT DOCUMENTS

| JP | 2000-003713 | 1/2000 |
| JP | 2001-176554 | 6/2001 |

(Continued)

OTHER PUBLICATIONS

U.S. Appl. No. 14/050,145, filed Oct. 9, 2013, Printed Energy Storage Device.

(Continued)

*Primary Examiner* — Jane Rhee
(74) *Attorney, Agent, or Firm* — Knobbe, Martens, Olson and Bear, LLP

(57) ABSTRACT

An energy storage device includes a printed current collector layer, where the printed current collector layer includes nickel flakes and a current collector conductive carbon additive. The energy storage device includes a printed electrode layer printed over the current collector layer, where the printed electrode layer includes an ionic liquid and an electrode conductive carbon additive. The ionic liquid can include 1-ethyl-3-methylimidazolium tetrafluoroborate ($C_2mimBF_4$). The current collector conductive carbon can include graphene and the electrode conductive carbon additive can include graphite, graphene, and/or carbon nanotubes.

22 Claims, 21 Drawing Sheets

(51) Int. Cl.

| | |
|---|---|
| *H01M 6/40* | (2006.01) |
| *H01M 2/16* | (2006.01) |
| *H01M 4/06* | (2006.01) |
| *H01M 4/12* | (2006.01) |
| *H01M 4/42* | (2006.01) |
| *H01M 4/50* | (2010.01) |
| *H01M 4/66* | (2006.01) |
| *H01M 6/16* | (2006.01) |
| *H01M 10/0569* | (2010.01) |

(52) U.S. Cl.
CPC *H01M 4/12* (2013.01); *H01M 4/42* (2013.01); *H01M 4/50* (2013.01); *H01M 4/661* (2013.01); *H01M 4/663* (2013.01); *H01M 4/666* (2013.01); *H01M 4/668* (2013.01); *H01M 6/166* (2013.01); *H01M 6/40* (2013.01); *H01M 10/0569* (2013.01)

(56) References Cited

U.S. PATENT DOCUMENTS

| | | | |
|---|---|---|---|
| 7,348,096 | B2 | 3/2008 | Schubert et al. |
| 7,727,290 | B2 | 6/2010 | Zhang et al. |
| 8,029,927 | B2 | 10/2011 | Tucholski |
| 8,119,278 | B2 | 2/2012 | Bailey et al. |
| 2003/0099884 | A1 | 5/2003 | Chiang et al. |
| 2003/0113624 | A1 | 6/2003 | Kim et al. |
| 2008/0020284 | A1 | 1/2008 | Michot et al. |
| 2010/0000441 | A1 | 1/2010 | Jang et al. |
| 2011/0058309 | A1 | 3/2011 | Eguchi et al. |
| 2011/0068296 | A1 | 3/2011 | Huang et al. |
| 2012/0161195 | A1 | 6/2012 | Lowenthal et al. |
| 2013/0280579 | A1 | 10/2013 | Wright et al. |
| 2014/0002788 | A1 | 1/2014 | Otts et al. |
| 2014/0014403 | A1 | 1/2014 | Miller et al. |
| 2014/0017571 | A1 | 1/2014 | Lockett et al. |
| 2014/0099528 | A1 | 4/2014 | Lockett et al. |

FOREIGN PATENT DOCUMENTS

| | | |
|---|---|---|
| JP | 2012-033366 | 2/2012 |
| WO | WO 2007/116649 | 10/2007 |
| WO | WO 2012/037171 | 3/2012 |
| WO | WO 2014/014758 | 1/2014 |
| WO | WO 2014/059127 | 4/2014 |

OTHER PUBLICATIONS

Ho, C. C. et al.., "Direct Write Dispenser Printing of a Zinc Microbattery with an Ionic Liquid Gel Electrolyte," J. Micromech. Microeng., 2010, vol. 20 104009, pp. 1-9.

Forsyth et al., "Ionic Liquids-An Overview," Aust. J. Chem., vol. 57, No. 2, Jan. 1, 2004, pp. 113-119.

International Search Report and Written Opinion in PCT Application No. PCT/US2013/064309, mailed on Jan. 24, 2014, in 13 pages.

HO, C. C. et al., "Direct Write Dispenser Printing of a Zinc Microbattery with an Ionic Liquid Gel Electrolyte," J. Micromech. Microeng., 2010, vol. 20 104009, pp. 1-9.

Huang, Lu et al., "Graphene-Based Conducting Inks for Direct Inkjet Printing of Flexible Conductive Patterns and Their Applications in Electric Circuits and Chemical Sensors," Nano Research, 2011, vol. 4, Issue 7, pp. 675-684.

Torrisi, F. et al., "Ink-Jet Printed Graphene Electronics," Condensed Matter, 2011, pp. 1-12.

PRINTED ENERGY STORAGE DEVICE

CROSS-REFERENCE TO RELATED APPLICATIONS

This application is a continuation-in-part of U.S. patent application Ser. No. 14/050,145, filed Oct. 9, 2013, entitled "PRINTED ENERGY STORAGE DEVICE," and continuation-in-part of PCT Patent Application No. PCT/US2013/064309, filed Oct. 10, 2013, entitled "PRINTED ENERGY STORAGE DEVICE," both of which claim priority benefit of U.S. Provisional Patent Application Ser. No. 61/712,219, filed Oct. 10, 2012, entitled "PRINTED ENERGY STORAGE DEVICE." Each of these applications is incorporated herein by reference in its entirety.

BACKGROUND

1. Field

This invention relates to energy storage devices, particularly to printed energy storage devices.

2. Description of the Related Art

Thin and flexible energy storage devices are needed for powering thin and/or small electronic devices in the consumer market. For example, lights and sound in greeting cards, thin advertisement tools like magazine inserts, skin care products, safe pass cards, some miniature medical devices, etc. can be powered by using thin batteries. Some thin batteries already exist on the market (e.g., zinc carbon batteries produced by Enfucell Oy Ltd. of Vantaa, Finland and Blue Spark Technologies, Inc. of Westlake, Ohio, and lithium polymer batteries produced by Solicore, Inc. of Lakeland, Fla.). These batteries generally have a thickness from about 0.45-0.7 mm. They are sealed in a pouch unit cells with two poles for wired connection to devices which need power.

Zinc-manganese dioxide ($Zn/MnO_2$) batteries are primary batteries (e.g., one time use). These batteries can be filled with an aqueous solution of zinc and ammonia salts or potassium hydroxide. They have an initial voltage of 1.5-1.6V and are designed for low or moderate current drain. Shelf life of these batteries is 1-3 years. Main advantages of $Zn/MnO_2$ batteries are cost and safety. They are the most affordable batteries on the market due to cheap and abundant raw materials for the battery build. These materials are considered "green" due to non-toxicity.

SUMMARY

A printed energy storage device, for example a printed zinc manganese-dioxide ($Zn/MnO_2$) battery, may have a layer that includes an ionic liquid, where the ionic liquid has a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium. The ionic liquid may include an anion selected from the group consisting of tetrafluoroborate, tris(pentafluoroethyl) trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate. The printed energy storage device may have a first electrode, a second electrode and a separator positioned between the first electrode and the second electrode, where at least one of the first electrode, the second electrode and the separator includes the ionic liquid. In some embodiments, the ionic liquid includes 1-ethyl-3-methylimidazolium tetrafluoroborate ($C_2mimBF_4$).

In some embodiments, the first electrode can include the ionic liquid. In some embodiments, the second electrode can include the ionic liquid. In some embodiments, the separator can include the ionic liquid.

The printed energy storage device may include an intermediate layer. The intermediate layer may be between the first electrode and the separator. The intermediate layer may be between the second electrode and the separator. In some embodiments, the intermediate layer includes the ionic liquid.

The printed energy storage device may include a current collector coupled to the first electrode or the second electrode.

In some embodiments, at least one of the first electrode, the second electrode, the separator, the intermediate layer, and the current collector includes a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the intermediate layer, and the separator includes a salt. The salt may include a zinc salt. In some embodiments, the anion of the ionic liquid is the same as an anion of the salt. The salt may include zinc tetrafluoroborate and the ionic liquid may include 1-ethyl-3-methylimidazolium tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, at least one of the first electrode and the second electrode includes polyvinylidene difluoride.

In some embodiments, at least one of the second electrode and the current collector can include carbon nanotubes. The carbon nanotubes may include single-wall carbon nanotubes. The carbon nanotubes may include multi-wall carbon nanotubes.

The second electrode may have a homogeneous paste comprising the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes. The current collector may have graphene flakes. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder. In some embodiments, the current collector can have polyvinylidene difluoride.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns. In some embodiments, the separator can include polyvinylidene difluoride.

A layer of a printed energy storage device, for example a printed zinc manganese-dioxide ($Zn/MnO_2$) battery, may include a salt having an anion, and an ionic liquid including the anion.

In some embodiments, the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium.

In some embodiments, the anion can be selected from the group consisting of tetrafluoroborate, tris(pentafluoroethyl) trifluorophosphate, trifluoromethanesulfonate, hexafluorophosphate, ethyl sulfate, dimethyl phosphate, methansulfonate, triflate, tricyanomethanide, dibutylphosphate, bis (trifluoromethylsulfonyl)imide, bis-2,4,4-(trimethylpentyl) phosphinate, iodide, chloride, bromide, and nitrate.

In some embodiments, the ionic liquid can include 1-ethyl-3-methylimidazolium tetrafluoroborate ($C_2mimBF_4$). In some embodiments, the salt can include a zinc salt. The salt may include zinc tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

The printed energy storage device may have a first electrode, a second electrode, and a separator between the first electrode and the second electrode. In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

The layer may be the first electrode, the separator, and/or the intermediate layer.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can have polyvinylidene difluoride.

In some embodiments, at least one of the second electrode and the current collector can have carbon nanotubes. The carbon nanotubes may include single-wall carbon nanotubes. The carbon nanotubes may include multi-wall carbon nanotubes.

The second electrode may have a mixture including the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes. The current collector may have graphene flakes. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A layer of a printed energy storage device, for example a printed zinc manganese-dioxide ($Zn/MnO_2$) battery, may have a salt including zinc tetrafluoroborate, and an ionic liquid having 1-ethyl-3-methylimidazolium tetrafluoroborate.

The printed energy storage device may include a first electrode, a second electrode, and a separator between the first electrode and the second electrode. In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

The layer may be the first electrode, the separator, and/or the intermediate layer.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can have polyvinylidene difluoride.

In some embodiments, at least one of the second electrode and the current collector can have carbon nanotubes. The carbon nanotubes may include single-wall carbon nanotubes. The carbon nanotubes may include multi-wall carbon nanotubes.

The second electrode may have a mixture including the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes. The current collector may have graphene flakes. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A planarization adhesion layer of a printed energy storage device, for example a printed zinc manganese-dioxide (Zn/$MnO_2$) battery, can include polyvinyl alcohol, a salt, an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and where the ionic liquid can include an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

In some embodiments, the salt can include an anion that is the same as the anion of the ionic liquid. In some embodiments, the salt can include a zinc salt. The salt may include zinc tetrafluoroborate and the ionic liquid can include 1-ethyl-3-methylimidazolium tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

The printed energy storage device may have a first electrode, a second electrode, and a separator between the first electrode and the second electrode.

The planarization adhesion layer may be between the first electrode and the separator. The planarization adhesion layer may be between the second electrode and the separator. In some embodiments, the printed energy storage device can include a current collector electrically coupled to the first electrode or the second electrode. In some embodiments, the printed energy storage device can include a current collector electrically coupled to the first electrode or the second electrode.

In some embodiments, at least one of the first electrode, the second electrode, the separator, the planarization adhesion layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can have polyvinylidene difluoride.

In some embodiments, at least one of the second electrode and the current collector can have carbon nanotubes. The carbon nanotubes may include single-wall carbon nanotubes. The carbon nanotubes may include multi-wall carbon nanotubes.

The second electrode may have a mixture including the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes, for example a current collector electrically coupled to the first electrode. The current collector may have graphene flakes, for example a current collector electrically coupled to the second electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, at least one of the first electrode, separator, and second electrode can include the ionic liquid.

An electrode of a printed energy storage device, for example a printed zinc manganese-dioxide ($Zn/MnO_2$) battery, can include carbon nanotubes, and an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and where the ionic liquid can include an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

The carbon nanotubes may include single-wall carbon nanotubes. The carbon nanotubes may include multi-wall carbon nanotubes. The carbon nanotubes may be ground. In some embodiments, the carbon nanotubes and the ionic liquid can form a homogeneous mixture.

In some embodiments, the ionic liquid can include 1-ethyl-3-methylimidazolium tetrafluoroborate.

In some embodiments, the electrode can include manganese dioxide. In some embodiments, the electrode can include graphite powder.

The printed energy storage device may further include a second electrode and a separator between the electrode and the second electrode.

In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

In some embodiments, at least one of the second electrode, the separator, and the intermediate layer can include the ionic liquid. In some embodiments, at least one of the second electrode, the separator, and the intermediate layer can include a salt. The salt may include an anion that is the same as an anion of the ionic liquid.

In some embodiments, the salt can include a zinc salt. In some embodiments, the ionic liquid can include 1-ethyl-3-methylimidazolium tetrafluoroborate ($C_2mimBF_4$) and the salt can include zinc tetrafluorborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the electrode, the second electrode, the separator, and the current collector can include polyvinylidene difluoride.

In some embodiments, the current collector can have at least one of nickel flakes, graphene flakes, and graphite powder. The current collector may have nickel flakes, for example a current collector coupled to the second electrode. The current collector may have graphene flakes, for example a current collector coupled to the first electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A printed energy storage device, for example a printed zinc manganese-dioxide ($Zn/MnO_2$) battery, can include a first electrode having zinc, a second electrode having manganese dioxide, a separator between the first electrode and the second electrode, and a current collector electrically connected to the first electrode or the second electrode, the current collector including conductive flakes.

In some embodiments, the current collector can include carbon nanotubes. The carbon nanotubes may include single-wall carbon nanotubes. The carbon nanotubes may include multi-wall carbon nanotubes.

In some embodiments, the conductive flakes can include at least one of nickel flakes, graphene flakes, and graphite powder. The current collector may have nickel flakes, for example a current collector electrically coupled to the first electrode. The current collector may have graphene flakes, for example a current collector electrically coupled to the second electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the printed energy storage device can include an intermediate layer. The intermediate layer may be between the first electrode and the separator. The intermediate layer is between the second electrode and the separator.

In some embodiments, at least one of the first electrode, the second electrode, the separator and the intermediate layer can include an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, where the ionic liquid can include an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

In some embodiments, the ionic liquid can include 1-ethyl-3-methylimidazolium tetrafluoroborate ($C_2mimBF_4$).

In some embodiments, at least one of the first electrode, the separator, and the intermediate layer can include a salt. The salt may include an anion that is the same as the anion of the ionic liquid. In some embodiments, the salt can include zinc tetrafluoroborate and the ionic liquid can include 1-ethyl-3-methylimidazolium tetrafluoroborate.

In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, the first electrode can include polyvinylidene difluoride.

In some embodiments, at least one of the first electrode, the second electrode, the separator, the intermediate layer, and the current collector can include a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, the second electrode can include the carbon nanotubes. In some embodiments, the second electrode can include a homogeneous paste including the carbon nanotubes and the ionic liquid. In some embodiments, the second electrode can include a conductive carbon. The conductive carbon can include graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A conductive paste for a layer of a printed energy storage device, for example a printed zinc manganese-dioxide (Zn/MnO$_2$) battery, can include carbon nanotubes, and an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and where the ionic liquid can include an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

In some embodiments, the ionic liquid can include 1-ethyl-3-methylimidazolium tetrafluoroborate (C$_2$mimBF$_4$).

The carbon nanotubes may include single-wall carbon nanotubes. The carbon nanotubes may include multi-wall carbon nanotubes. The carbon nanotubes may be ground. In some embodiments, the carbon nanotubes and the ionic liquid can form a homogeneous mixture.

In some embodiments, the layer can be a first electrode. The first electrode can include manganese dioxide. In some embodiments, the first electrode can include graphite.

In some embodiments, a printed energy storage device can include a second electrode and a separator between the first electrode and the second electrode.

In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

In some embodiments, at least one of the second electrode, the separator, and the intermediate layer can include the ionic liquid. In some embodiments, at least one of the second electrode, the separator, and the intermediate layer can include a salt. In some embodiments, the salt can include a zinc salt. In some embodiments, the salt can include an anion that is the same as the anion of the ionic liquid. The salt may include zinc tetrafluoroborate and the ionic liquid can include 1-ethyl-3-methylimidazolium tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can include polyvinylidene difluoride.

In some embodiments, the current collector can include the carbon nanotubes.

In some embodiments, the current collector can have at least one of nickel flakes, graphene flakes, and graphite powder. The current collector may have nickel flakes, for example a current collector electrically coupled to the second electrode. The current collector may have graphene flakes, for example a current collector electrically coupled to the first electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

An energy storage device can include a printed collector layer, where the printed current collector layer can include nickel flakes and a current collector conductive carbon additive. The energy storage device can include a printed electrode layer printed over the current collector layer, where the printed electrode layer can include an ionic liquid and an electrode conductive carbon additive. The ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-1-propylpiperidinium, 1-butyl-2-methylpyridinium, 1-butyl-4-methylpyridinium, and 1-butyl-1-methylpyrrolidinium. The ionic liquid can include an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

In some embodiments, the printed electrode layer can include a printed anode electrode layer and the energy storage device can include a zinc manganese dioxide battery.

In some embodiments, the current collector conductive carbon additive can include graphene. In some embodiments, the electrode conductive carbon additive can include at least one of graphite, graphene, and carbon nanotubes. In some embodiments, the carbon nanotubes can include multi-wall carbon nanotubes.

In some embodiments, the printed current collector layer can include a polyester component formed in-situ from a polycarboxylic component and a polyol component. The polycarboxylic component can include glutaric acid and the polyol component can include ethylene glycol.

In some embodiments, the energy storage device can have an electrolyte including the ionic liquid. In some embodiments, the electrolyte can include zinc tetrafluoroborate.

A method of fabricating an energy storage device can include printing a current collector layer over a substrate, where the current collector layer can include nickel flakes and a current collector conductive carbon additive. The method can include printing an electrode layer over the current collector layer, where the electrode layer can include an ionic liquid and an electrode conductive carbon additive. The ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-1-propylpiperidinium, 1-butyl-2-methylpyridinium, 1-butyl-4-methylpyridinium, and 1-butyl-1-methylpyrrolidinium. The ionic liquid can include an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

In some embodiments, the energy storage device can include a zinc manganese dioxide battery.

In some embodiments, printing the current collector layer can include mixing the nickel flakes and the current collector conductive carbon additive with a polycarboxylic acid and a polyol. In some embodiments, mixing can include forming a polyester in-situ from the polycarboxylic acid and the polyol.

In some embodiments, the method can include providing a separator adjacent the electrode layer, where the separator can include at least one of polypropylene, polyethylene, polytetrafluoroethylene, cellulose, and aramid. The separator can be a non-printed separator.

In some embodiments, the current collector conductive carbon additive can include graphene. In some embodiments, the electrode conductive carbon additive can include at least one of graphite, graphene, and carbon nanotubes.

In some embodiments, the ionic liquid can include 1-ethyl-3-methylimidazolium tetrafluoroborate ($C_2mimBF_4$).

In some embodiments, printing the electrode layer can include printing the electrode layer with the electrode conductive carbon additive at a concentration of about 0.5 weight % to about 5 weight %.

In some embodiments, the electrode layer can include an anode electrode layer.

In some embodiments, printing the electrode layer can include printing the electrode layer with the electrode conductive carbon additive at a concentration of about 1.5 weight % to about 24 weight %.

In some embodiments, the electrode layer can include a cathode electrode layer.

For purposes of summarizing the invention and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the invention.

DETAILED DESCRIPTION

Figure 1:
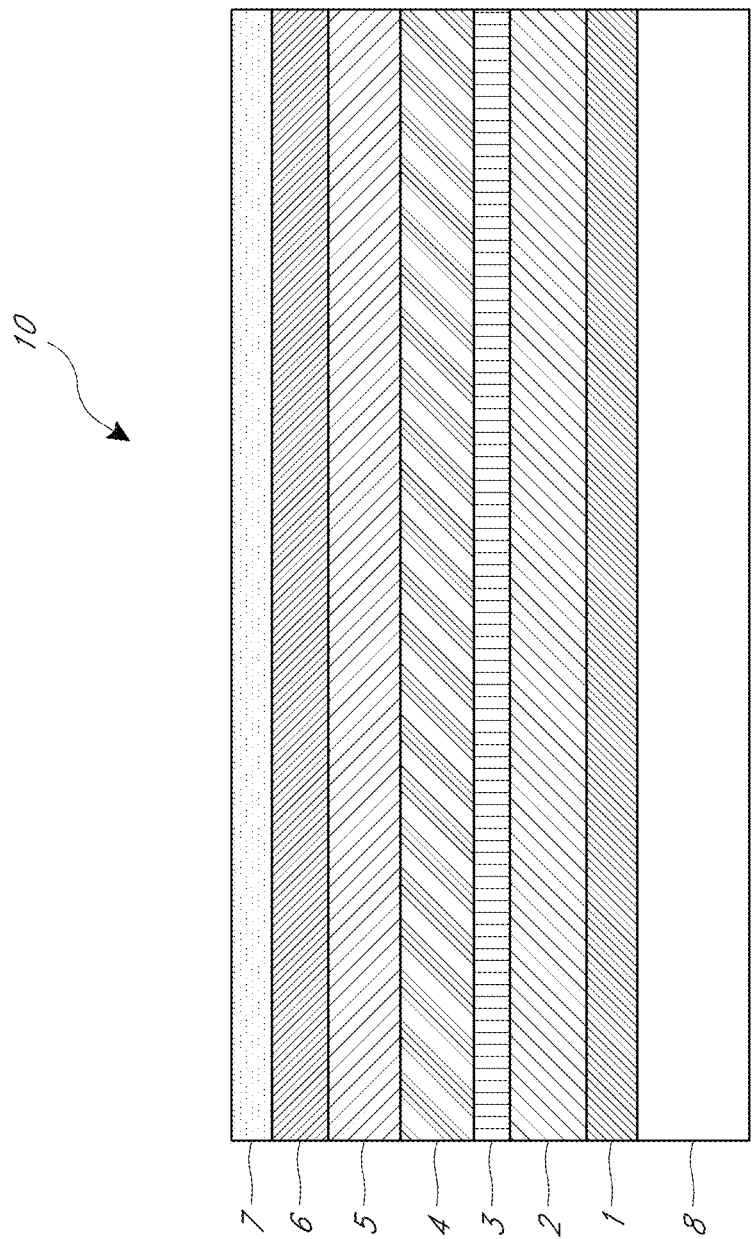
FIG. 1 is a cross-sectional or side elevational view of an example embodiment of a printed battery.

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

In some embodiments, a zinc-manganese dioxide (Zn/MnO$_2$) battery comprises all elements of which are printed. For example, all components of the battery, including current collectors, electrodes, battery separator, and leads may be sequentially printed onto one substrate. Printing can be a scalable, cost effective, and productive technique. For example, a battery having all components which are printed may facilitate a simplified manufacturing process, and/or facilitate fabrication of a battery having a desired form-factor with reduced costs. In some embodiments, a printed Zn/MnO$_2$ battery separator can include a solid state electrolyte. In some embodiments, a printed a Zn/MnO$_2$ battery includes a printed electrolyte, for example an electrolyte printed onto a previously printed battery separator for providing a printed battery having a liquid electrolyte. For example, all components of the battery, including the electrolyte, can be sequentially printed onto a substrate.

In some embodiments, printed Zn/MnO$_2$ batteries can have a thickness from about 0.1 mm to about 0.4 mm and can be flexible depending on the substrate that at least some of the battery layers are printed on. Printed zinc-manganese dioxide batteries can be used as a separate device or integrated on a substrate with other electronic components, such as light-emitting diode (LED) lights. Devices into which printed zinc-manganese dioxide batteries may be integrated devices can be thin and/or flexible. An integrated printed zinc-manganese dioxide battery may not need additional connection elements like wires for electrical connection with other electronics as all necessary connections may also be printed.

A fully printed battery can enable fabrication of batteries having a variety of shapes. In some embodiments, a printed battery can be printed around other components of an integrated device and/or printed on a substrate with an unusual shape. For example, the printed battery may be printed on commercially available substrates (e.g., polyimide film such as Kapton® from DuPont, Inc. of Wilmington, Del.) or manufactured. In some embodiments, one printed battery can be printed above one or more other energy storage devices, including, for example, one or more other printed batteries. For example, the printed battery can be connected with one or more other printed batteries in parallel to enable an increased energy storage capacity per unit of area and/or in series to enable an increased working voltage. Suitable zinc (Zn) for a printed battery may be commercially available (e.g., from Teck American Inc., of Spokane, Wash.) or manufactured. Suitable manganese dioxide (MnO$_2$) may be commercially available (e.g., from Minera Autlan, of Mexico) or manufactured.

In some embodiments, a printed Zn/MnO$_2$ battery has an open circuit potential from about 1.5 volts (V) to about 1.55V and a capacitance of about 0.1 mAh/cm$^2$ when discharged at about 0.1 mA/cm$^2$. For example, three 1×1.5 inch printed zinc-manganese dioxide batteries connected in series printed on a substrate with 30 blue micro-light-emitting-diodes (microLEDs) can light the microLEDs non-stop for 1.5 hours. In some embodiments, printed batteries can be integrated into thin and/or small consumer electronic devices for powering the devices. For example, printed batteries can power lights and/or audio modules of greeting and/or business cards, thin advertisement tools like magazine inserts, skin care products, safe pass cards, and medical devices. An on-off switch (e.g., a press-button control) for the LEDs can further extend the operating life of batteries.

In some embodiments, a printed zinc-manganese dioxide includes an electrolyte comprising ionic liquid 1-ethyl-3-methylimidazolium tetrafluoroborate (C$_2$mimBF$_4$). The ionic liquid may be commercially available (e.g., IoLiTec Ionic Liquids Technologies GmbH, of Heilbronn, Germany) or manufactured. In certain embodiments, the electrolyte for Zn/MnO$_2$ batteries may comprise a "green" electrolyte-ionic liquid 1-ethyl-3-methylimidazolium tetrafluoroborate (C$_2$mimBF$_4$). Some existing Zn/MnO$_2$ batteries (comprising zinc carbon and zinc alkaline) have either an aqueous solution of ammonium and zinc chlorides or an aqueous solution of potassium hydroxide as electrolytes. Aqueous electrolytes can evaporate easily, including for example after integration into a battery, and special measures may need to be taken to inhibit or prevent evaporation or leakage. A battery having an aqueous electrolyte may require special care during battery assembly. C$_2$mimBF$_4$ is a non-volatile electrolyte. Non-volatile electrolytes may be suitable for printing processes. For example, an electrolyte may maintain or substantially maintain a concentration during a battery production process and/or in post assembly life of a battery comprising the electrolyte. Ionic liquids are ecological "green" electrolytes in terms that they do not contaminate air. Another attractive property of the ionic liquid used is non-flammability. For example, an ionic liquid electrolyte cannot self-ignite during a battery overload or shortage, and will not support any flame.

FIG. 1 is a cross-sectional or side elevational view of an example embodiment of the a printed battery 10, for example a zinc-manganese dioxide battery. The printed battery 10 includes a first current collector 1, a first electrode layer 2, an intermediate layer 3, a separator layer 4, a second electrode layer 5, a second current collector 6, an insulator layer 7, and a substrate 8. The first current collector 1 is configured provide electrical contact between the first electrode layer 2 and an external circuit. In some embodiments, the printed battery 10 may optionally not include the intermediate layer 3. In some embodiments, the current collector 6 is configured to provide electrical contact between the second electrode layer 5 and an external circuit. In some embodiments, the printed battery 10 may optionally not include the current collector 1, for example in embodiments in which the substrate 8 comprises a material having conductivity allowing connection to an external circuit. In some embodiments, the intermediate layer 3 comprises a plurality of layers. In some embodiments, the printed battery 10 may optionally not include the intermediate layer 3.

In some embodiments, the printed battery 10 can be printed layer by layer. For example, layers 1-7 of the printed zinc manganese dioxide battery 10 may be printed one above the other in the following sequence: the first current collector layer 1 may be printed onto a surface of the substrate 8; the first electrode layer 2 may be printed onto a surface of the first current collector layer 1; the intermediate layer 3 may be printed onto a surface of the first electrode layer 2; the separator layer 4 may be printed onto a surface of the intermediate layer 3, or as described herein onto a surface of the first electrode layer 2; the second electrode layer 5 may be printed onto a surface of the separator layer 4; the second current collector layer 6 may be printed onto a surface of the second electrode layer 5; and the insulator layer 7 may be printed onto a surface of the current collector layer 6. The insulator layer 7 may comprise a polymer and may provide the printed battery 10 with a seal (e.g., a hermetic seal).

Figure 2:
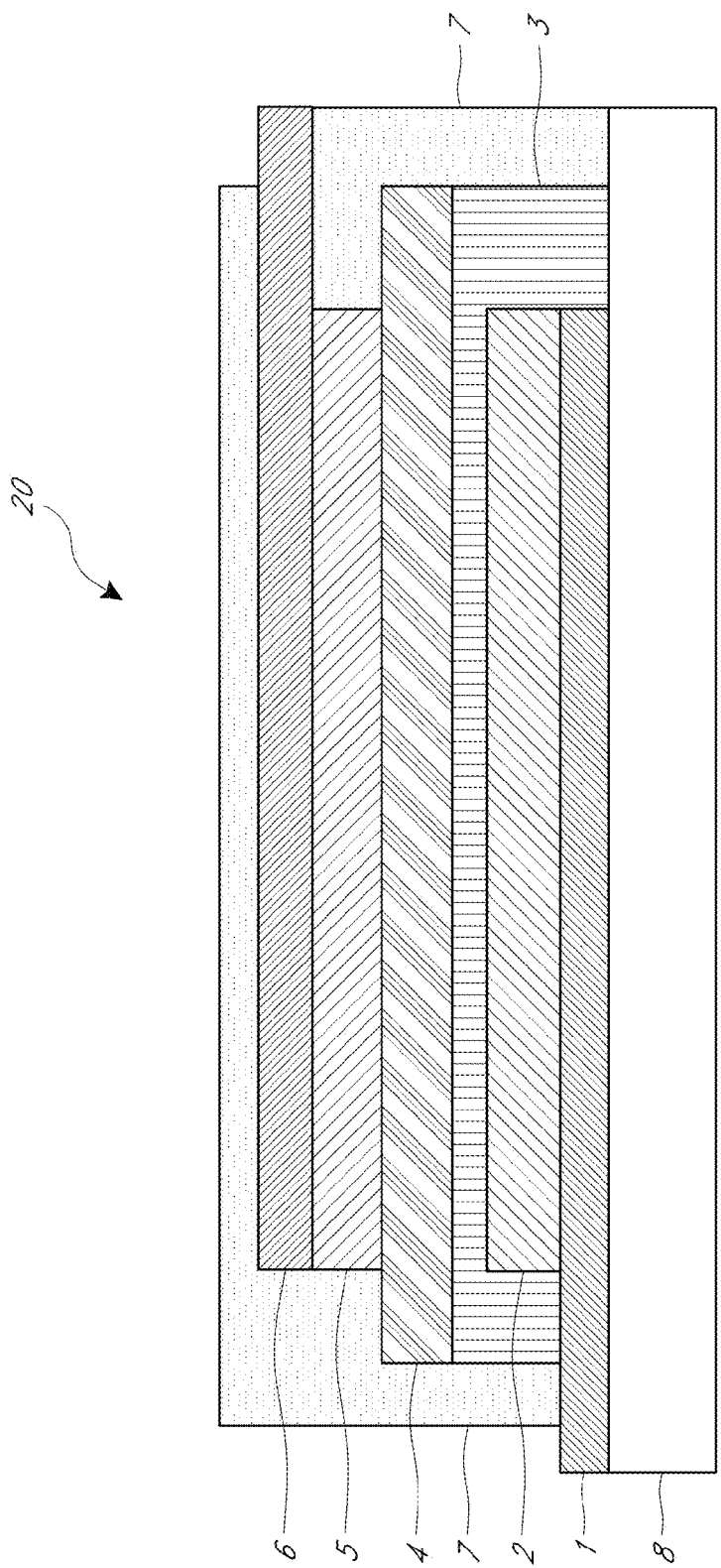
FIG. 2 is a cross-sectional or side elevational view of another example printed battery.

FIG. 2 is a cross-sectional or side elevational view of another example embodiment of a printed battery 20, for example a zinc-manganese dioxide battery comprising the layers 1-8 discussed herein. The current collector layers 1, 6 may extend beyond a portion of electrode layers 2, 5, for example to facilitate coupling with an external circuit. The intermediate layer 3 may form an enclosure over at least a portion of electrode layer 2, for example to facilitate separation between the two electrode layers 2, 5. The polymer insulator layer 7 may form an enclosure around the electrode layers 2, 5, the intermediate layer 3, and the separator layer 4, for example to seal the layers of the printed battery 10 (e.g., with a hermetic seal).

In some embodiments, a zinc anode (e.g., the first electrode layer 2 in FIG. 1) may comprise a polymer binder (e.g., high molecular weight polyvinylidene difluoride polymer), zinc, and/or an electrolyte comprising zinc salt such as zinc tetrafluoroborate ($ZnBF_4$) and $C_2mimBF_4$ ionic liquid. The zinc salt has a common anion with the used ionic liquid and can create an electroactive couple with zinc ($Zn/Zn^{2+}$).

In some embodiments, the separator layer 4 can comprise an electrolyte/polymer gel and microspheres (e.g., micro glass spheres as described in U.S. patent application Ser. No. 13/223,279, entitled "Printable Ionic Gel Separation Layer for Energy Storage Devices," which is herein incorporated by reference in its entirety). For example, a printed zinc manganese-dioxide battery may comprise a separator layer including an electrolyte comprising $ZnBF_4/C_2mimBF_4$, a polymeric gel comprising copolymers of polyvinylidene difluoride, and micro glass spheres. Micro glass spheres may be commercially available (e.g., from Potters Industries, of Brownwood, Tex.) or manufactured. Some commercially available batteries, including flexible batteries, use a separate sheet of membrane as a separator between electrode layers. A separator comprising solid microspheres is that the separator layer 4 may advantageously be printed. For example, the separator layer 4, including solid microspheres may be fabricated through a printing process, along with other components of a printed battery 10, instead of being formed during a separate fabrication process and then being integrated into the battery. Ionic conduction through the separator layer 4 may be realized by the ionic liquid/polymer gel. The polymer gel can be fabricated from polyvinylidene difluoride copolymer. The solid microspheres can enable the separator layer 4 to withstand applied pressure during the printing process, including for example subsequent printing of one or more other layers 5-7 of the printed battery 10 and, therefore, inhibit or prevent shorting of the printed battery 10. A printed battery 10 including a printed separator layer 4 comprising solid microspheres can provide larger or significantly larger charge storage areas than batteries including a non-printed separator, for example because the separator layer 4 can be printed over a large surface area and/or have unique lateral shapes.

A printed battery 10 may optionally comprise the intermediate layer 3. The intermediate layer 3 may be an ultrathin layer (e.g., having a thickness in a range from about 1 micron (μm) to about 3 microns) that coats an underlying layer, for example the first electrode layer 2. The printed battery 10 may include an intermediate layer between other layers described herein, including, for example, between the separator layer 4 and the second electrode layer 5. The intermediate layer 3 can provide a smoother interface between two adjacent printed layers and/or help preserve the structural integrity of one or more underlying layers from damage due to pressure applied during printing of one or more subsequent layers (e.g., during printing of the separator layer 4). The intermediate layer 3 may also promote adhesion between the two adjacent layers, such as between the separator layer 4 and the first electrode layer 2. In some embodiments, the intermediate layer 3 comprises a polymeric gel and an electrolyte for ionic conduction. The electrolyte may comprise an ionic liquid, such as the same ionic liquid as the separator layer 4. The polymeric gel can be made from polyvinyl alcohol (PVA) polymers having different molecular masses. For example, the intermediate layer 3 may include an electrolyte comprising $ZnBF_4/C_2mimBF_4$ and a polymeric gel comprising polyvinyl alcohol. Other polymers and/or electrolytes may also be suitable.

In some embodiments, an electrode layer (e.g., the first electrode layer 2, the second electrode layer 5) can include carbon nanotubes (CNT). For example, a printed zinc manganese-dioxide battery cathode (e.g., the second electrode layer 5 of the printed battery 10) may comprise $MnO_2$, conductive carbon (e.g., graphite), a polymer (e.g., high molecular weight polyvinylidene difluoride polymer) as a binder, an electrolyte (e.g., an ionic liquid), and carbon nanotubes. Suitable graphite may be commercially available (e.g., from TIMCAL Ltd., of Westlake, Ohio) or manufactured. The printed zinc manganese-dioxide battery cathode may comprise a dispersion comprising ground carbon nanotubes and an ionic liquid (e.g., $C_2mimBF_4$). Carbon nanotubes may include single-wall (SWCNT) and/or multi-wall carbon nanotubes (MWCNT). Carbon nanotubes may be commercially available (e.g., from SouthWest NanoTechnologies Inc., of Norman, Okla.) or manufactured. The second electrode layer 5 may include a homogeneous paste comprising an ionic liquid and carbon nanotubes. Incorporation of carbon nanotubes into an electrode may improve electron conductivity within the electrode and/or facilitate incorporation of ionic liquid electrolyte in the electrode.

The composition of the current collector layers 1 and 6 may differ depending on the functions that each is designed to fulfill. The first current collector layer 1, for example configured to be at the bottom of a printed stack and/or to be electrically coupled to an anode, may comprise a mixture of nickel (Ni) flakes and a polymer, and may be printed on the substrate 8 to provide good adherence of the first electrode layer 1 to the substrate 8. Nickel flakes may be commercially available (e.g., from Novamet Specialty Products Corp. of Wyckoff, N.J.) or manufactured. The second current collector layer 6, for example configured to electrically couple to a cathode, may comprise graphene flakes and a polymer, and may be printed over the second electrode layer 5. Graphene flakes may be commercially available (e.g., from XG Sciences, Inc. of Lansing, Mich.) or manufactured. Graphene particles in the second current collector layer 6 are generally light and bendable such that they do not penetrate through the second electrode layer 5 during printing of the second current collector layer 6.

Example combinations of conductive materials for current collectors comprise:
1) Ni flakes
2) Graphene flakes
3) Ni and graphene flakes
4) Ni flakes, graphene and graphite powder
5) Ni flakes, CNTs
6) Ni flakes, graphene, CNTs
7) Ni flakes, graphene, CNTs, graphite powder
8) Ni flakes, CNTs, graphite powder
9) Graphene, CNTs
10) Graphene, CNTs, graphite powder.

A polymer insulator layer 7, such as a hermetic printed layer, may optionally be used to seal the printed battery 10, for example to inhibit or prevent contact between the atmosphere (e.g., water and oxygen) with the materials of the printed battery 10. The insulator layer 7 may comprise, for example, an environmentally robust polymer.

Battery Performance Measurement

Figure 3B:
FIG. 3B is a photographic side view of the printed battery of FIG. 3A.
Figure 3A:
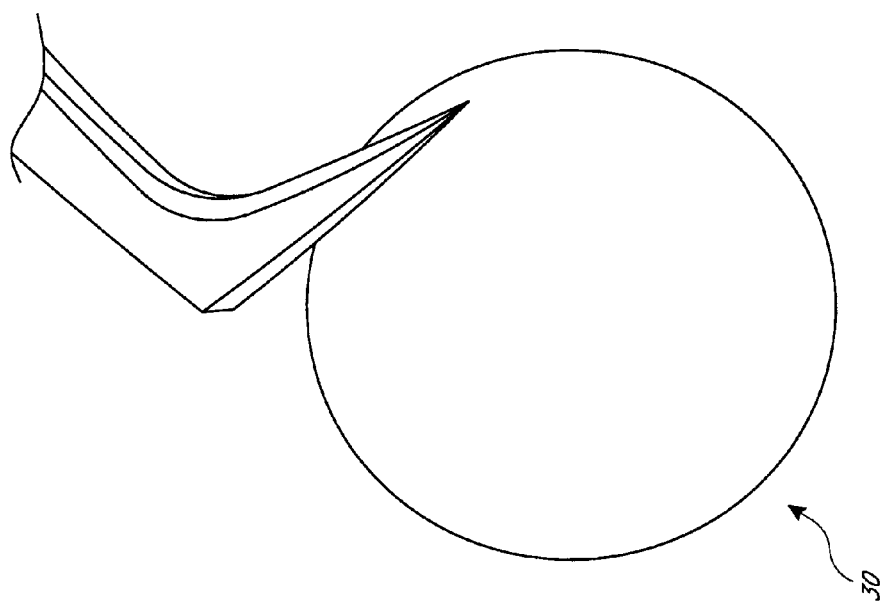
FIG. 3A is a photographic plan view of an example embodiment of a printed battery.

Printed zinc manganese dioxide ($Zn/MnO_2$) batteries may be printed in different designs depending on testing procedure. The batteries discharged in electrochemical cells can be printed on aluminum (Al) foil without current collectors. FIGS. 3A and 3B illustrate an example printed $Zn/MnO_2$ battery on Al foil. FIG. 3A is a photographic plan view of an example embodiment of a printed battery, and FIG. 3B is a photographic side view of the printed battery of FIG. 3A. The electrochemical cell can then connect to a potentiostat.

Figure 4:
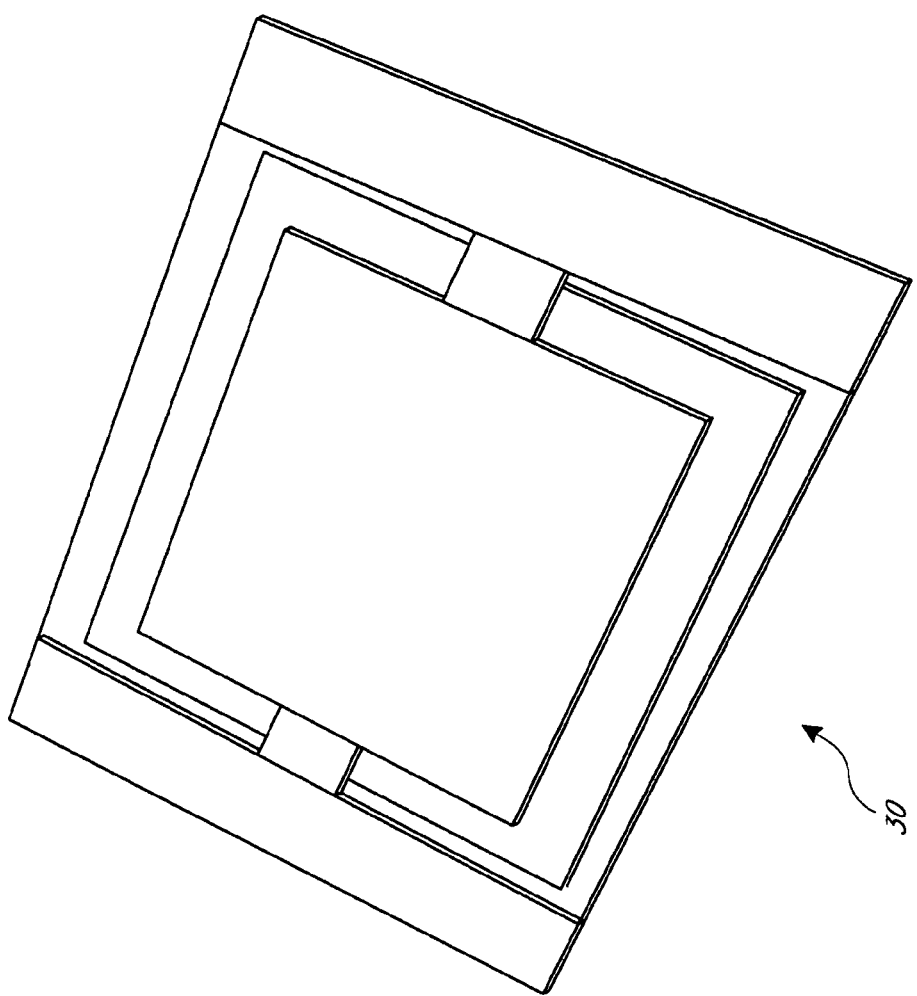
FIG. 4 is a photographic perspective view of another example embodiment of a printed battery.

FIG. 4 is a photographic perspective view of another example of a printed battery 40. The printed battery 40 shown in FIG. 4 is a $Zn/MnO_2$ battery including a polyethylene terephthalate (e.g., Mylar®) substrate and including bus bars for connecting to a potentiostat.

Example Compositions of Printed Battery Layers

An example first electrode layer 2 comprises, by weight:
high molecular weight polyvinylidene difluoride polymer (PVDF, e.g., KYNAR® HSV 900 from Arkema, Inc. of King of Prussia, Pa.)—0.6%
Zn powder (particle size below 10 microns)—99.31%
1 mol/L (M) $ZnBF_4$ in $C_2mimBF_4$ electrolyte—0.09%
An example intermediate layer 3 comprises, by weight:
PVA 133,000 molecular weight—6.86%
PVA 6,000 molecular weight—35.73%
1 M $ZnBF_4$ in $C_2mimBF_4$ electrolyte—57.41%
An example separator layer 4 comprises, by weight:
PVDF (e.g., KYNAR® ADX 161 from Arkema, Inc., of King of Prussia, Pa.)—3.56%
1 M $ZnBF_4$ in $C_2mimBF_4$ electrolyte—36.96%
Glass spheres (less than 20 microns in diameter)—59.48%
An example second electrode layer 5 comprises, by weight:
high molecular weight PVDF HSV 900—4.89%
MWCNT—0.8%
$C_2mimBF_4$ ionic liquid—4.51%
Graphite powder—2.35%
$MnO_2$—87.05%
An example first current collector layer 1 comprises, by weight:
high molecular weight PVDF HSV 900—5.41%
Ni flakes—94.49%
An example second current collector layer 6 comprises, by weight:
high molecular weight PVDF HSV 900—17.42%
Graphene flakes—82.58%
An example insulator layer 7 comprises, by weight:
high molecular weight PVDF HSV 900—100%

Example Printable Ink Compositions (Examples of Successful Ink Compositions), Preparation Process, Properties, and Curing Conditions An example composition of an ink for a first electrode layer 2 comprises, by weight:
high molecular weight PVDF HSV 900—0.51%
Zn powder (particle size below 10 microns)—85.12%
1-methyl-2-pyrrolidinone (MP) solven—14.29%
1 M $ZnBF_4$ in $C_2mimBF_4$ electrolyte—0.08%

An example procedure to prepare the ink for the first electrode layer 2 includes:
Prepare PVDF HSV 900 base: Heat MP to 60° C. and progressively add PVDF HSV 900. Mix for 30 minutes at 60° C. using a laboratory egg.
Prepare electrolyte: Dissolve $ZnBF_4$ in $C_2mimBF_4$ by mixing at 50° C. in a laboratory egg until the zinc salt is dissolved.
Take PVDF HSV 900 base, electrolyte, and MP and sonicate for 10 minutes.
Take the sonicated mixture, preheat to 40° C., and add additional MP and zinc dust. Stir for 30 minutes using a laboratory egg.

The ink for the first electrode layer 2 fabricated using the example method can have a viscosity of about 10,000 centipoise (cP). An example curing profile for this composition is at a temperature of 130° C. for between 3 and 5 minutes.

An example composition for an ink for an intermediate layer 3 comprises, by weight:
MP solvent—81.19%
PVA 133,000 molecular weight—1.29%
PVA 6,000 molecular weight—6.72%
1 M $ZnBF_4$ in $C_2mimBF_4$ electrolyte—10.8%

An example procedure to prepare the ink for the intermediate layer 3 includes:
Preheat MP to 80° C. Slowly pour PVA 133,000 molecular weight into MP. Mix using magnetic bar.
Add PVA 6,000 molecular weight to the MP solution when the PVA 133,000 is dissolved.
Reduce heat to 60° C. and add $ZnBF_4$ in $C_2mimBF_4$ electrolyte drop wise. Stir using laboratory egg. Cool down the mixture until gelled.

The ink for the intermediate layer 3 fabricated using the example method can have a viscosity of about 100 cP. An example curing profile for this composition is at a temperature of 130° C. for between 5 and 7 minutes.

An example composition of an ink for the separator layer 4 comprises, by weight:
PVDF ADX 161—2.92%
1 M $ZnBF_4$ in $C_2mimBF_4$ electrolyte—30.34%
Glass spheres (less than 20 microns in diameter)—48.82%
MP solvent—17.92%

An example procedure to prepare the ink for the printed separator layer 4 includes:
Prepare PVDF ADX 161 base: Preheat MP to 80° C. Add PVDF ADX 161. Mix until PVDF ADX 161 is dissolved using a laboratory egg.
Preheat PVDF ADX 161 base to 60° C. and add $ZnBF_4$ in $C_2mimBF_4$ electrolyte drop by drop while mixing using a laboratory egg.
Cool down the mixture and add glass spheres. Mix for 10 minutes at room temperature using a laboratory egg.

The ink for the separator layer 4 fabricated using the example method can have a viscosity of about 13,000 cP. An example curing profile for this composition is at a temperature of 130° C. for between 5 and 7 minutes.

An example composition for an ink for a second electrode layer 5 comprises, by weight:
high molecular weight PVDF HSV 900—2.3%
MWCNT—0.38%
$C_2mimBF_4$ ionic liquid—2.13%
MP solvent—52.79%
Graphite powder—1.11%
$MnO_2$—41.1%

An example procedure to prepare the ink for the second electrode layer 5 includes:
Prepare MWCNTs paste in $C_2mimBF_4$: Grind a mixture of 15% of the MWCNTs and 85% of the $C_2mimBF_4$ in a mortar and pestle in glove box for 5 minutes, then grind in automated mortar and pestle for 1 hour.
Prepare PVDF HSV 900 base: Heat MP to 60° C. and progressively add PVDF HSV 900. Mix for 30 minutes at 60° C. using a laboratory egg.
Take PVDF HSV 900 base and mix with MWCNT paste under sonication and at 50° C. for 30 minutes. Add graphite powder and $MnO_2$ and mix at 70° C. for 90 minutes using a laboratory egg.

The ink for the second electrode layer 5 fabricated using the example method can have a viscosity of about 9,000 cP. An example curing profile for this composition is at a temperature of 130° C. for between 3 and 5 minutes.

An example composition for an ink for the first current collector layer 1 comprises, by weight:
PVDF HSV 900—3.63%
Ni flakes—63.47%
MP solvent—32.9%

An example procedure to prepare the ink for the first current collector layer 1 includes:
Prepare PVDF HSV 900 base: Heat MP to 60° C. and progressively add PVDF HSV 900. Mix for 30 minutes at 60° C. using a laboratory egg. Add Ni flakes to the PVDF HSV 900 base while continuing to stir.

An example curing profile for the ink for the first current collector layer 1 fabricated using the example is at a temperature of 130° C. for between 3 and 5 minutes.

An example composition for an ink for the second current collector layer 6 comprises, by weight:
PVDF HSV 900—3.24%
Graphene flakes—15.68%
MP solvent—81.08%

An example procedure to prepare the ink for the second current collector layer 6 includes:
Prepare PVDF HSV 900 base: Heat MP to 60° C. and progressively add PVDF HSV 900. Mix for 30 minutes at 60° C. using a laboratory egg. Disperse graphene flakes in MP using ultrasonic bath (15 minutes). Add the grapheme-MP dispersion to the PVDF HSV 900 base while keeping stirring for another 60 minutes.

An example curing profile for the ink for the second current collector layer 2 fabricated using the above example is at a temperature of 130° C. for between 3 and 5 minutes.

An example composition of a polymer insulator layer comprises, by weight:
PVDF HSV 900—10%
MP solvent—90%

A higher percentage of PVDF HSV 900 would result in higher viscosity and a lower percentage of PVDF HSV 900 would result in a lower viscosity, which can affect the thickness of a printed layer. Printed layers are generally desired to be as thin as possible, but still able to perform their intended function, such as acting as an environmental barrier for an insulator layer 7.

An example procedure to prepare the ink for the insulator layer 7 includes:
Heat MP to 60° C. and progressively add PVDF HSV 900. Mix for 30 minutes at 60° C. using a laboratory egg. An example curing profile for the ink for the insulator layer 7 fabricated using the above example is at a temperature of 130° C. for between 3 and 5 minutes Example Printed Battery Physical Parameters
Example Thicknesses of the Printed Layers The current collector layer 1 may have a thickness in a range from about 2 μm to about 5 μm.

A zinc (Zn) electrode layer (e.g., the first electrode layer 2) may have a thickness in a range from about 20 μm to about 70 μm, for example depending on a material of the substrate 8 and absence or presence of the current collector layer 1.

The intermediate layer 3 may have a thickness in a range from about 1 μm to about 3 μm.

The separator layer 4 may have a thickness in a range from about 10 μm to about 30 μm.

A $MnO_2$ electrode layer (e.g., second electrode layer 5) may have a thickness in a range from about 20 μm to about 60 μm.

The second current collector layer 6 may have a thickness in a range from about 5 μm to about 7 μm.

The insulator layer 7 may have a thickness of about 10 μm.

The total thickness of a fully printed battery including the layers 1-7 may have a thickness in a range from about 70 μm to about 200 μm.

The substrate 8 can have thickness in a range from about 10 μm to about 200 μm, making a maximum thickness of the device about 400 μm. On thin substrates 8 (e.g., substrates 8 having a thickness of about 30 μm to about 60 μm), the total thickness of a fully printed battery including the layers 1-7 can be as thin as about 130 microns.

Physical Characteristics of Printed $Zn/MnO_2$ Battery

An example of printed battery 30 on an Al substrate is shown in FIGS. 3A and 3B. The example printed battery 30 has a round shape (e.g., having a diameter of about 18 mm) and has been cut out from the Al substrate. The overall thickness of the battery 30 (including the Al substrate) is about 200 microns. The example battery 30 has a total weight of about 0.137 grams (g). Approximately ⅔ of the total weight is the weight of the 60 microns thick Al substrate.

Figure 5:
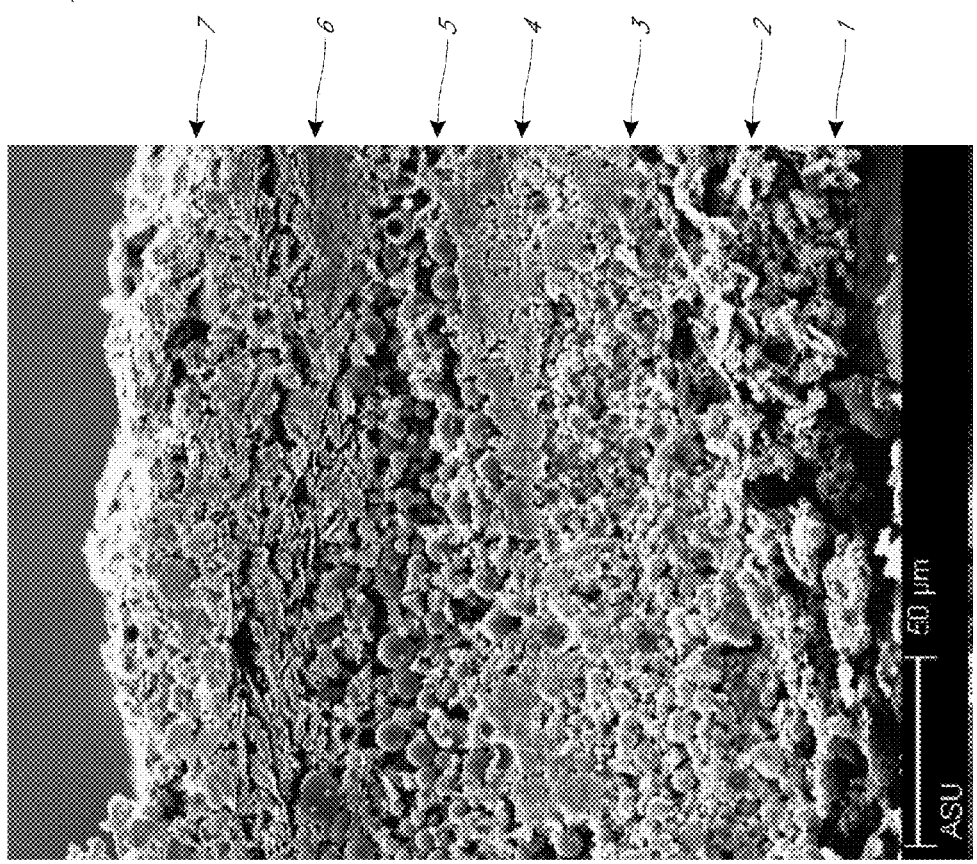
FIG. 5 is a scanning electron microscope (SEM) image of a cross section of an example embodiment of a printed battery.

FIG. 5 shows SEM image of a cross-section of an example printed battery 50. The printed battery 50 shown in FIG. 5 is a $Zn/MnO_2$ battery. The example printed battery was cracked under liquid nitrogen and then imaged. A carbon foam (not shown) was used as a substrate for convenience of the "crack" preparation. The printed $Zn/MnO_2$ battery 50 printed on a carbon foam substrate includes: a carbon foam substrate structure; a thin layer of Ni current collector 1; a Zn anode layer 2 (Zn spheroid particles are visible in FIG. 5); a very thin intermediate layer 3; a glass sphere separator layer 4; a $MnO_2$ layer 5; and a thin graphene current collector layer 6.

Details of the Battery Performance

Figure 6:
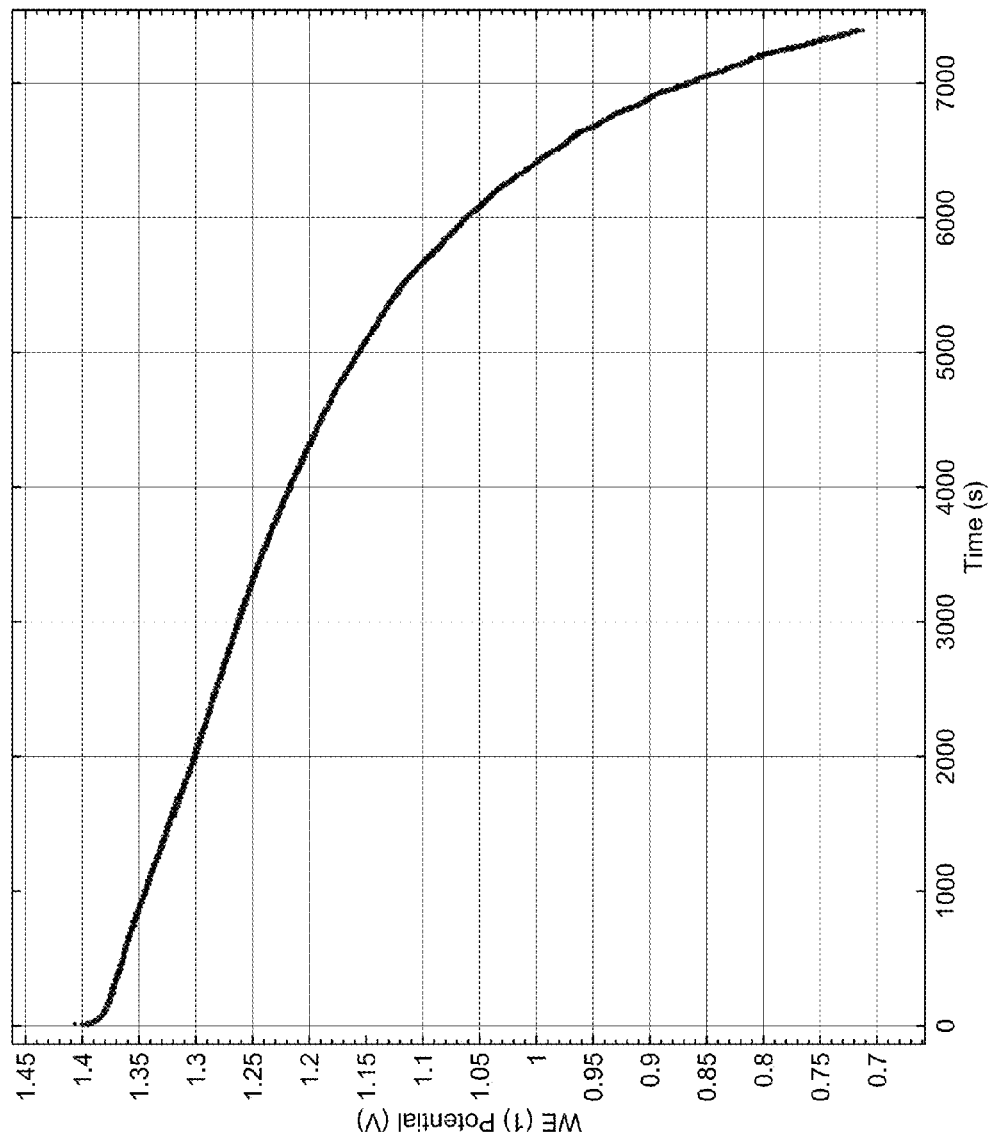
FIG. 6 is a graph of battery potential versus time of discharge for the printed battery of FIGS. 3A and 3B.

FIG. 6 is a graph of the dependence of battery potential versus time of discharge for the printed battery 30 of FIGS. 3A and 3B at constant current of about 0.06 mA/cm$^2$, or a constant current discharge curve The printed battery 30 was discharged with the current of 0.158 milliAmperes (mA) and lasted 1.9 hours. The cut-off voltage for the calculations was 0.9 V. The capacity of the printed $Zn/MnO_2$ battery 30 is 0.12 mAh/cm$^2$ at moderate current drain of 0.06 mA/cm$^2$. The open circuit potential of the printed battery 30 is 1.5 V and the working voltage is about 1.25 V.

Figure 7:
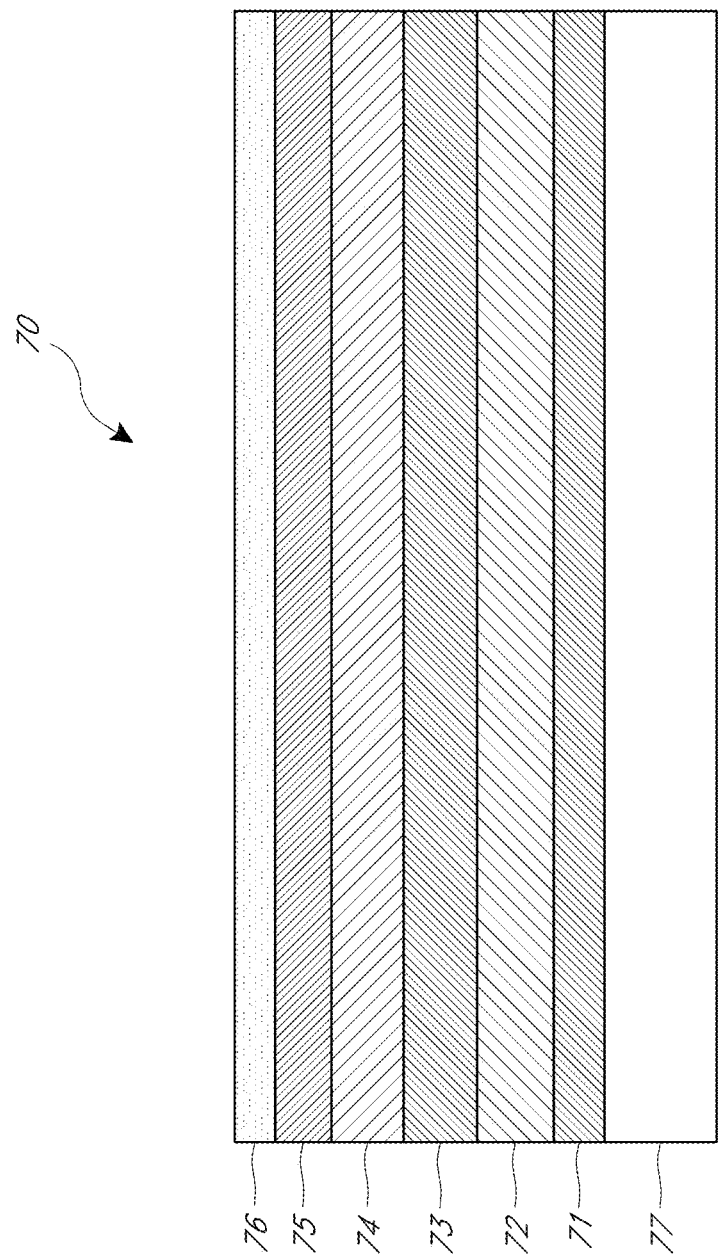
FIG. 7 is a cross-sectional or side elevational view of an example embodiment of a printed battery.

FIG. 7 shows a cross sectional or side elevational view of an example embodiment of a printed battery 70. The printed battery 70 can include a substrate 77, an optional first current collector layer 71 over the substrate 77, a first electrode layer 72 over the first current collector layer 71, a separator layer 73 (e.g., a separator including an electrolyte) over the first electrode layer 72, a second electrode layer 74 over the separator layer 73, and a second current collector layer 75 over the second electrode layer 74. In some embodiments, the printed battery 70 can include a separator sealing layer (not shown) beneath and/or above the separator layer 73. The separator sealing layer may facilitate sealing of the separator layer 73, and/or adhesion of the separator layer 73 to one or more adjacent printed layers (e.g., the first electrode layer 72 and/or the second electrode layer 74). In some embodiments, the separator sealing layer can have a same or similar composition and/or thickness as the intermediate layers described herein (e.g., intermediate layer 3 as shown in FIG. 1, having a thickness of less than about 1 micrometer (μm)). In some embodiments, each layer can be printed sequentially (e.g., one layer over the previous layer) for forming the battery 70. In some embodiments, an optional insulator layer 76 can be printed over the second current collector layer 75 to facilitate sealing of the battery 70 (e.g., for providing a hermetic seal for the printed battery 70). In some embodiments, the first electrode layer 72 can be printed onto the substrate 77, for example without the first current collector layer 71, if the substrate 77 comprises or is an electrically conductive material. In some embodiments, the first current collector 71 and/or the second current collector 75 can have a similar or same composition as other current collectors described herein (e.g., the current collectors 1, 6 of FIG. 1). In some embodiments, example embodiments of the first current collector 71 and/or the second current collector 75 can include nickel, for example being made from a conductive nickel-containing film. Examples of suitable nickel-containing films are provided in pages 28-43 of PCT Patent Application No. PCT/US2013/078059, filed Dec. 27, 2013, the disclosure of which is incorporated herein by reference in its entirety.

Figure 8:
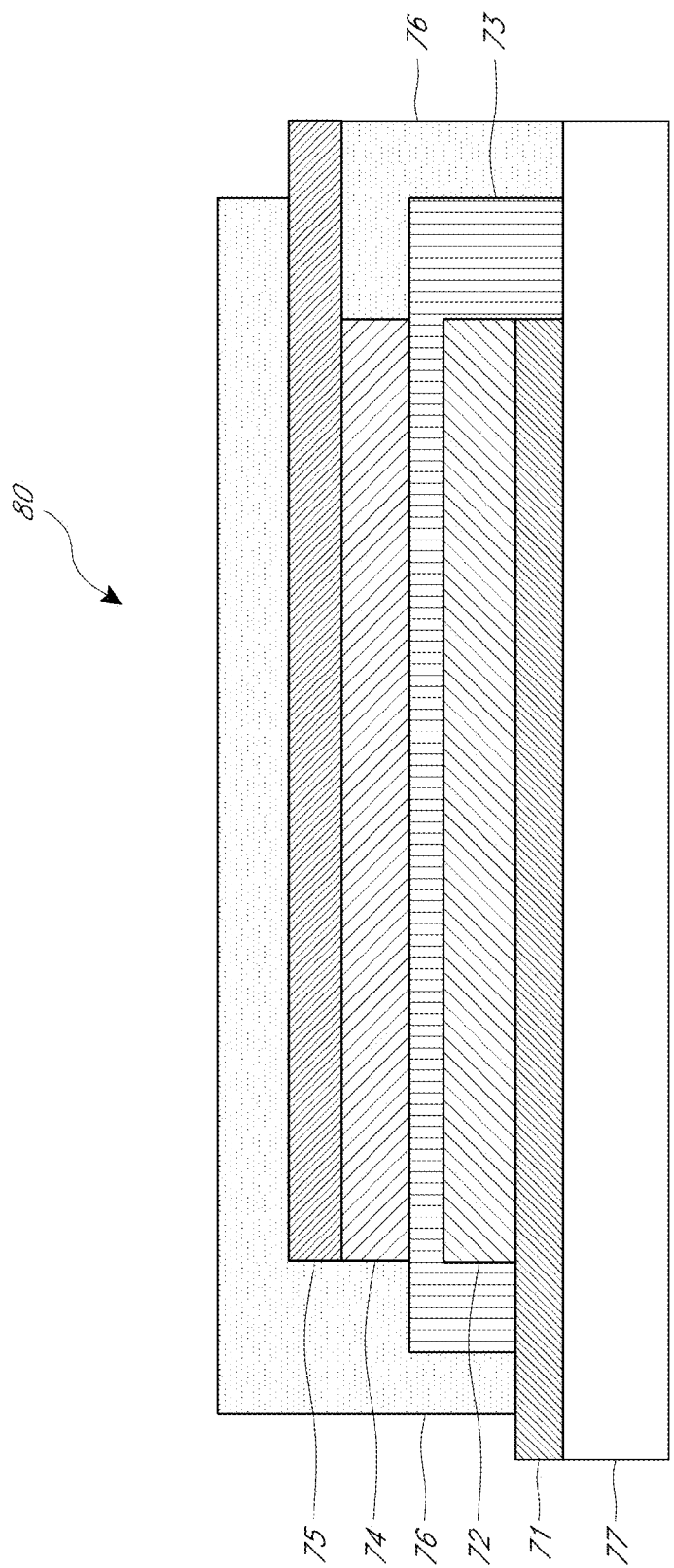
FIG. 8 is a cross-sectional or side elevational view of another example embodiment of a printed battery.

FIG. 8 is a cross-sectional or side elevational view of another embodiment of a printed battery 80, for example a battery 80 comprising the layers 71-76 shown in FIG. 7. In some embodiments, the printed battery 80 can include a separator sealing layer (not shown) beneath and/or above the separator layer 73. The battery 80 may be formed over a substrate 77. The current collector layers 71, 75 may laterally extend beyond the electrode layers 72, 74, for example to facilitate coupling with an external circuit. The separator layer 73 may form an enclosure over at least a portion of first electrode layer 72, for example to facilitate separation between the two electrode layers 72, 74. The insulator layer 76 may form an enclosure around the electrode layers 72, 74 and the separator layer 73, for example to seal the layers of the printed battery 80 (e.g., with a hermetic seal). In some embodiments, the battery 80 is a zinc-manganese dioxide (Zn/MnO$_2$) battery, the first electrode layer 72 comprising a zinc electrode and the second electrode layer 75 comprising a manganese dioxide (MnO$_2$) electrode. In some embodiments, the separator layer 73 can include a component that provides structural integrity to the separator layer 73 (e.g., a plurality of glass spheres, such as glass microspheres as described herein). In some embodiments, the separator layer 73 can be impregnated (e.g., soaked) with an electrolyte. In some embodiments, the insulator layer 76 can comprise or be made of a polymer insulator material for sealing the battery 80 (e.g., for providing a hermetic seal).

In some embodiments, a printed separator layer (e.g., the separator layer 73 of FIG. 7, the separator layer 73 of FIG. 8) is porous. As described herein, a separator layer may include components that provide structural support to the separator layer, such as microspheres (e.g., solid supports such as glass particles having a spherical or substantially spherical shape). A separator layer including structural support components may advantageously demonstrate improved ability to maintain a desired separation between electrodes of the battery (e.g., to inhibit, prevent, or substantially prevent an electrical short in the battery), for example during the application of pressure to components of the battery such as during printing subsequent layers of the battery. The separator layer can be printed on and/or over a previously printed battery layer, for example facilitating fabrication of a printed battery having all layers which are printed (e.g., sequentially printed on a substrate). Additional layers of the printed battery can be printed on and/or above the printed separator layer subsequently. In some embodiments, the porosity of the separator layer may advantageously facilitate holding of a liquid electrolyte by the separator (e.g., a liquid electrolyte which can be printed in a process subsequent to the process for printing of the separator layer). For example, a separator layer including pores that can provide a direct or substantially direct path from a first surface of the separator (e.g., a surface adjacent a first electrode) to an opposite second surface of the separator (e.g., a surface adjacent to a second electrode), and holding a liquid electrolyte, may facilitate improved ionic conductance between electrodes of the battery. In some embodiments, a separator layer including pores having a size between about 0.1 microns and about 10 microns (e.g., about 1 micron). Pore size may depend, for example, on at least one of polymer concentration, filler (e.g., microsphere) concentration, filler type, and/or filler size. The pores may be filled with a liquid electrolyte can provide improved ionic conductance between a first electrode layer and a second electrode layer, for example having an improved ionic conductivity as compared to a separator having a solid state electrolyte (e.g., an electrolyte which is included in a mixture for preparing the separator layer, and where the mixture is cured during the battery fabrication process for removing one or more solvents of the mixture, such as during the fabrication process of the separator layer).

Figure 9:
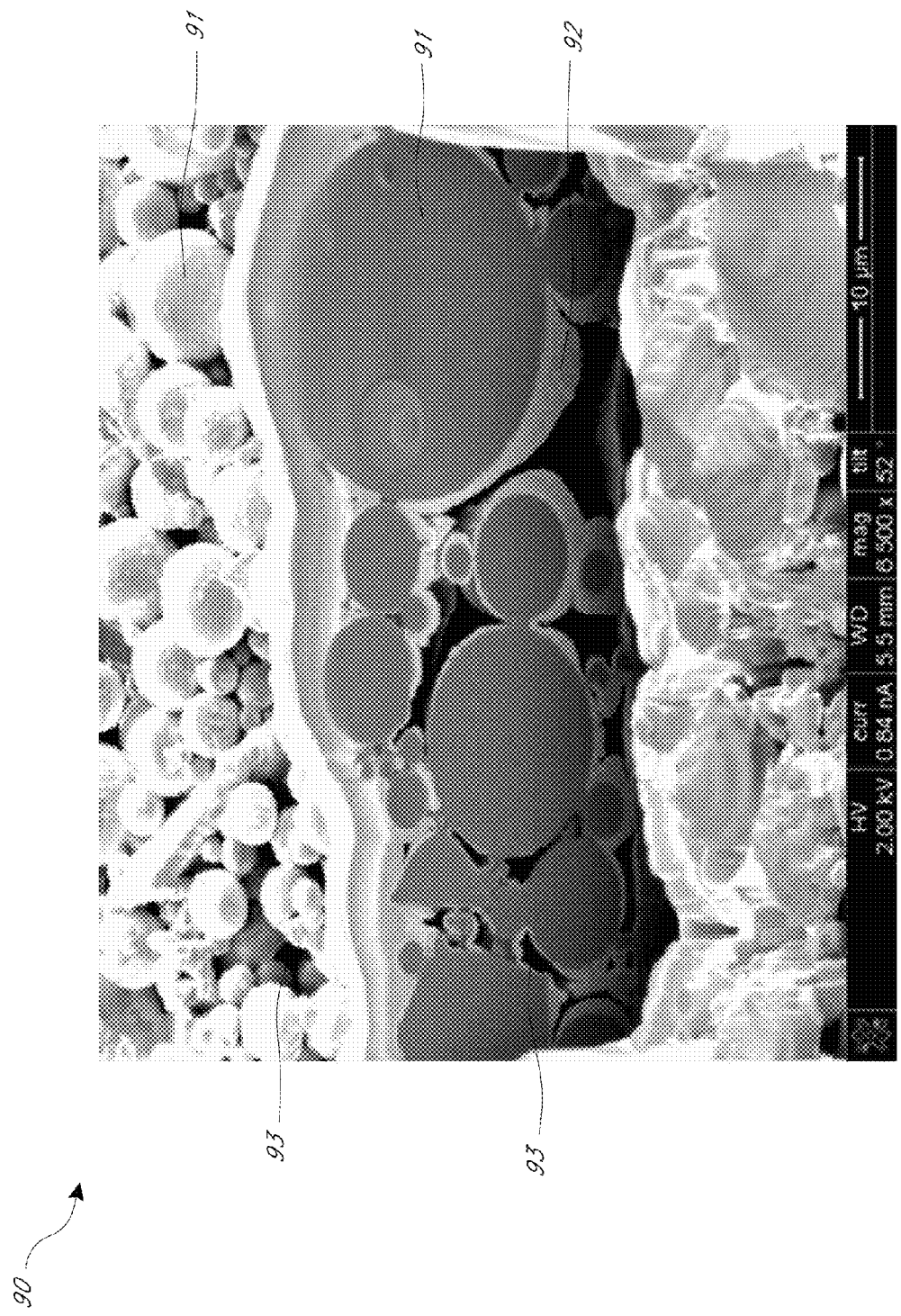
FIG. 9 is a SEM image of a cross section of an example embodiment of a printed separator.

FIG. 9 shows a tilt SEM image of an example embodiment of a printed separator layer 90, the SEM image showing both an angled top view and a cross-section view of the printed separator layer 90. In the top view, spherical structures 91 (e.g., glass microspheres that may be at least partially coated with polymer) are shown, although coated with platinum to enhance visibility. The spherical structures 91 can provide structural support for the separator layer 90. Pores 93 (e.g., pores resulting from one or more solvents evaporating during curing of the separator layer ink) are visible between the spherical structures 91. The pores 93 may result from evaporation of solvent in the ink used to print the separator layer 90, for example after printing and/or after curing. The pores 93 have irregular sizes, including some dimensions having a size between about 0.1 microns and about 10 microns. As described herein, an electrolyte can be held in one or more pores 93 of the printed separator layer 90, for example after seeping into the pores upon printing of an electrolyte layer on and/or over the separator layer 90, and/or upon heating of an electrolyte layer previously printed on and/or over the separator layer 90. Spherical structures 91, polymer 92, and a plurality of pores 93 can be seen in the cross-sectional view. The polymer 92 at least partially coats at least some of the spherical structures 91. Polymer coverage can at least partially depend, for example, on polymer type, filler type, polymer concentration, filler concentration, and/or solvent type.

In some embodiments, a printed battery (e.g., the printed battery 70 and/or the printed batter 80) includes a printed electrolyte. The electrolyte may be printed on a printed separator layer (e.g., separator layer 73 of FIG. 7, separator layer 73 of FIG. 8, separator layer 90 of FIG. 9). In some embodiments, the printed electrolyte has no or substantially no other additives, for example no additives in addition to an ionic liquid and a salt. For example, the electrolyte can have sufficient viscosity for printing directly onto a separator layer. In some embodiments, the printed electrolyte diffuses into the pores of the separator layer. For example, the electrolyte can fill or substantially fill the pores of the porous separator layer. In some embodiments, all or substantially all of the printed electrolyte diffuses into the pores of the printed separator layer prior to the printing of a subsequent layer of the printed battery. In some embodiments, after printing, the printed electrolyte layer is heated to facilitate reduction in the viscosity of the printed electrolyte layer, facilitating diffusion of the electrolyte into the pores of the separator layer. For example, heating of the printed electrolyte layer can hasten the process of filling the pores of the separator layer with the electrolyte. For example, no or substantially no electrolyte remains above the separator layer upon completion of the process in which at least the electrolyte layer is heated, when a second electrode layer (e.g., second electrode layer 74 of FIG. 7, second electrode layer 74 of FIG. 8), and/or a separator sealing layer is printed on the separator layer. Little or none of the electrolyte layer may evaporate during the heating and diffusion process.

In some embodiments, an amount of electrolyte printed on a separator layer can depend at least partially on, for example, separator layer thickness and/or separator layer porosity (e.g., pore size, number of pores). As described above, the separator layer porosity can at least partially depend on separator layer polymer concentration, separator layer filler concentration, separator layer filler type, and/or separator layer filler size. In some embodiments, the amount of electrolyte printed is controllable using different mesh sizes during a screen printing process. Excess electrolyte can be wiped away, or trial and error can be performed to select a desired or appropriate mesh size for the screen printing process after an initial estimate based on, for example, separator layer thickness and porosity, such that the printed electrolyte remaining in the printed battery is in the pores of the separator layer. A printed electrolyte may reduce, eliminate, or substantially eliminate an electrolyte dosimetry process, which can be used for filling a separator having no electrolyte with electrolyte. In some embodiments, a printed battery including an electrolyte layer which is printed onto a separator can facilitate improved ionic conductivity between electrodes of the printed battery, for example as compared to a battery having an electrolyte which is incorporated as part of an ink for the separator layer and is printed as part of the separator layer (e.g., having an improved ionic conductivity as compared to solid state electrolytes, such as electrolytes which are included in an ink for forming the separator layer, where the ink for the separator layer includes, for example, one or more ionic liquids, a material for providing structural strength for the separator layer, such as a polymeric material, and/or a solvent, and where the solvent is removed or substantially removed in the battery fabrication process).

In some embodiments, a separator sealing layer (e.g., the separator sealing layer as described with reference to FIG. 7, the separator sealing layer as described with reference to FIG. 8) is printed over a porous separator layer (e.g., the separator layer 73 of FIG. 7, the separator layer 73 of FIG. 8, the separator layer 90 of FIG. 9). For example, the separator sealing layer can be printed subsequent to printing the electrolyte layer on the porous separator layer. A separator sealing layer may facilitate sealing of pores of the porous separator layer. For example, a separator sealing layer may advantageously facilitate sealing of pores of the porous separator layer prior to printing a second electrode layer, such as to provide improved retention of the printed electrolyte within the porous separator layer, and/or improved adhesion between the porous separator layer and the second electrode layer. In some embodiments, a separator sealing layer can reduce and/or prevent or substantially prevent seeping of one or more adjacent layers into the separator layer (e.g., seeping of a first electrode layer and/or a second electrode layer into the separator layer), for example due to pressure (e.g., pressure applied during a subsequent printing process). In some embodiments, the separator sealing layer can have a composition similar to that of an intermediate layer, such as the intermediate layer 3 shown in FIG. 1. In some embodiments, the separator sealing layer may or may not include an electrolyte.

Figure 10:
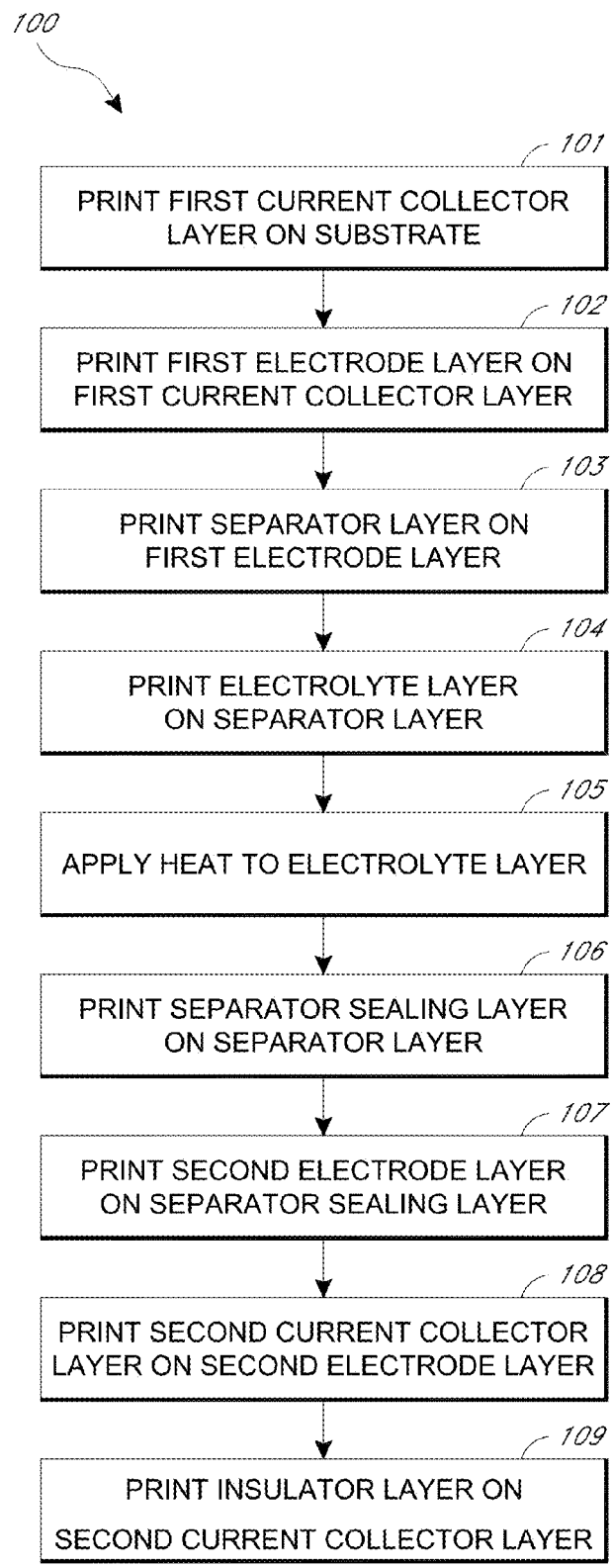
FIG. 10 is an example embodiment of a process for fabricating an example embodiment of a printed battery.

FIG. 10 shows an embodiment of an example process for fabricating a printed battery (e.g., printed battery 70, and/or printed battery 80). In block 101, a first current collector layer can optionally be printed over and/or on a substrate. As described herein, a first current collector may be omitted if the substrate is or comprises conductive material. In block 102, a first electrode layer can be printed over and/or on the first current collector layer. In block 103, a separator layer can be printed over and/or on the first electrode layer. In block 104, an electrolyte can be printed over and/or on the separator layer. As described herein, the printed electrolyte can diffuse into the pores of the separator layer to provide a separator layer including a plurality of pores having the electrolyte (e.g., a plurality of pores filled or substantially filled with the electrolyte). In block 105, heat can be applied to the printed electrolyte layer, for example to facilitate diffusion of the printed electrolyte into the separator layer. The heating process may facilitate diffusion of the electrolyte into the pores of the separator layer by reducing viscosity of the printed electrolyte layer, for example reducing a duration in which all or substantially all of the printed electrolyte diffuses into the separator layer. In block 106, a separator sealing layer (e.g., an intermediate layer) can optionally be printed on the separator layer, for example subsequent to the heating process. In some embodiments, no or substantially no electrolyte remains on the separator layer when the subsequent layer is printed on the separator layer. A separator sealing layer may be printed over the separator layer (e.g., as described with respect to block 106) and/or under the separator layer (e.g., between block 102 and block 103). For example, separator sealing layers can be printed both prior to printing the separator layer and subsequent to printing the electrolyte on the separator layer (e.g., subsequent to the diffusion of all or substantially all of the printed electrolyte into the separator layer). In some embodiments, a separator sealing layer is printed subsequent to applying heat to the printed electrolyte. The separator sealing layer may facilitate reduction of seepage of the electrolyte into one or more layers adjacent to the separator layer and/or seepage of one or more layers adjacent to the separator layer into the separator layer, such as due to pressure applied to the printed layers during the battery fabrication process. In some embodiments, the printed battery includes no separator sealing layer above and/or below the separator. In block 107, a second electrode layer can be printed over and/or on the separator sealing layer. In block 108, a second current collector layer can be printed over and/or on the second electrode layer. In block 109, an insulator layer can be printed over and/or on the second current collector layer. In some embodiments, the insulator layer facilitates sealing of the printed battery. For example, the insulator layer may form an enclosure around the printed electrode layers and the printed separator layer.

It was unexpectedly discovered that applying a centrifugal force (e.g., centrifuging) to a solution including a salt and an ionic liquid can provide a solution having two or more distinct or substantially distinct phases, such as an upper phase and a lower phase. In some embodiments, an upper phase of the centrifuged solution is a liquid phase. In some embodiments, a lower phase of the centrifuged solution has an increased viscosity as compared to the upper phase (e.g., the lower phase can be a gel-like substance).

For example, a 0.7 mol/l (M) solution including zinc tetrafluoroborate in 1-ethyl-3-methylimidazolium tetrafluoroborate centrifuged at 10000 revolutions per minute (rpm) for 5 minutes (min) can provide a solution separated into two phases. An upper phase can be a transparent liquid having a concentration of about 0.6 M to about 0.7 M zinc tetrafluoroborate. A lower phase can be a gel having a concentration of about 0.7 M to about 0.8 M zinc tetrafluoroborate. In some embodiments, the lower phase can have an ionic conductivity similar to that of the upper phase. Other solution concentrations, speeds of centrifugation and/or durations of centrifugation may also be suitable. In some embodiments, the solution can be centrifuged at a speed of about 3,000 rpm to about 30,000 rpm, including about 3,000 rpm to about 15,000 rpm. In some embodiments, the solution can be centrifuged for a duration of about 30 seconds to about 15 minutes, including about 1 minute to about 10 minutes. For example, higher speeds and/or longer durations may be used for solutions with a higher initial concentration and/or specific gravity, and lower speeds and/or shorter durations may be used for solutions with a lower initial concentration and/or specific gravity. For another example, higher speeds can be used with lower durations, and lower speeds can be used with higher durations. The concentration of each phase can be measured by ion chromatography (e.g., commercially available from Metrohm USA Inc., of Riverview, Fla.).

The separation of the Zn salt solution in ionic liquid into two phases is a previously unknown phenomena. An upper phase and a lower phase can be solutions of zinc salt in ionic liquid (e.g., a zinc salt dissolved in an ionic liquid to a molecular level). In some embodiments, the lower phase includes a molecular agglomerations of ionic liquid around zinc cations (e.g., at least partially due to a tendency of ionic liquids to form agglomeration). The upper phase may be relatively depleted of Zn ions as compared to the initial concentration of the electrolyte (e.g., prior to centrifuging). The lower phase may be relatively enriched with Zn ions as compared to the initial concentration of the electrolyte (e.g., prior to centrifuging).

The lower phase can have a consistency of a printable ink (e.g., more viscous than the ionic liquids and/or the non-centrifuged mixture of the zinc salts and ionic liquids).

In some embodiments, the upper phase can be used elsewhere in the battery fabrication process, for example as an additive to an ink for a Zn electrode.

In some embodiments, styrene butadiene rubber can be used as a binder material for an electrode of a printed battery, and/or for a separator layer of a printed battery. This is a suspension of rubber, not a dissolved polymer in a solvent. For example, when electrodes and/or a separator layer are dried, the rubber may not solidify to form a continuous film. In some embodiments, an electrode including a suspension of rubber facilitates formation of pathways between active particles of the electrode (e.g., bridges between the active particles), for example providing more room for the electrolyte to contact the active particles. In some embodiments, a separator layer including a suspension of rubber facilitates ionic transport between electrodes of the printed battery, for example providing more room for mobility of the electrolyte.

In some embodiments, the styrene butadiene rubber may increase flexibility of the printed layers including the styrene butadiene rubber and/or the printed device as a whole.

In some embodiments, styrene butadiene rubber can be used in the fabrication of Zn/MnO2 batteries, such as in the fabrication of one or more electrodes of the batteries, and/or a separator layer of the batteries.

In some embodiments, a printed battery (e.g., printed battery 70 of FIG. 7, printed battery 80 of FIG. 8) includes one or more printed layers being printed from an ink having a water and/or water soluble solvent as the main solvent. In some embodiments, each layer of a printed battery can be printed from an ink having one or more water and/or water soluble solvents. For example, water, a water-like solvent (e.g., an alcohol), and/or water-soluble solvent (e.g., an alcohol) can be an ink carrier (e.g., a volatile component, a vaporizable element, and/or a viscosity modifier, of the ink) for the polymeric component of the ink used in printing the one or more printed layers. An ink for the one or more printed layers can be a colloidal suspension including small particles of the polymeric component in the water-soluble solvent. Drying of the colloidal suspension in forming the printed layer may form a non-continuous film, which may facilitate improved conductivity of the electrolyte, for example facilitating movement of the electrolyte through the film. In some embodiments, a battery (e.g., all layers of a printed battery) having water and/or water soluble solvents as the main solvent can facilitate ecologically friendly processes in the manufacturing of the battery, for example, as compared to polyvinylidene fluoride (PVDF) based batteries, facilitate fabrication of batteries having improved electrical performance (e.g., improved conductivity), and/or facilitate reduced costs of manufacturing. For example, PVDF based batteries can often include toxic solvents for dissolving the PVDF, and may use a significant amount of energy for the dissolution of PVDF in the toxic solvents. PVDF can be more expensive than the polymers described herein. In some embodiments, expensive PVDF is fully dissolved, using much energy, to form a true solution in the toxic solvents. A layer printed from a PVDF solution can dry as a continuous film, which may disadvantageously slow electrolyte travel through the film (e.g., because there are no discontinuities through which the electrolyte may travel), reducing conductivity of the continuous film and/or the printed battery made with the continuous film.

In some embodiments, water and/or water soluble solvents have lower boiling points than solvents used for PVDF, facilitating use of lower drying temperatures for the printed films and/or reduced time for drying the printed films.

Example Compositions of Printed Battery Layers

An example composition of a first electrode layer (e.g., referring again to FIGS. 7 and 8, the first electrode layer 72), such as a Zn electrode, by weight:

Styrene Butadiene Rubber (SBR)—1.04%
Zn powder (particle size below 10 microns)—97.2%
Electrolyte 1 mol/l (M) $ZnBF_4$ in $C_2mimBF_4$—1.76%

An example composition of a separator layer (e.g., separator layer 73), such as a separator layer including microspheres (e.g., glass spheres), by weight:

Polytetrafluoroethylene (PTFE)—2.34% (Alternatively or in addition, styrene butadiene rubber (SBR) can be used. For example the separator layer can include 2.34% by weight of styrene butadiene rubber.)
Glass spheres (less than 20 microns in diameter)—95.32%

PVA (polyvinyl alcohol) 133,000 molecular weight—0.38%

PVA 6,000 molecular weight—1.96%

The separator's pores can be filled with printed gel electrolyte (e.g., as described herein) having a concentration between about 0.7 M and about 0.8 M zinc tetrafluoroborate in 1-ethyl-3-methylimidazolium tetrafluoroborate.

An example composition of a separator sealing layer (e.g., the separator sealing layer as described with reference to FIG. 7, the separator sealing layer as described with reference to FIG. 8), by weight:

Polyvinyl alcohol (PVA) 133,000 molecular weight—6.86%

PVA 6,000 molecular weight—35.73%

Electrolyte 0.6 mol/l (M) $Zn(BF_4)_2$ in $C_2mimBF_4$—57.41%

An example composition of a second electrode layer (e.g., referring again to FIGS. 7 and 8, the second electrode layer 74) such as a $MnO_2$ electrode, by weight:

Styrene Butadiene Rubber—4.3%

Manganese dioxide ($MnO_2$)—77.3%

Multiwall carbon nanotubes (MWCNT)—2.8% (it can be any mixture of MWCNTs and graphite or graphene)

Ionic liquid (1-ethyl-3-methylimidazolium tetrafluoroborate, $C_2mimBF_4$)—15.6%

Current collectors (e.g., referring again to FIGS. 7 and 8, the first current collector 71 and the second current collector 75) can have a similar or same composition as other current collectors described herein (e.g., the current collectors 1, 6 of FIG. 1). As described herein, in some embodiments, the first current collector 71 and the second current collector 75 can comprise or be made of a conductive nickel-containing film. Examples of embodiments of a nickel-containing film are provided in pages 28-43 of PCT Patent Application No. PCT/US2013/078059, filed Dec. 27, 2013, the disclosure of which is incorporated herein by reference in its entirety.

An example composition for an insulator layer (e.g., referring again to FIGS. 7 and 8, the insulator layer 76), such as a polymer insulator layer, by weight:

Specialty copolymer based on vinylidene chloride and vinyl chloride monomers (e.g., Ixan® SGA-1, available from Solvay Specialty Polymers USA, LLC, of Alpharetta, Ga.)—100%

Example Compositions of Printable Ink Compositions (Examples of Successful Ink Compositions), Preparation Process, Properties and Curing Conditions An example composition of an ink for forming a first electrode (e.g., the electrode layer 72 of FIG. 7 and/or FIG. 8), such as a Zn electrode, by weight:

Styrene Butadiene Rubber (SBR)—0.9%

Zn powder (particle size below 10 microns)—83.9%

Water—12.11%

N-butanol—2%

Zinc tetrafluoroborate $Zn(BF_4)$—0.14%

$C_2mimBF_4$—1.36%

An example procedure to prepare the ink for a printed electrode layer (e.g., the first electrode layer 72 in FIGS. 7 and 8) can include:

Combine a 15% SBR suspension in water such as a Modified Styrene Butadiene copolymer hydrophilic binder (e.g., PSBR-100 available from Targray, of Quebec, Canada), an upper phase of an electrolyte (see description of the electrolyte preparation herein), and water for achieving good viscosity. Preheat the combination to 40° C. and stir for 30 min using laboratory egg.

The ink for the electrode layer fabricated according to the example method can have a viscosity of about 8000 cP. An example curing profile for this composition is at a temperature of 100° C., for between 3 and 5 minutes.

An example composition of an ink for forming a separator layer (e.g., the separator layer 72 of FIGS. 7 and 8), such as a separator layer including glass spheres, by weight:

Polytetrafluoroethylene (PTFE)—1.43% (Alternatively or in addition, styrene butadiene rubber (SBR) can be used. For example 1.43% by weight of styrene butadiene rubber can be used.)

Glass spheres (less than 20 microns in diameter)—58.3%

Polyvinyl alcohol (PVA) 133,000 molecular weight—0.23%

PVA 6,000 molecular weight—1.20%

Water—36.83%

N-Butanol—2%

An example procedure to prepare the ink for the printed separator layer 73 can include:

Prepare a PVA base: preheat water to 40° C., add PVA 133K and PVA 6K and mix until dissolved using laboratory egg. Add 60% PTFE suspension in water (e.g., polytetrafluoroethylene preparation, 60 wt % dispersion in $H_2O$, available from Sigma-Aldrich, of Switzerland) and glass spheres to the PVA base. Mix for 10 minutes at room temperature using laboratory egg.

The ink for the separator layer fabricated according to the example method can have a viscosity of about 10000 cP. An example curing profile for this composition is at 100° C., for between 3 and 5 minutes.

An example composition of an ink for the printed electrolyte, by weight:

0.7-0.8 mol/l viscous solution of zinc tetrafluoroborate in 1-ethyl-3-methylimidazolium tetrafluoroborate obtained after centrifuging (e.g., a lower phase of the centrifuged solution).

An example procedure to prepare the ink for the printed electrolyte can include:

Mixing the electrolyte with a magnetic stir bar for 2 hours at 40° C., the electrolyte having the following composition, by weight:

Ionic liquid (1-ethyl-3-methylimidazolium tetrafluoroborate, $C_2mimBF_4$)—90.57%

Zinc tetrafluoroborate ($Zn(BF_4)_2$)—9.43%.

Centrifuge the mixture at 10,000 rpm for 5 minutes. Two phases appear: transparent upper phase and a gel-like phase (e.g., a lower phase). The lower phase can be used as or for the printable electrolyte.

The ink for the printed electrolyte fabricated using the example method can have a viscosity of about 5000 cP. An example curing profile for this composition is at a temperature of 100° C., for between 3 and 5 minutes.

An example composition of an ink for a separator sealing layer, by weight:

Water—81.19%

Polyvinyl alcohol (PVA) 133,000 molecular weight—1.29%

PVA 6,000 molecular weight—6.72%

Electrolyte 1 mol/l (M) $Zn(BF_4)_2$ in $C_2mimBF_4$—10.8%

As described herein, the separator sealing layer can be with electrolyte or without electrolyte.

An example procedure to prepare the ink for the separator sealing layer can include:

Preheat water to 60° C. to 80° C. Slowly pour PVA 133,000 molecular weight. Mix using magnetic bar. Higher temperatures can dissolve the PVA more quickly. Add PVA 6000 molecular weight when the PVA 133,000 is dissolved. Reduce heat to 60° C. and add electrolyte drop wise. Stir using laboratory egg. Cool down the mixture until gelled.

The ink for the separator sealing layer fabricated using the example method can have a viscosity of about 100 cP. An example curing profile for this composition is at a temperature of 130° C., for between 5 and 7 minutes.

An example composition of an ink for forming a second electrode layer (e.g., the second electrode layer 74 of FIG. 7 and/or FIG. 8), such as a $MnO_2$ electrode, by weight:
Styrene Butadiene Rubber (SBR)—2.3%
Manganese dioxide ($MnO_2$)—41.1%
MWCNT (multiwall carbon nanotubes)—1.48% (any mixture of MWCNTs and graphite or graphene may be appropriate)
Ionic liquid (1-ethyl-3-methylimidazolium tetrafluoroborate, $C_2mimBF_4$)—8.29%
Water—50.79%
Butanol—2%

An example procedure to prepare the ink for the second electrode layer 74 can include:
Preparation of a MWCNTs paste in $C_2mimBF_4$ can be performed, for example, by two techniques:
A first technique can include taking 15% of MWCNTs and 85% of $C_2mimBF_4$, and grinding the mixture in a mortar and pestle in glove box for 5 min, then grind in automated mortar and pestle for 1 hour (e.g., such a technique can be suitable for small amounts). Grinding of the mixture can advantageously facilitate untangling of agglomerated carbon nanotubes, for example to facilitate solvation of the carbon nanotubes in the ionic liquid. Grinding of the mixture can facilitate untangling of agglomerated carbon nanotubes such that the carbon nanotubes are evenly or substantially evenly dispersed within the ionic liquid.
A second technique can include taking 15% of MWCNTs and 85% of $C_2mimBF_4$, and mixing for one day in a jar mill with zirconia grinding media (diameter of zirconia beads is 0.5-2 cm) (e.g., such a technique can be suitable for larger amounts). This forms a bucky gel in which the carbon nanotubes are evenly or substantially evenly dispersed in the ionic liquid $C_2mimBF_4$, for example such that the carbon nanotubes do not agglomerate. As described herein, grinding of the mixture comprising the carbon nanotubes and the ionic liquid can advantageously facilitate untangling of agglomerated carbon nanotubes and/or solvation of the carbon nanotubes in the ionic liquid.
Take SBR and mix with MWCNT paste under sonication and 50° C. for 30 min. Graphite and/or graphene can be optionally added to $MnO_2$ powder and mixed at 70° C. for 90 min using laboratory egg.

The ink for the second electrode layer fabricated using the example method can have a viscosity of about 9000 cP. An example curing profile for this composition is at a temperature of 100° C., for between 3 and 5 minutes.

Referring again to FIGS. 7 and 8, one or both of the first current collector 71 and the second current collector 75 can have a similar or same composition as other current collectors described herein (e.g., the current collectors 1 and 6 of FIG. 1), and can be prepared according to methods as described herein. As described herein, in some embodiments, the first current collector 71 and the second current collector 75 can include nickel. For example, the first current collector 71 and the second current collector 75 can be made of a nickel-containing film, example compositions of and methods of fabricating a nickel-containing film are provided in pages 28-43 of PCT Patent Application No. PCT/US2013/078059, filed Dec. 27, 2013, the disclosure of which is incorporated herein by reference in its entirety.

An example composition of an ink for forming an insulator layer (e.g., the insulator layer 76 of FIG. 7 and/or FIG. 8), by weight:
Specialty copolymer based on vinylidene chloride and vinyl chloride monomers (e.g., Ixan® SGA-1, available from Solvay Specialty Polymers USA, LLC, of Alpharetta, Ga.)—10%
N-Butanol solvent—90%

An example procedure to prepare the ink for the insulator layer can include:
Heat butanol to 60° C. and progressively add the copolymer. Mix for 30 min at 60° C. using laboratory egg.

The ink for the insulator layer fabricated using the example method can have a curing profile at a temperature of 130° C., for between 3 and 5 minutes.

Examples of Physical Parameters and Electrical Performance of a Printed Battery

Example thicknesses of the printed layers of a printed battery (e.g., the printed battery 70 of FIG. 7 or the main lateral portions of the printed battery 80 of FIG. 8) can include:
1. First current collector: 5-25 micrometers (μm) or 0 μm (e.g., if the substrate comprises or is electrically conductive material)
2. Zinc electrode: 20-70 micrometers (μm), depending on substrate and absence/presence of the first current collector
3. Glass sphere separator: 10-30 micrometers (μm)
4. Printed electrolyte is completely adsorbed in the glass separator pores.
5. Separator sealing layer: less than 1 micrometer (μm)
6. $MnO_2$ electrode: 20-60 micrometers (μm)
7. Second current collector: 5-25 micrometers (μm)
8. Protective layer: around 10 micrometers (μm)
Overall thickness of the printed battery: 70-220 micrometers (μm)

Substrates can have thickness 10-200 micrometers (μm) making the total thickness of the device about 400 micrometers (μm). On thin substrates (e.g., substrates having a thickness of about 30 to about 60 micrometers (μm)) the overall battery thickness can be as thin as about 130 micrometers (μm).

The printed batteries can be printed in any suitable shape. For example, referring again to FIG. 8, some portions of the 73 overlap the layers 71 and/or 72. For another example, although shown as an example cross-section or side elevational view, a top plan view can include shapes such as quadrilaterals, other polygons, round shapes, combinations thereof, etc.

Using suspensions of polymers (e.g., Styrene Butadiene Rubber and PTFE) rather than polymers dissolved in solvents in most of the layers, and having a rubber (e.g., Styrene Butadiene Rubber) as a binder material of the electrodes, can facilitate improved flexibility of the battery.

Details of Battery Performance

Figure 11:
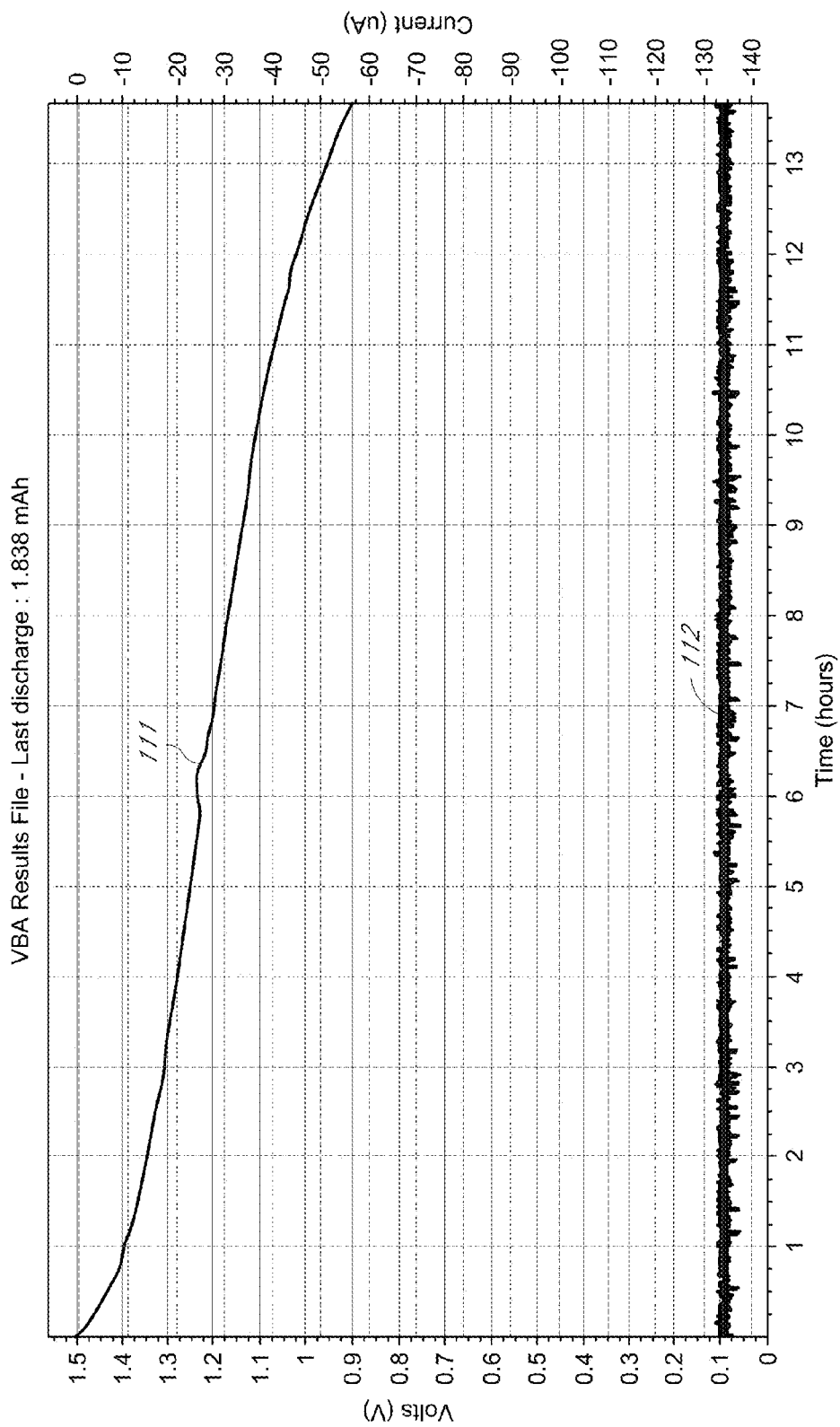
FIG. 11 is a graph of battery potential versus time of discharge for an example printed battery.

Graph 111 of FIG. 11, with reference to the y-axis labeled with voltage in Volts (V), is a graph of battery potential versus time for discharge of an example printed battery including the layers described with respect to FIGS. 7 and 8 and having a rectangular shape and dimensions of 1 centimeter (cm) by 2 cm. Graph 112 of FIG. 11, with references to the y-axis labeled with of current in microamperes (μA), shows that the printed battery was discharged at constant current 0.137 milliAmperes (mA) (or 0.068 mA/cm$^2$) (e.g., a constant current discharge curve). Measurements were performed on Vencon UBA5 Battery Analyzer (e.g., available from Vencon Technologies, Inc., of Ontario, Canada). The printed battery was discharged with the current of 0.137 (mA) and lasted 14 hours. The cut-off voltage for the calculations was 900 millivolts (mV). The capacity of the printed Zn/MnO$_2$ battery is about 1.838 milliampere-hour (mAh). The open circuit potential of the printed battery is 1.56 V. Below are the readings of a Vencon UBA5 Battery Analyzer for a printed battery having the above-listed physical characteristics (e.g., a printed zinc manganese dioxide, ZnMnO$_2$, battery):

Number of cells: 1
Rated capacity: 1.000 milliampere-hour (mAh)
Open circuit Voltage: 1.5566 Volts (V)
Relative Humidity: 22%
Curing: 290° F. for 8 min
Capacity: 1.838 milliampere-hour (mAh) (183.8% rated)
Summary of electrical performance of the printed battery: ZnMnO$_2$ discharge:
  Pass, Capacity=1.838 milliampere-hour (mAh) (183.8% rated), IPV=1.489 Volts (V), MPV=0.914 Volts (V), EPV=0.900 Volts (V), MP134.2 microamperes (µA).
  Duration (hour:minute:second): 13:40:29
  Load current: 137.1 microamperes (µA)
  Cut-off voltage: 900 mV
  Battery discharged capacity: 1.838 milliampere-hour (mAh)
  Battery initial-point voltage: 1.489 Volts (V)
  Battery mid-point voltage: 914 millivolts (mV)
  Battery end-point voltage: 900 millivolts (mV)
  Battery midpoint current: 134.2 microamperes (µA)
  Exit condition: Battery cut-off voltage reached.

Figure 12:
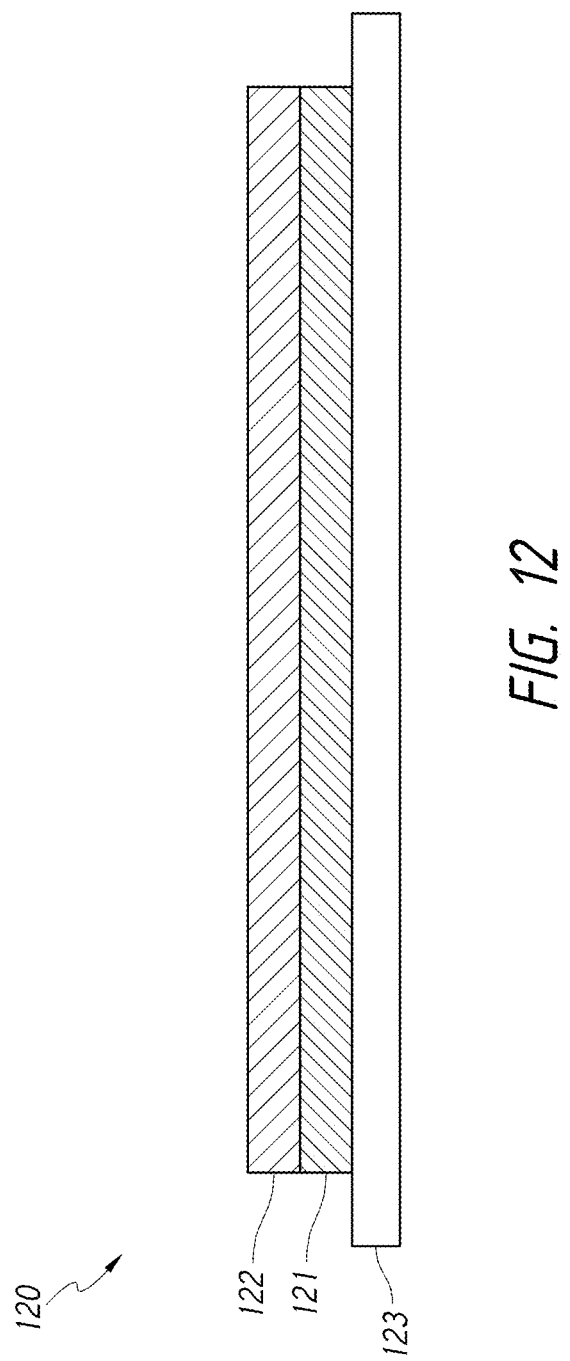
FIG. 12 a cross-sectional or side elevational view of an example embodiment of a portion of a battery.

FIG. 12 shows an example of a portion of a battery 120, for example a zinc manganese dioxide battery. FIG. 12 shows an electrode layer 122 over a current collector layer 121, and the current collector layer 121 over a substrate 123. The electrode layer 122 can be an electrode layer of an anode and/or an electrode layer of a cathode of the battery 120. The current collector layer 121 can be a cathode current collector layer and/or an anode current collector layer. The battery 120 may be fully or partially printed. In some embodiments, all or substantially all layers of the battery 120 are printed. In some embodiments, only some layers of the battery 120 are printed. For example, one or more of an anode electrode layer, an anode current collector layer, a cathode electrode layer, and/or a cathode current collector layer, may be printed.

As described herein, one or more layers of a battery can be printed on an electrically conductive or non-conductive substrate, including for example, graphite paper, graphene paper, polyester film, polyimide film, aluminum (Al) foil, copper (Cu) foil, stainless steel (SS) foil, carbon foam, polycarbonate film, paper, coated paper, plastic coated paper, fiber paper, cardboard, combinations thereof, and/or the like. For example, the current collector layer 121 can be printed onto an electrically non-conductive substrate, such on a Mylar™ (a polyester material) substrate.

In some embodiments, the battery 120 can be partially printed, comprising a printed anode electrode layer, printed anode current collector layer, printed cathode electrode layer, and printed cathode current collector layer. A partially printed battery 120 may be assembled, for example, by printing an anode current collector layer over a first substrate and printing an anode electrode layer over the anode current collector layer, and printing a cathode current collector layer over a second substrate and printing a cathode electrode layer over the cathode current collector layer. Subsequently, a non-printed separator can be sandwiched between the printed anode electrode and current collector layers, and the printed cathode electrode and current collector layers, for example by applying pressure upon one or both of the first and the second substrates.

In some embodiments, a partially printed battery 120 can be assembled using a roll-to roll process. For example, a non-printed separator can be impregnated with an electrolyte by rolling the non-printed separator through a container with the electrolyte (e.g., an electrolyte comprising 0.5 mol/L (M) to about 1M zinc tetrafluoroborate (Zn(BF$_4$)$_2$) in 1-ethyl-3-methylimidazolium tetrafluoroborate (C$_2$mimBF$_4$)). The presoaked separator can then be positioned between the printed layers (e.g., the printed anode electrode layer, anode current collector layer, cathode electrode layer, and cathode current collector layers), and passed between rollers of a rolling press. Other methods to apply may also be suitable. In some embodiments, the battery can be encapsulated using a lamination process, including for example, a polymer lamination process (e.g., using an adhesive), and/or a lamination process for forming metal foil pouches (e.g., to form a battery having a pouch-cell configuration). Other soft or hard packaging processes may also be suitable.

In some embodiments, the non-printed separator can comprise polypropylene, polyethylene, polytetrafluoroethylene, cellulose (e.g., methylcellulose, regenerated cellulose, cellophane, combinations thereof, and/or the like), aramid, combinations thereof, and/or the like. For example, a non-printed separator can be polypropylene based, polyethylene based, polytetrafluoroethylene based, cellulose based, and/or aramid based. In some embodiments, the non-printed separator can have a thickness of about 5 microns (µm) to about 150 microns. In some embodiments, the non-printed separator can have a porosity of about 20% to about 80%, and/or an average pore size of about 20 nanometers (nm) to about 100 nm. A non-printed separator can be selected to facilitate desired ion transport characteristics, compatibility with one or more other battery components and/or stability under operating conditions of the battery. In some embodiments, the non-printed separator can be commercially available, including for example, a polypropylene based separator coated with a surfactant material (e.g., Celgard® 3501, having a thickness of about 25 microns (µm), available from Celgard LLC of Charlotte, N.C.).

In some embodiments, the separator can be printed. For example, the printed separator can have a composition and/or can be fabricated according to one or more embodiments described herein.

Current Collector Layer

In some embodiments, a current collector can comprise nickel flakes. A current collector comprising nickel flakes may be cost effective, and/or may be chemically and/or electrochemically stable under operating conditions of the battery. For example, a current collector comprising nickel flakes may be chemically resistant or substantially chemically resistant to one or more other components of the battery, including for example an electrolyte of the battery (e.g., an electrolyte comprising ionic liquids). In some embodiments, a current collector comprising nickel flakes can have desired resistance to oxidation. In some embodiments, a current collector having nickel flakes as described herein can be chemically resistant or substantially chemically resistant to oxidation and/or corrosion over the life of the battery, and/or may be electrochemically stable across an operating voltage range of the battery.

In some embodiments, a current collector layer having nickel flakes can comprise a composition to facilitate improved interaction with an electrode layer, such as to reduce an electrical resistance at or near the interface. For example, a current collector layer can have an amount of an electrically conductive carbon additive configured to facilitate improved contact between the current collect layer and an electrode layer. The electrically conductive carbon additive can include for example graphene. For example, a current collector layer having nickel flakes can comprise an amount of graphene configured to facilitate adhesion of the current collector layer to the electrode layer, and/or provide a well-blended interface with an electrode layer so as to improve contact between the two layers.

In some embodiments, a current collector layer comprising nickel flakes can demonstrate a desired roughness value. A current collector layer having an increased roughness value can advantageously facilitate improved wetting of the current collector layer by an electrode layer ink, for example facilitating adhesion of the current collector layer to the electrode layer. A current collector having an increased roughness value may advantageously facilitate increased surface area in contact with the electrode layer, for example decreasing an electrical resistance in the connection between the current collector layer and the electrode layer. For example, a current collector comprising nickel flakes can be provided with a roughness of about 5 ($\mu$m) microns to about 12 microns, including about 5 microns to about 7 microns, including about 5 microns. Roughness measurements can be performed according to various methods know to those skilled in the art, including for example, a contact profilometer (e.g., a profilometer which contacts a nickel film surface with a stylus to measure a roughness of the nickel film surface) and/or non-contact profilometer (e.g., an optical profilometer).

In some embodiments, the nickel flakes can have a thickness of about 0.5 microns ($\mu$m) to about 2 microns. In some embodiments, the nickel flakes can have a diameter of about 5 microns ($\mu$m) to about 30 microns, including about 20 microns. The term "diameter" is a conventional measure of the larger transverse dimensions (compared to thickness) of the nickel flakes and is not an indication of round shape. An increase in a diameter of the nickel flakes can facilitate increased roughness of the current collector printed using the nickel flakes. In some embodiments, a current collector layer printed using the nickel flakes can have a thickness of about 10 microns ($\mu$m) to about 40 microns, including about 20 microns.

In some embodiments, a current collector comprising nickel flakes can be suitable for a battery operating in a voltage range of about −1.7 Volts (V) to +1.7 Volts, including or example a zinc manganese dioxide battery.

Silver (Ag) current collectors, copper (Cu) current collectors, and/or stainless steel current collectors can be unsuitable for use in a battery, for example due to chemical and/or electrochemical reactivity with another component of the battery (e.g., reactivity with an electrolyte of the battery comprising ionic liquid), and/or to oxidation. In some embodiments, a current collector comprising nickel flakes can demonstrate increased electrical conductivity relative to a current collector comprising a carbon foil and/or a carbon based film (e.g., a carbon based film printed from a carbon based ink).

Example compositions are listed for an ink which can be used to print a current collector layer (e.g., to print the current collector layer 121), by weight %, such as to print an anode current collector layer and/or a cathode current collector layer of a zinc manganese dioxide battery:

- Nickel (Ni) flakes—about 50% to about 55%
- Graphene—about 1% to about 2%
- Glutaric acid—about 5% to about 7%
- Ethylene glycol—about 18% to about 20%
- Benzoyl peroxide—about 1% to about 10%
- Stearin—about 5% to about 10%
- Cyclohexanol—about 0.5% to about 3%
- Dimer diamine—about 1% to about 5%

An example procedure for preparing the ink which can be used to print a current collector layer can include combining components of the ink, and thoroughly mixing the components at a temperature of about 80° C. to about 120° C., for example to form an ink slurry. In some embodiments, the glutaric acid and the ethylene glycol can react to form a polyester in-situ. For example, the polyester can be formed during the mixing of the components of the ink. Components of the ink can be mixed for a duration of about 0.5 hours to about 1.5 hours.

A current collector ink can be deposited on a substrate and subsequently dried using infrared radiation (IR). In some embodiments, the printed ink can be dried at a temperature of about 280° F. to about 290° F. An example of a deposition process can include screen printing through a polyester screen having a mesh size of about 110 (e.g., a screen having 110 threads crossing per square inch of the screen). The printed ink can be dried in a forced air oven for a duration of about 10 minutes to about 15 minutes, at a temperature between about 280° F. to about 290° F.

Additional examples of embodiments of a nickel-containing films and/or methods of preparing the nickel-containing films are provided in pages 28-43 of PCT Patent Application No. PCT/US2013/078059, filed Dec. 27, 2013, the disclosure of which is incorporated herein by reference in its entirety.

Electrode Layers

In some embodiments, one or more electrode layers of a battery can comprise an ionic liquid. For example, both a cathode electrode layer and an anode electrode layer can comprise ionic liquid. In some embodiments, the ionic liquid can surround all or substantially surround all particles of an electrode layer. An electrode layer comprising an ionic liquid surrounding all or substantially surrounding all particles of the electrode layer may advantageously facilitate improved printability of the electrode layer ink, for example due to better wetting of the layer upon which the electrode layer is printed, and/or provide improved ionic transport within the electrode layer. In some embodiments, inclusion of ionic liquid in the electrode layer can facilitate enhanced rheology characteristics of the electrode layer ink. Ionic liquid may not evaporate during printing, and/or during storage (e.g., including storage in dry and/or inert atmosphere), remaining within the electrode layer, for example facilitating a stable electrode layer during printing and/or storage of the battery. In some embodiments, the ionic liquid can provide electrolyte species for electrochemical processes of the battery.

In some embodiments, an electrode layer can comprise a composition to facilitate improved interaction with an adjacent current collector layer, such as to reduce an electrical resistance at or near the interface between the two layers. For example, an electrode layer can have an amount of an electrically conductive carbon additive configured to facilitate improved contact between an adjacent current collect layer and the electrode layer. The electrically conductive carbon additive can include, for example, graphite, carbon nanotubes (e.g., single and/or multi-wall carbon nanotubes), graphene, combinations thereof, and/or the like. For example, an electrode layer can comprise an amount of graphite and/or carbon nanotubes configured to facilitate adhesion of a current collector layer to the electrode layer, and/or provide a well-blended interface with the current collector layer so as to improve contact between the two layers.

Example Compositions of a Cathode Electrode Layer

A cathode electrode layer can include electrically conductive carbon additives, for example to facilitate increased electrical conductivity within the cathode, and/or increased interaction with an adjacent current collector layer. Suitable electrically conductive carbon additives can include any of a number of electrically conductive forms of carbon. For example, an electrically conductive carbon additive can comprise graphene, graphite, carbon nanotubes (e.g., single wall carbon nanotubes, and/or multi-wall carbon nanotubes), combinations thereof, and/or the like. In some embodiments, an electrode layer for a cathode can include multi-wall carbon nanotubes and graphite. In some embodiments, multi-wall carbon nanotubes can facilitate dispersion of ionic liquid within the cathode, for example, reducing or preventing or substantially preventing accumulation of ionic liquid within the cathode in any one area.

Example compositions are listed for an ink which can be used to print a cathode electrode layer, in weight %, such as for a cathode of a zinc manganese dioxide battery:

- High molecular weight polyvinylidene difluoride polymer (PVDF HSV)—about 1% to about 5%, including about 2%
- $MnO_2$—greater than about 20%, including about 37%
- Graphite C65—about 0.5% to about 5%, including about 1%
- Multi-wall carbon nanotubes (MWCNTs)—about 0.2% to about 5%, including about 0.5%
- 1-ethyl-3-methylimidazolium tetrafluoroborate ($C_2mimBF_4$)—about 1% to about 3%, including about 2%
- 1-methyl-2-pyrrolidinone (MP)—about 50% to about 70%, including about 59%

In one embodiment, the electrode layer can be printed using a polyester mesh having a mesh size of about 110. Subsequently, the printed ink can be dried, for example, at a temperature of about 250° F. to about 300° F. for a duration of about 5 minutes to about 10 minutes (e.g., dried in a forced air oven using an infrared radiation (IR) technique).

Example compositions are listed for a printed cathode electrode layer, in weight %, such as a cathode of a zinc manganese dioxide battery:

- PVDF HSV—about 3% to about 7%, including about 5%
- $MnO_2$—greater than about 50%, including about 87%
- Conductive graphite—about 1% to about 12%, including about 2.5%
- MWCNTs—about 0.5% to about 12%, including about 1%
- 1-ethyl-3-methylimidazolium tetrafluoroborate ($C_2mimBF_4$)—about 2% to about 7%, including about 4.5%

Example Compositions of an Anode Electrode Layer

Use of an electrically conductive carbon additive in a battery anode electrode layer was found to advantageously facilitate significant improvement in electrochemical performance of the battery. For example, addition of a conductive carbon additive to an anode electrode layer of a zinc manganese dioxide battery can significantly improve a capacity performance of the zinc manganese dioxide battery. Suitable electrically conductive carbon additives can include any of a number of electrically conductive forms of carbon. For example, an electrically conductive carbon additive can comprise graphene, graphite, carbon nanotubes (e.g., single wall carbon nanotubes, and/or multi-wall carbon nanotubes), combinations thereof, and/or the like. In some embodiments, use of a conductive carbon material in an anode electrode layer may facilitate improved electrical conductivity of the anode (e.g., in addition to electrical conductivity provide by Zn powder), improved ink rheology and/or printability, and/or improved interfacial contact between an adjacent current collector layer and the anode electrode layer. In some embodiments, a current collector layer comprising a carbon material (e.g., a current collector comprising nickel flakes and a carbon material) may be particularly suitable for use with an anode comprising a conductive carbon material. Without being limited by any particular theory and/or mode of operation, adjacent layers comprising similar components (e.g., carbon of the electrode layer and carbon of the current collector layer) may facilitate interaction at the interface between the electrode layer and current collector layer, for example reducing an electrical resistance at the interface.

Example compositions are listed for an ink which can be used to print an anode electrode layer, in weight %, such as for an anode of a zinc manganese dioxide battery:

- Zinc powder—greater than about 60%, including about 72%
- Tetramethyl urea—about 20% to about 35%, including about 25%
- Conductive graphite—about 0.3% to about 4%, including about 1%
- PVDF HSV—about 0.2% to about 4%, including about 0.5%
- 1-ethyl-3-methylimidazolium tetrafluoroborate ($C_2mimBF_4$)—about 0.5% to about 4%, including about 1.4%
- Zinc tetrafluoroborate ($Zn(BF_4)_2$)—about 0.05% to about 0.4%, including about 0.1%

In one embodiment, the electrode layer can be printed using a polyester mesh having a mesh size of about 110. Subsequently, the printed ink can be dried, for example at a temperature of about 250° F. to about 300° F. for a duration of about 3 minutes to about 5 minutes (e.g., dried in a forced air oven using an infrared radiation (IR) technique).

Example compositions are listed for a printed anode electrode layer, in weight %, such as for an anode of a zinc manganese dioxide battery:

- PVDF HSV—about 0.3% to about 5%, including about 0.6%
- 1-ethyl-3-methylimidazolium tetrafluoroborate ($C_2mimBF_4$)—about 1% to about 5%, including about 2%
- Zinc powder—greater than about 80%, including about 96%
- Conductive graphite—about 0.5% to about 5%, including about 1.2%
- Zinc tetrafluoroborate ($Zn(BF_4)_2$)—about 0.1% to about 0.5%, including about 0.2%

As described herein, various other processes can be used to deposit the ink for one or more layers of the battery, including various printing techniques.

Figure 13:
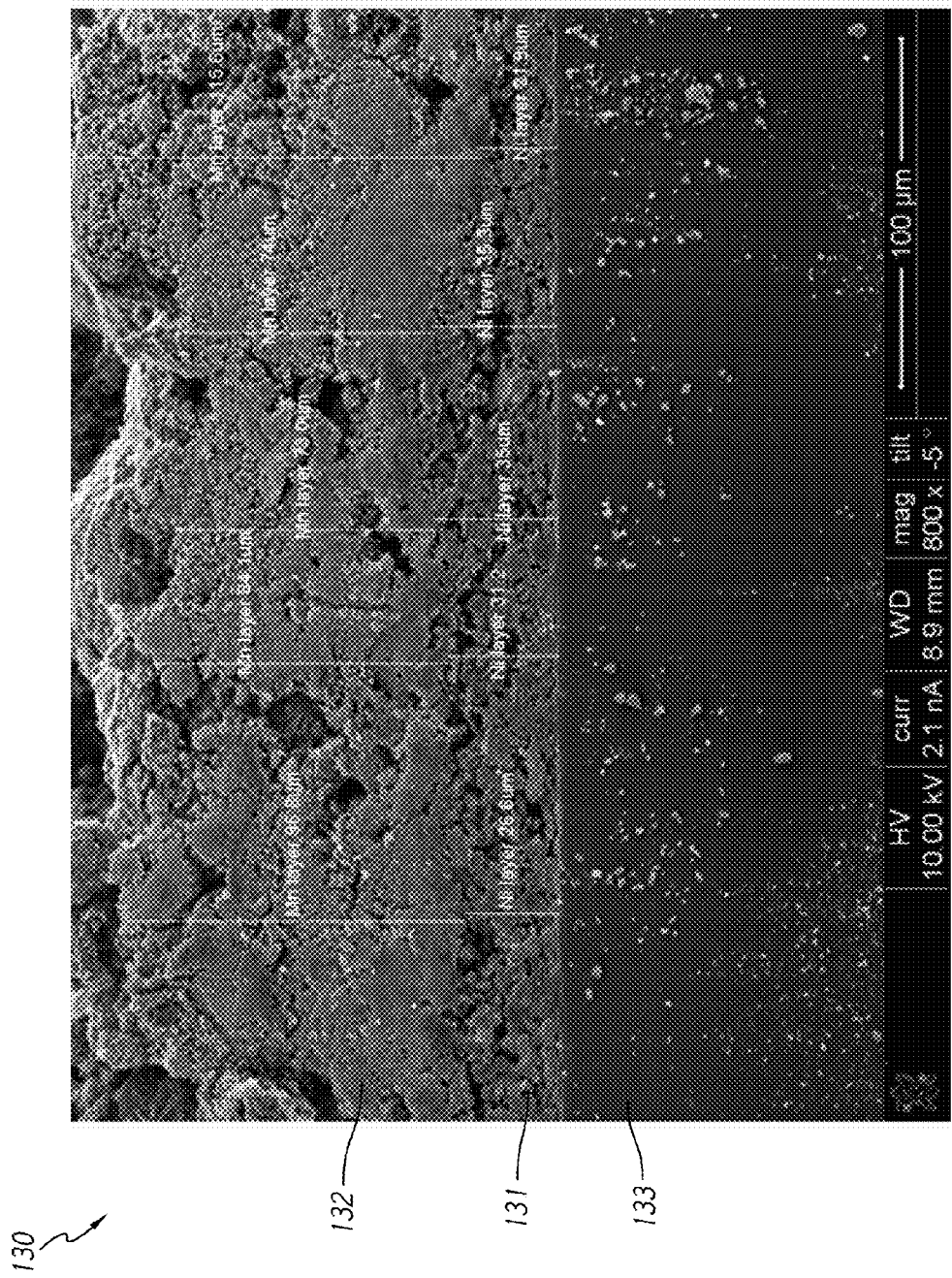
FIG. 13 is an SEM image of a cross section of an example embodiment of a cathode and a current collector of a battery.

Referring to FIG. 13, a scanning electron microscope (SEM) image at 800× magnification is shown of a portion of a battery 130, in the illustrated example a zinc manganese dioxide battery. The SEM sample may be prepared by imaging the SEM sample after placing the SEM sample in liquid nitrogen ($N_2$). A cathode electrode layer 132 of the battery 130 is shown as being printed over a current collector layer 131, and the current collector layer 131 is shown as being printed over a substrate 133. In FIG. 13, the current collector layer 131 is labeled using "Ni" and the cathode electrode layer 132 is labeled using "Mn." The substrate 133 comprises Mylar™ (a polyester material). As shown in FIG. 13, the printed current collector layer 131 has a thickness of about 26 microns to about 38 microns, and the printed cathode electrode layer 132 has a thickness of about 83 microns to about 93 microns.

Figure 14:
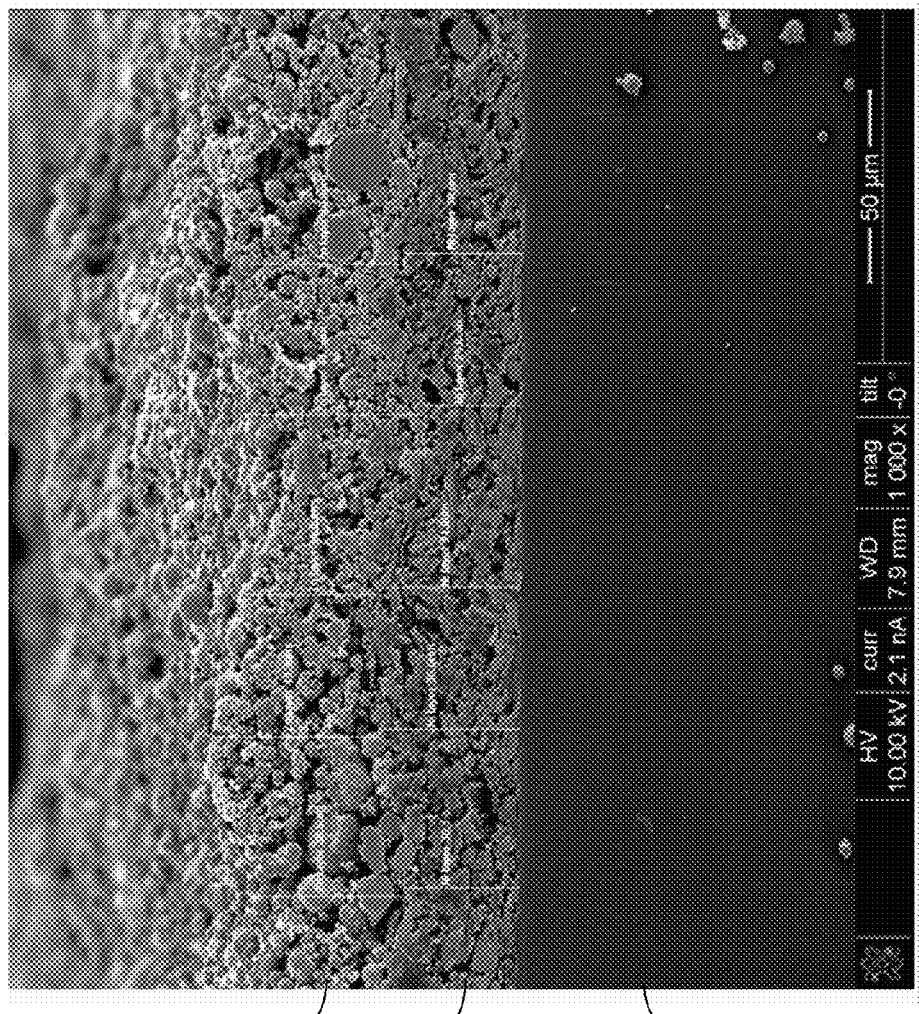
FIG. 14 is an SEM image of a cross section of an example embodiment of an anode and a current collector of a battery.

Referring to FIG. 14, a scanning electron microscope (SEM) image at 1,000× magnification is shown of a portion of a battery 140, in the illustrated example a zinc manganese dioxide battery. The SEM sample may be prepared by imaging the SEM sample after placing the SEM sample in liquid nitrogen ($N_2$). An anode electrode layer 142 of the battery 140 is shown as being printed over a current collector layer 141, and the current collector layer 141 is shown as being printed over a substrate 143. The anode electrode layer 142 is labeled using "Zn" and the current collector layer 141 is labeled using "Ni." The substrate 143 comprises Mylar (a polyester material). As shown in FIG. 14, the printed current collector layer 141 has a thickness of about 26 microns to about 38 microns and the printed anode electrode layer 142 have a thickness of about 35 microns to about 45 microns after one screen print cycle for each layer using a polyester mesh having a size of about 110.

The portion of the battery 130 in FIG. 13 and the portion of the battery 140 in FIG. 14 were printed as a square having a length of about 0.5 inches on each side, using a polyester mesh having a mesh size of about 110 such that the cathode electrode layer 132 has about 0.03 grams (g) of Mn (e.g., after two to three printing cycles) and the anode electrode layer 142 has about 0.015 grams of Zn (e.g., after one printing cycle). As shown in FIGS. 13 and 14, an interface between the cathode electrode layer 132 of and/or the anode electrode layer 142, and the current collector layers 131, 141, respectively, can be well-blended. The well-blended interface (e.g., no or substantially no gaps can be seen between the two layers in the SEM images) may indicate improved interaction at the interface between the two layers, facilitating improved adhesion of the two layers and/or increased surface area in contact between the two layers, providing for example reduced electrical resistance at or near the interface.

Details of Battery Performance

Figure 15:
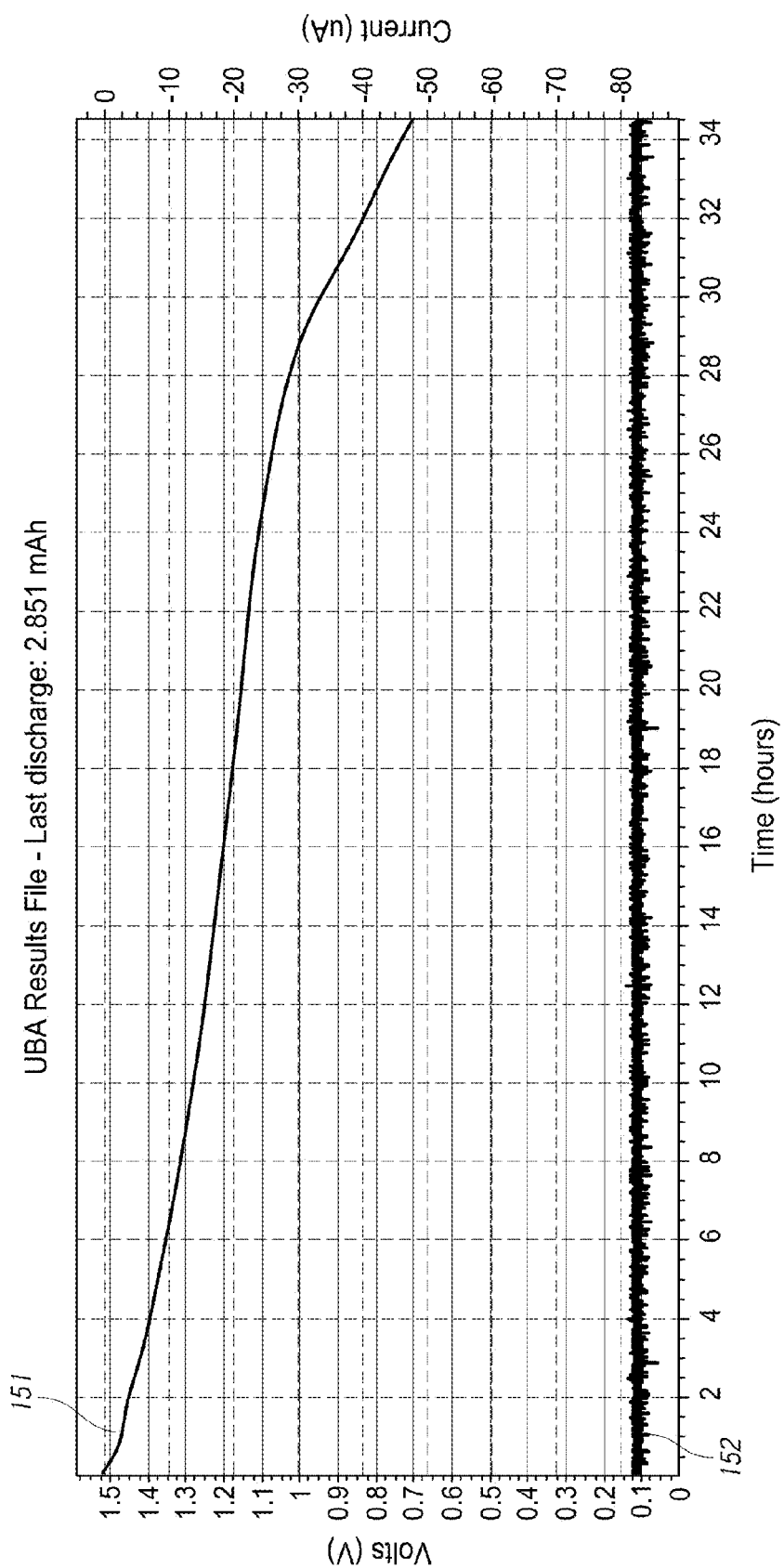
FIG. 15 is a graph of battery potential versus time of discharge for an example battery.
Figure 16:
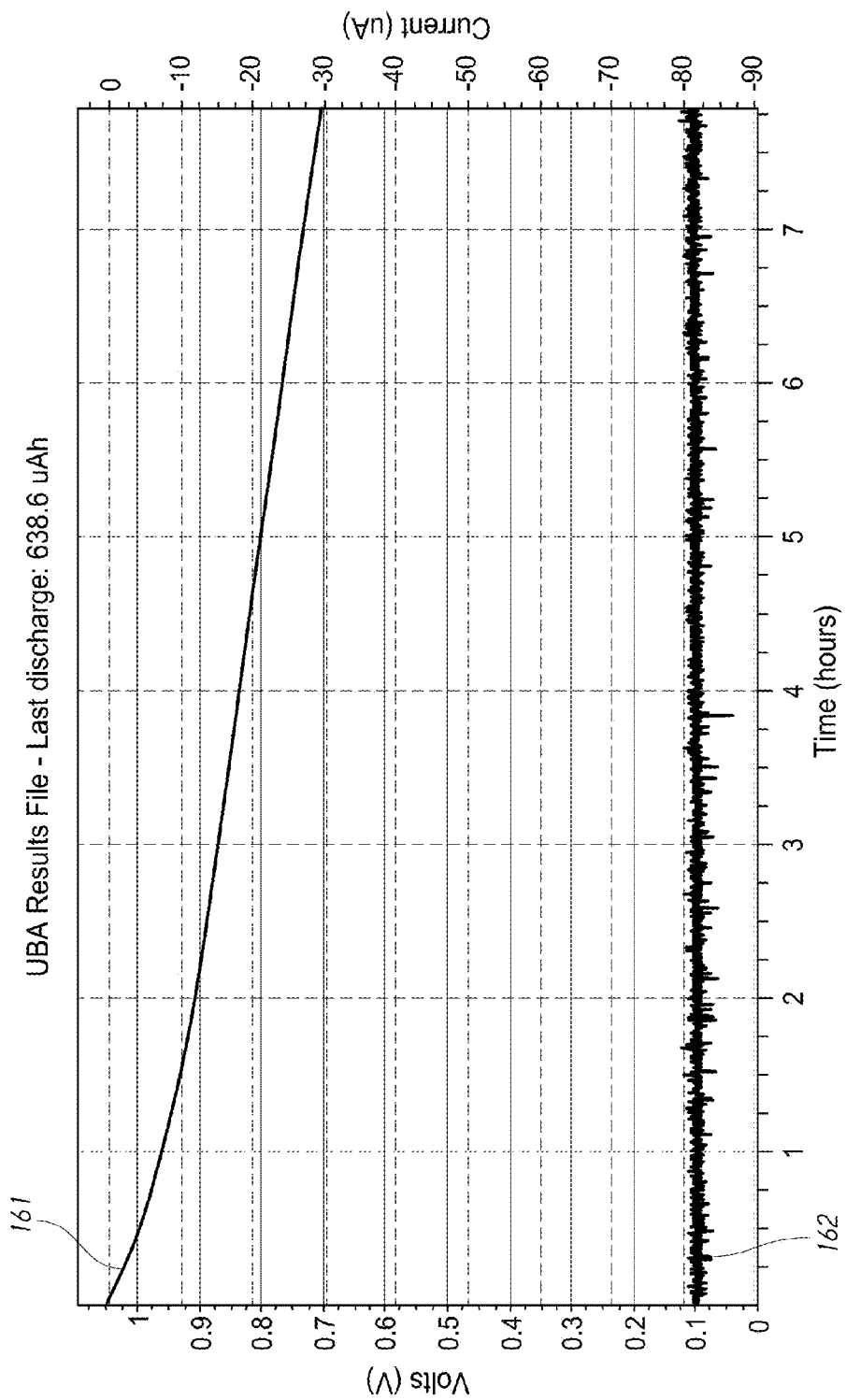
FIG. 16 is a graph of battery potential versus time of discharge for another example battery.
Figure 17:
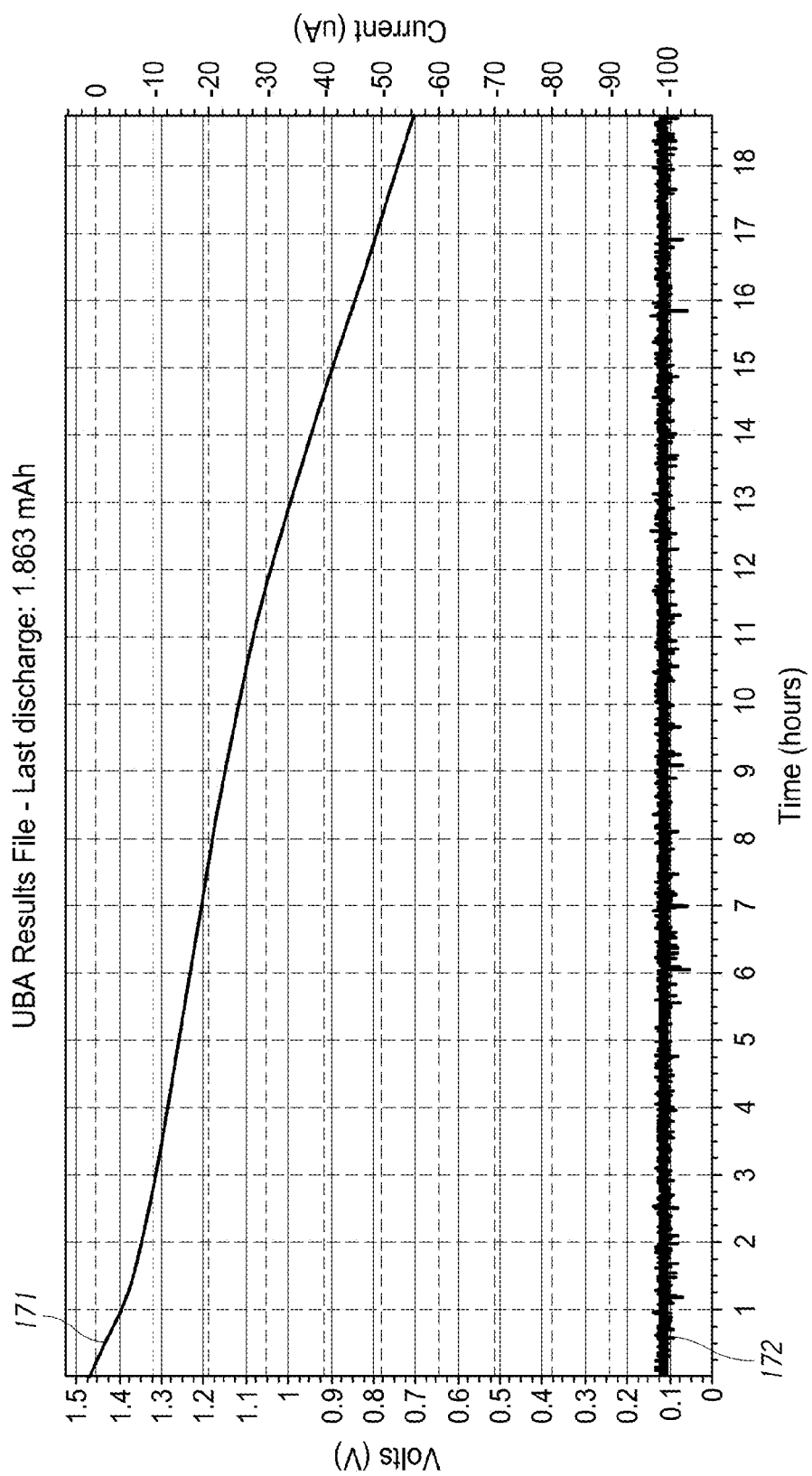
FIG. 17 is a graph of battery potential versus time of discharge for another example battery.

FIGS. 15 through 17 show battery discharge graphs of three zinc manganese dioxide batteries having different current collectors. Each battery can have a square or substantially square shape, where each side of each of the batteries has a length of about 0.5 inches (in). Each of the batteries tested in FIGS. 15 through 17 included electrode layers having a composition and fabricated according to embodiments as described herein. Each of the batteries had a printed cathode electrode layer and printed anode electrode layer. Each of the batteries had screen printed electrode layers, each printed layer being printed using polyester mesh having a mesh size of about 110. The printed electrode layers were dried at a temperature of about 250° F. to about 300° F. for about 5 minutes to about 10 minutes. Each of the batteries of FIGS. 15 through 17 included a polypropylene based separator coated with a surfactant material having a thickness of about 25 microns (e.g., Celgard®, available from Celgard LLC of Charlotte, N.C.). The separator was presoaked in an electrolyte comprising a concentration of about 1 mol/L (M) zinc tetrafluoroborate ($Zn(BF_4)_2$) in 1-ethyl-3-methylimidazolium tetrafluoroborate ($C_2mimBF_4$), and subsequently sandwiched between the cathode and the anode of the battery. A cathode and anode of each battery graphed in FIGS. 15 through 17 had the same or substantially the same composition. For example, each of the anode electrode layers comprised about 0.015 grams (g) zinc powder, and each of the cathode electrode layers comprised about 0.03 g $MnO_2$ (e.g., each battery including an excess amount of zinc such that electrochemical processes of each battery being limited by the amount of $MnO_2$ in the battery). The conditions of discharge for each of the batteries of FIGS. 15 through 17 were the same or substantially the same (e.g., a discharge current of about 0.08 milliamperes (mA) to about 0.10 mA, for example about 0.09 mA).

FIG. 15 shows a battery potential performance in a constant current discharge of a battery including electrode layers and a separator as described herein, and where current collectors of the battery comprise nickel flakes as described herein. For example, the current collectors of the battery had a thickness of about 26 microns to about 32 microns, and a sheet resistance of about 0.6 Ohm/sq/mil to about 1.0 Ohm/sq/mil. The current collectors had a roughness of about 6 microns to about 8 microns.

Referring to FIG. 15, graph 151, with reference to the y-axis labeled with voltage in Volts (V), is a graph of battery potential versus time for discharge of an example battery including the layers as described herein. Graph 152 of FIG. 15, with references to the y-axis labeled with of current in microamperes (µA), shows that the battery was discharged at a constant current of about 0.09 milliAmperes (mA). Measurements were performed on Vencon UBA5 Battery Analyzer (e.g., available from Vencon Technologies, Inc., of Ontario, Canada). The battery of FIG. 15 was discharged with the current of about 0.09 (mA) and lasted about 34.5 hours. The cut-off voltage for the calculations was 700 millivolts (mV). The capacity of the $Zn/MnO_2$ battery was about 2.851 milliampere-hour (mAh). The open circuit potential of the battery was 1.54 Volts (V).

FIG. 16 shows a battery potential performance in a constant current discharge of a battery including electrode layers and a separator as described herein, and where current collectors of the battery were printed using commercially available nickel ink. The commercially available nickel ink can have a composition as listed below, in weight % (e.g., CI-5001, available from Engineered Conductive Materials, LLC, of Delaware, Ohio):

Ni flake—40% to 50%.
Carbon black—less than 5%.

The commercially available nickel ink can be dried in 10 minutes under a temperature of 230° F. The dried film can have a thickness of 10 microns to 17 microns. A nickel current collector can be printed using a polyester and/or stainless steel (SS) mesh having a size of 173 to 381 threads per inch. The printed film using the commercially available nickel ink can have a sheet resistance of less than 5 ohms/square/mil.

The battery tested in FIG. 16 includes current collectors screen printed using the commercially available nickel ink using a mesh having a size of about 180 and dried for about 10 minutes at a temperature of about 250° F. A sheet resistance of the printed and dried film using the commercially available nickel ink was about 3 Ohm/sq/mil. A thickness of the dried film ranged from about 8 microns to about 12 microns. The dried film had a roughness of about 1.5 microns to about 2.5 microns.

Referring to FIG. 16, graph 161, with reference to the y-axis labeled with voltage in Volts (V), is a graph of battery potential versus time for discharge of an example battery including the electrode layers as described herein and current collectors printed using commercially available nickel ink. Graph 162 of FIG. 16, with references to the y-axis labeled with of current in microamperes (µA), shows that the battery was discharged at a constant current of about 0.09 milliAmperes (mA). Measurements were performed on Vencon UBA5 Battery Analyzer. The battery of FIG. 16 was discharged with the current of about 0.09 (mA) and lasted about 8 hours. The cut-off voltage for the calculations was 700 millivolts (mV). The capacity of the $Zn/MnO_2$ battery is about 638.6 microampere-hour (μAh). The open circuit potential of the battery is 1.2 Volts (V).

FIG. 17 shows a battery potential performance in a constant current discharge of a battery including electrode layers and a separator as described herein, and where current collectors of the battery comprise aluminum (Al) foil. The aluminum foil was abraded with a sand paper and washed with acetone and alcohol to facilitate removal of oil contaminates and/or improve adhesion of inks to the Al foil.

Referring to FIG. 17, graph 171, with reference to the y-axis labeled with voltage in Volts (V), is a graph of battery potential versus time for discharge of an example battery including the electrode layers as described herein and current collectors comprising aluminum foils. Graph 172 of FIG. 17, with references to the y-axis labeled with of current in microamperes (μA), shows that the battery was discharged at a constant current of about 0.09 milliAmperes (mA). Measurements were performed on Vencon UBA5 Battery Analyzer. The battery of FIG. 17 was discharged with the current of about 0.09 (mA) and lasted about 19 hours. The cut-off voltage for the calculations was 700 millivolts (mV). The capacity of the $Zn/MnO_2$ battery was about 1.863 milliampere-hour (mAh). The open circuit potential of the battery was about 1.52 Volts (V).

As shown in FIGS. 15 through 17, the battery comprising printed nickel current collectors using nickel ink having a composition according to one or more embodiments described herein can demonstrate increased capacity performance and/or decreased resistance. As described herein, the initial open circuit voltage of the battery comprising current collectors printed using nickel ink having a composition according to one or more embodiments described herein (e.g., the battery of FIG. 15) was about 1.54V, the initial open circuit voltage of the battery comprising current collectors printed using commercially available nickel ink (e.g., the battery of FIG. 16) was about 1.2V, and the initial open circuit voltage of the battery comprising Al foil current collectors (e.g., the battery of FIG. 17) was about 1.52V. Resistance of the batteries can be measured before discharging the batteries (e.g., using current interrupt and impedance techniques). The resistance of the battery of FIG. 15 was about 80 Ohms (Ω) to about 250 Ohms. The resistance of the battery of FIG. 16 was about 500 Ohms to about 800 Ohms, and the resistance of the battery of FIG. 17 was about 0.6 kilo-Ohms (kΩ) to about 1.1 kilo-Ohms. Without being limited by any particular theory or mode of operation, the reduced voltage and relatively higher resistance of the battery of FIG. 16 may be due to decreased adhesion of the electrode layers and/or reactivity of the current collector with the electrolyte of the battery.

Figure 18:
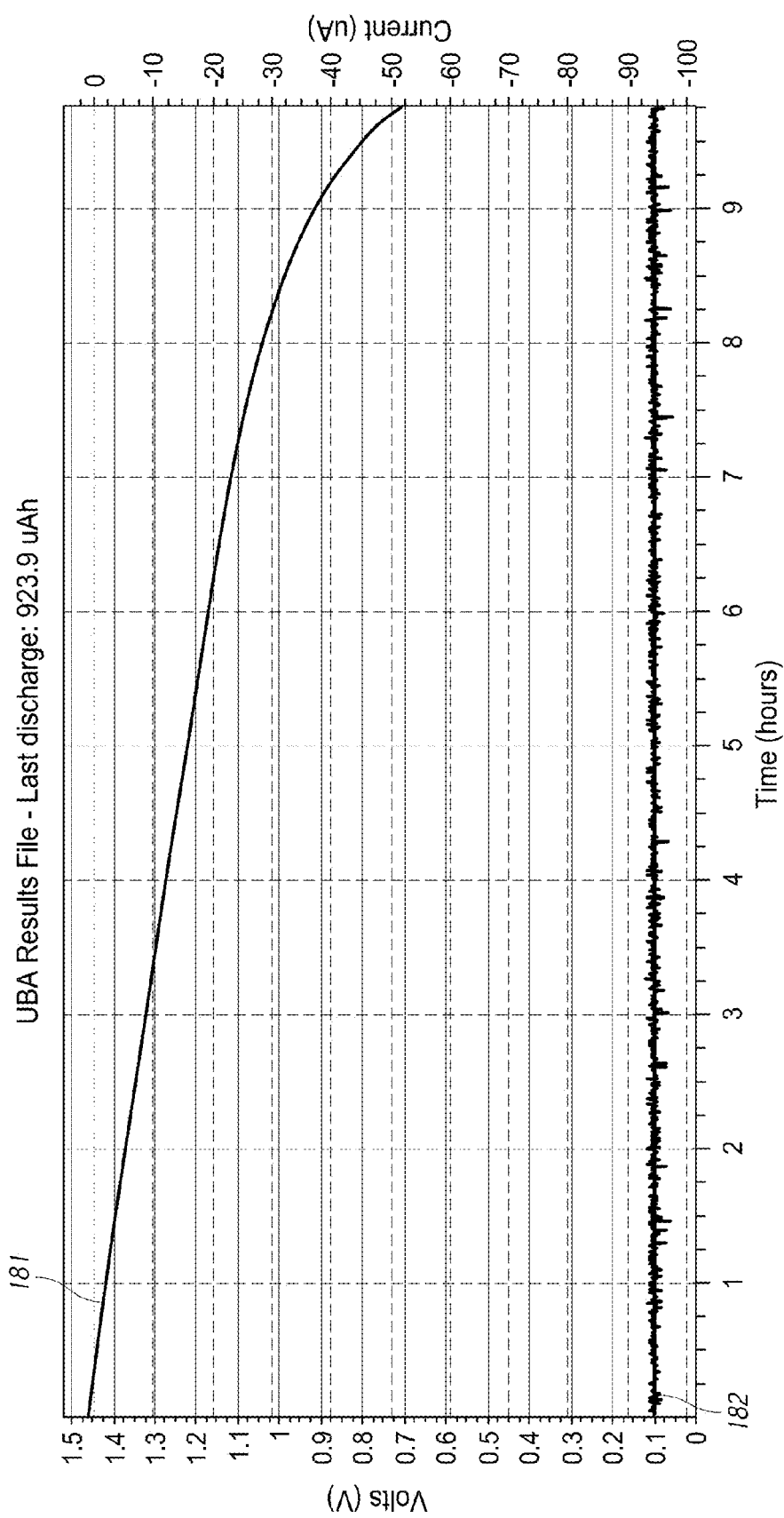
FIG. 18 is a graph of battery potential versus time of discharge for another example battery.
Figure 19:
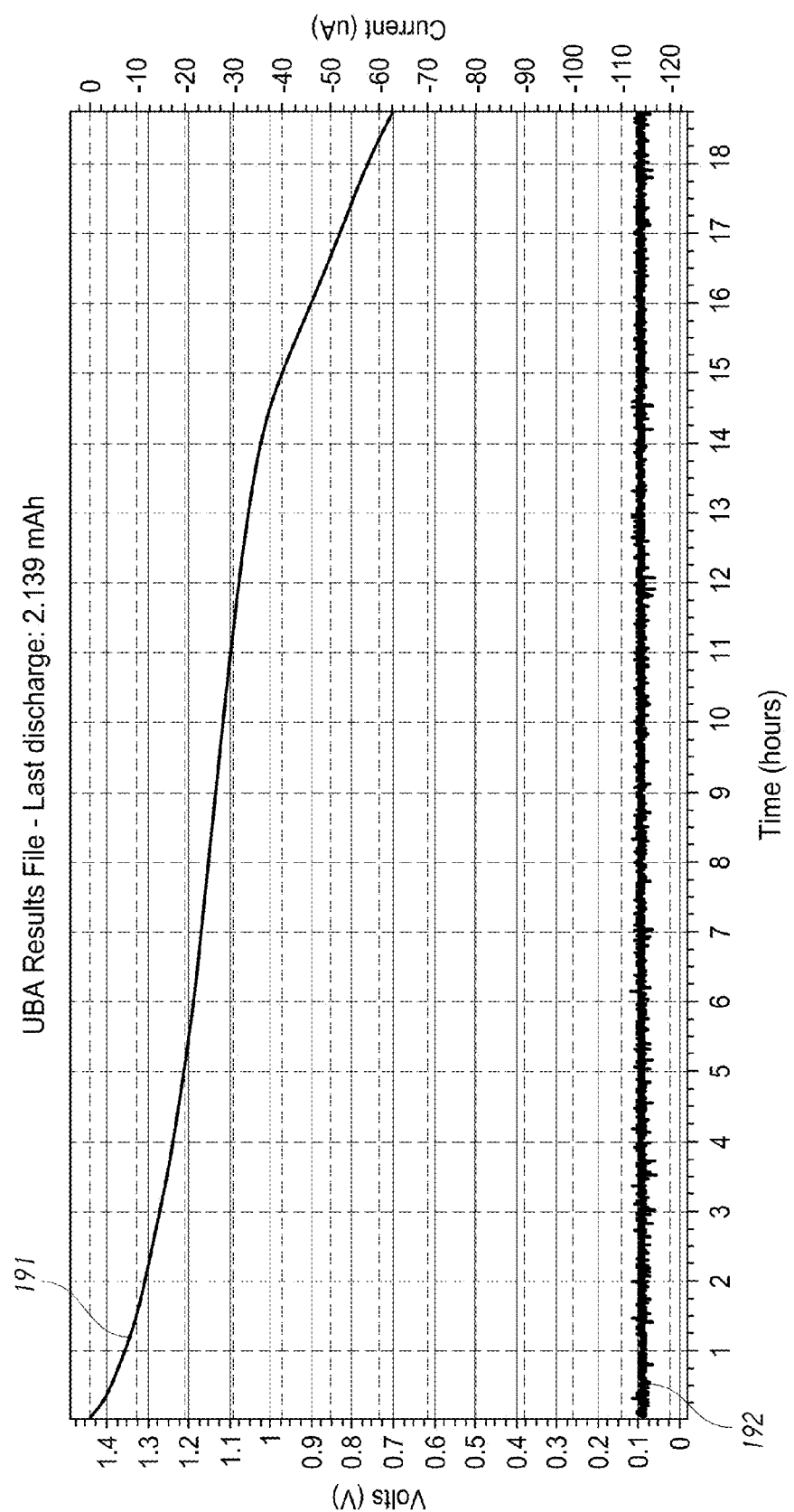
FIG. 19 is a graph of battery potential versus time of discharge for another example battery.
Figure 20:
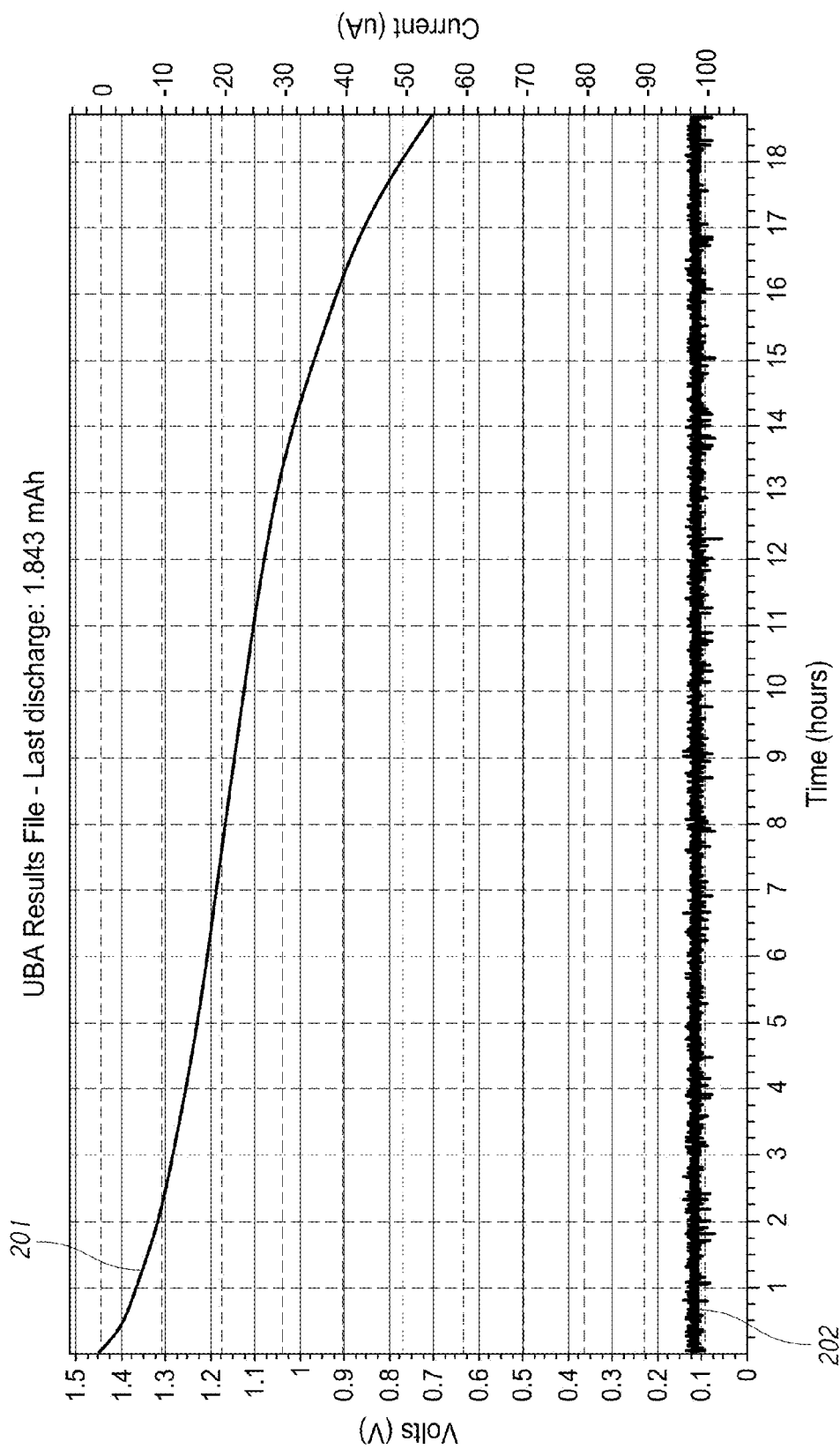
FIG. 20 is a graph of battery potential versus time of discharge for another example battery.

FIGS. 18 through 20 show battery discharge graphs of three zinc manganese dioxide batteries comprising varying amounts of electrically conductive carbon additive in their respective anode electrode layer, and/or different types of electrically conductive carbon additive in the anode electrode layer. Each of the batteries in FIGS. 18 through 20 was fabricated using current collectors printed from nickel ink described herein according to one or more embodiments, and included a cathode having a composition according to one or more embodiments described herein. Each battery had a square or substantially square shape, where each side of each of the batteries has a length of about 0.5 inches (in). Each of the batteries had screen printed electrode layers for the anode and the cathode and a printed anode current collector and a printed cathode current collector, the layers being printed using polyester mesh having a mesh size of about 110. The printed layers were dried at a temperature of about 250° F. to about 300° F. for about 5 minutes to about 15 minutes. Each of the batteries of FIGS. 18 through 20 included a polypropylene based separator coated with a surfactant material having a thickness of about 25 microns (e.g., Celgard®, available from Celgard LLC of Charlotte, N.C.). The separator was presoaked in an electrolyte comprising a concentration of about 1 mol/L (M) zinc tetrafluoroborate $(Zn(BF_4)_2)$ in 1-ethyl-3-methylimidazolium tetrafluoroborate $(C_2mimBF_4)$, and subsequently sandwiched between the cathode and the anode of the battery. The cathode and anode of each battery graphed in FIGS. 18 through 20 have the same or substantially the same quantity of $MnO_2$ and zinc. For example, each of the anodes comprised about 0.015 grams (g) zinc powder, and each of the cathodes comprised about 0.021 g $MnO_2$ (e.g., each battery including an excess amount of zinc such that electrochemical processes of each battery is limited by the amount of $MnO_2$ in the battery). The conditions of discharge for each of the batteries of FIGS. 18 through 20 were the same or substantially the same (e.g., a discharge current of about 0.08 milliamperes (mA) to about 0.10 mA, for example about 0.09 mA).

FIG. 18 shows a battery discharge graph of a battery comprising an anode electrode layer having no electrically conductive carbon additive. Referring to FIG. 18, graph 181, with reference to the y-axis labeled with voltage in Volts (V), is a graph of battery potential versus time for discharge of an example battery comprising an anode including no electrically conductive carbon additive. Graph 182 of FIG. 18, with reference to the y-axis labeled with of current in microamperes (μA), shows that the battery was discharged at a constant current of about 0.09 milliAmperes (mA). Measurements were performed on Vencon UBA5 Battery Analyzer. The battery of FIG. 18 was discharged with the current of about 0.09 (mA) and lasted about 10 hours. The cut-off voltage for the calculations was 700 milliVolts (mV). The capacity of the $Zn/MnO_2$ battery was about 923.9 microampere-hour (μAh). The open circuit potential of the battery was about 1.53 Volts (V). The measured resistance of the battery was about 600 Ohm.

FIG. 19 shows a battery discharge graph of a battery comprising an anode electrode layer having 0.6 weight % of graphite. Referring to FIG. 19, graph 191, with reference to the y-axis labeled with voltage in Volts (V), is a graph of battery potential versus time for discharge of an example battery including an anode comprising graphite. Graph 192 of FIG. 19, with reference to the y-axis labeled with of current in microamperes (μA), shows that the battery was discharged at a constant current of about 0.09 milliAmperes (mA). Measurements were performed on Vencon UBA5 Battery Analyzer. The battery of FIG. 19 was discharged with the current of about 0.09 (mA) and lasted about 19 hours. The cut-off voltage for the calculations was 700 milliVolts (mV). The capacity of the $Zn/MnO_2$ battery was about 2.139 milliampere-hour (mAh). The open circuit potential of the battery was about 1.51 Volts (V). The measured resistance of the battery was about 200 Ohm.

FIG. 20 shows a battery discharge graph of a battery comprising an anode electrode layer having 0.5 weight % of multiwall carbon nanotubes. Referring to FIG. 20, graph 201, with reference to the y-axis labeled with voltage in Volts (V), is a graph of battery potential versus time for discharge of an example battery including an anode comprising multi-walled carbon nanotubes. Graph 202 of FIG. 20, with reference to the y-axis labeled with of current in microamperes (μA), shows that the battery was discharged at a constant current of about 0.09 milliAmperes (mA). Measurements were performed on Vencon UBA5 Battery Analyzer. The battery of FIG. 20 was discharged with the current of about 0.09 (mA) and lasted about 19 hours. The cut-off voltage for the calculations was 700 millivolts (mV). The capacity of the $Zn/MnO_2$ battery was about 1.843 milliampere-hour (mAh). The open circuit potential of the battery was about 1.500 Volts (V). The measured resistance of the battery was about 300 Ohms.

As shown in FIGS. 18 through 20, zinc manganese dioxide batteries which included an anode comprising a conductive carbon additive can advantageously demonstrate increased capacity and/or reduced resistance. For example, a battery capacity can be approximately doubled with addition of less than 1 weight % conductive carbon additive to the anode electrode layer. For example, a battery resistance can be reduced by about half to about two-thirds with addition of less than 1 weight % conductive carbon additive.

Formation of Electrode Layers for a 0.5 Inch by 0.5 Inch Battery

The stoichiometric mass ratio between Zn of an anode of a zinc manganese dioxide battery and $MnO_2$ of a cathode of the battery can be about 1:2.66 $Zn:MnO_2$. For example, the battery cathode can include 2.66 times more $MnO_2$ than the Zn (by mass) of the anode such that both Zn and $MnO_2$ can be consumed completely or substantially completely during operation of the battery.

In some embodiments, one screen printing cycle for an electrode layer of an anode (e.g., anode having a square shape, and lengths of about 0.5 inches) using a polyester mesh having a mesh size of about 110 can provide an electrode layer comprising about 0.010 grams (g) to about 0.020 g of zinc. To fabricate a battery having a cathode made of an amount of $MnO_2$ in which all or substantially all of the zinc and $MnO_2$ can be consumed, can comprise printing a cathode having about 0.027 grams (g) to about 0.054 g of $MnO_2$. In some embodiments, one screen printing cycle for an electrode layer of a cathode (e.g., cathode having a square shape, and lengths of about 0.5 inches) using a polyester mesh having a mesh size of about 110 can provide an electrode layer comprising about 0.009 grams (g) to about 0.015 g $MnO_2$. For example, to achieve a desired cathode thickness, two to three screen printing cycles can be performed. Of course, mesh size can be selected to facilitate printing thicker or thinner electrode layers.

Figure 21:
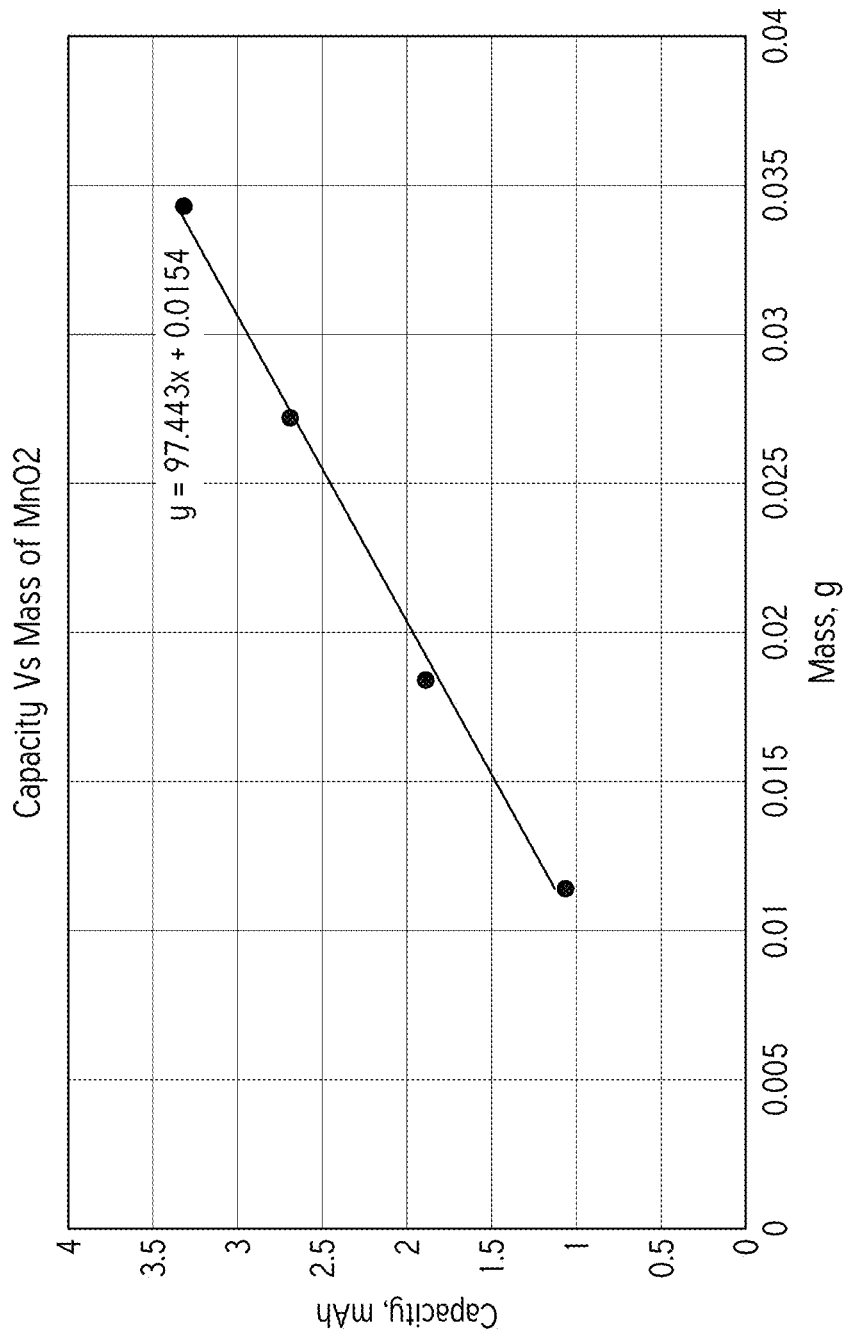
FIG. 21 is a graph of capacity performance of an example battery as it relates to a mass of a cathode active material.

FIG. 21 shows a graph of battery capacity performance, expressed in milliampere-hour (mAh), versus a mass of $MnO_2$ of the cathode, expressed in grams (g), when Zn of the anode is in excess so that zinc is not the limiting component. The batteries were fabricated using a nickel ink according to one or more embodiments as described herein, and were fabricated as 0.5 inch by 0.5 inch squares. The batteries were printed using a stencil printing technique (e.g., using a stainless steel foil having a thickness of about 125 microns). The batteries were prepared using anodes having about 0.015 grams (g) of zinc. The batteries were discharged at a constant or substantially constant current, such as at about 0.08 milliamperes (mA) to about 0.10 mA, for example at about 0.09 mA. As shown in FIG. 21, the capacity performance increases as the amount of the cathode $MnO_2$ increased since the batteries in FIG. 21 include an excess amount of zinc.

Printing

The final composition of the layers may be formed after printing a corresponding ink and drying (curing) the layer at least a certain temperature for at least a certain time.

Inks generally have all the components of the corresponding layers plus one or more water soluble, and/or organic solvents. The solvents can be used to dissolve polymers (e.g., acting as solvents) and/or to create a suitable viscosity for printing of the inks (e.g., acting as viscosity modifiers) that evaporate during the drying process.

The fully or partially printed zinc manganese dioxide battery can be printed on any flexible or rigid substrate that is conductive or non-conductive. Choice of water soluble and/or organic solvents often depends on the ability of the solvent to wet substrates (e.g., acting as wetting agents). In some embodiments, a printing ink comprises a second solvent to provide increased wettability of the substrate.

In some embodiments, the printing ink is suitable for a screen printing process. The printing ink may also be suitable for other printing processes.

LIST OF EXAMPLE ALTERNATIVE COMPONENTS AND TECHNIQUES

Polymers

Suitable polymers for one or more layers of the printed battery 10, or a printed battery 70, include, but are not limited to: (or equivalently, polymeric precursors or polymerizable precursors) such as polyvinyl pyrrolidone (PVP), polyvinyl alcohol (PVA), polyvinylidene fluoride, polyvynylidene fluoride-trifluoroethylene, polytetrafluoroethylene (PTFE), polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and/or chitosan.

In some embodiments, a suitable polymer may be electrostable under a working voltage of a battery. A $Zn/MnO_2$ battery has relatively low voltage, so many polymers may be suitable. For example, fluorinated polymers may be suitable due to their chemical, thermo, and electrochemical stability.

The insulator layer 7, or the insulator layer 76, may include a polymer that does not allow penetration by oxygen and/or water into the battery. A variety of PVDF or polyolefins can be used as barrier layer polymers for both water and oxygen. A combination of an oxygen barrier polymer and a moisture barrier polymer from the list above is also possible.

Solvents

Suitable solvents used in preparing one or more inks for fabricating a printed battery 10, a printed battery 70, a printed battery 80, etc., include, but are not limited to: water, alcohols such as methanol, ethanol, N-propanol (including 1-propanol, 2-propanol (isopropanol or IPA), 1-methoxy-2-propanol), butanol (including 1-butanol, 2-butanol (isobutanol)), pentanol (including 1-pentanol, 2-pentanol, 3-pentanol), hexanol (including 1-hexanol, 2-hexanol, 3-hexanol), octanol, N-octanol (including 1-octanol, 2-octanol, 3-octanol), tetrahydrofurfuryl alcohol (THFA), cyclohexanol, cyclopentanol, terpineol; lactones such as butyl lactone; ethers such as methyl ethyl ether, diethyl ether, ethyl propyl ether, and polyethers; ketones, including diketones and cyclic ketones, such as cyclohexanone, cyclopentanone, cycloheptanone, cyclooctanone, acetone, benzophenone, acetylacetone, acetophenone, cyclopropanone, isophorone, methyl ethyl ketone; esters such ethyl acetate, dimethyl adipate, proplyene glycol monomethyl ether acetate, dimethyl glutarate, dimethyl succinate, glycerin acetate, carboxylates; carbonates such as propylene carbonate; polyols (or liquid polyols), glycerols and other polymeric polyols or glycols such as glycerin, diol, triol, tetraol, pentaol, ethylene glycols, diethylene glycols, polyethylene glycols, propylene glycols, dipropylene glycols, glycol ethers, glycol ether acetates 1,4-butanediol, 1,2-butanediol, 2,3-butanediol, 1,3-propanediol, 1,4-butanediol, 1,5-pentanediol, 1,8-octanediol, 1,2-propanediol, 1,3-butanediol, 1,2-pentanediol, etohexadiol, p-menthane-3,8-diol, 2-methyl-2,4-pentanediol; tetramethyl urea, n-methylpyrrolidone, acetonitrile, tetrahydrofuran (THF), dimethyl formamide (DMF), N-methyl formamide (NMF), dimethyl sulfoxide (DMSO); thionyl chloride; and/or sulfuryl chloride.

Higher boiling point solvents are generally preferable for printing. A slow evaporation rate can reduce solvent loss during ink mixing and printing, as can influence the shelf life of an ink comprising the solvent.

Ionic Liquids

Ionic liquids (ILs) are generally organic molten salts which consist only of ions and are liquid at temperatures below 100° C. Every ionic liquid has a cation and anion. Suitable ionic liquids can be any combination from the list of cations and the list of anions below. For example, an IL described herein is $C_2mimBF_4$, which is a combination of the first cation and the first anion listed below.

Suitable cations include, but are not limited to: 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, diethylmethylsulfonium, and the like.

Suitable anions include, but are not limited to: tetrafluoroborate, tris(pentafluoroethyl)trifluorophosphate, hexafluorophosphate, ethyl sulfate, dimethyl phosphate, trifluoromethanesulfonate, methansulfonate, triflate, tricyanomethanide, dibutylphosphate, bis(trifluoromethylsulfonyl)imide, bis-2,4,4-(trimethylpentyl)phosphinate, iodide, chloride, bromide, nitrate, and the like.

Zinc Salts

Suitable zinc salts may include, but are not limited to: zinc chloride, zinc bis(trifluoromethanesulfonyl)imide, zinc sulfate, zinc nitrate, and/or zinc carbonate, and the like.

Other examples of suitable zinc salts may include combinations of zinc cation with organic and inorganic anions. In some embodiments, suitable zinc salts have desired solubility in the ionic liquid.

Microspheres

Suitable solid microspheres for the separator layer 4, the separator layer 73, etc., may be hollow or dense, and may be spherical or substantially spherical particles comprising non-conductive materials like glass, alumina, silica, polystyrene, and/or melamine. The solid microsphere particles size may have a diameter from about 0.5 µm to about 30 µm.

Substrates

Substrates can be conductive and/or non-conductive. Example substrates include, but are not limited to: graphite paper, graphene paper, polyester film, polyimide film, aluminum (Al) foil, copper (Cu) foil, stainless steel (SS) foil, carbon foam, polycarbonate film, paper, coated paper, plastic coated paper, fiber paper, and/or cardboard, and the like.

Printing Techniques

"Printing" includes any and all printing, for example, coating, rolling, spraying, layering, spin coating, laminating and/or affixing processes, for example, screen printing, inkjet printing, electro-optical printing, electroink printing, photoresist and other resist printing, thermal printing, laser jet printing, magnetic printing, pad printing, flexographic printing, hybrid offset lithography, Gravure and other intaglio printing, die slot deposition, and the like.

Ink Preparation Techniques

All kinds of ink mixing techniques are possible, including, but not limited to: mixing with stir bar, mixing with magnetic stirrer, vortexing (Vortex machine), shaking (using shakers), mixing by rotation, sonication, mortar and pestle, and the like.

Curing Conditions

Suitable temperatures for curing an ink used in printing one or more of the battery layers can have a value in a wide temperature range depending on solvents used, for example from about 70° C. to about 300° C. Drying time can vary from about 20 seconds to about 1 hour.

A suitable atmosphere for curing an ink used in printing one or more of the battery layers can be ambient, inert, or vacuum.

EXAMPLE EMBODIMENTS

The following example embodiments identify some possible permutations of combinations of features disclosed herein, although other permutations of combinations of features are also possible.

1. A printed energy storage device comprising:
   a first electrode;
   a second electrode; and
   a separator positioned between the first electrode and the second electrode, at least one of the first electrode, the second electrode, and the separator comprising an ionic liquid,
   wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
   wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

2. The printed energy storage device of Embodiment 1, wherein the ionic liquid comprises 1-ethyl-3-methylimidazolium tetrafluoroborate ($C_2mimBF_4$).

3. The printed energy storage device of Embodiment 1 or 2, wherein the first electrode comprises the ionic liquid.

4. The printed energy storage device of any one of Embodiments 1 to 3, wherein the second electrode comprises the ionic liquid.

5. The printed energy storage device of any one of Embodiments 1 to 4, wherein the separator comprises the ionic liquid.

6. The printed energy storage device of any one of Embodiments 1 to 5, wherein the printed energy storage device further comprises an intermediate layer.

7. The printed energy storage device of Embodiment 6, wherein the intermediate layer is between the first electrode and the separator.

8. The printed energy storage device of Embodiment 6, wherein the intermediate layer is between the second electrode and the separator.

9. The printed energy storage device of any one of Embodiments 6 to 8, wherein the intermediate layer comprises the ionic liquid.

10. The printed energy storage device of any one of Embodiments 1 to 9, wherein the printed energy storage device further comprises a current collector coupled to the first electrode or the second electrode.

11. The printed energy storage device of Embodiment 10, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

12. The printed energy storage device of any one of Embodiments 6 to 11, wherein at least one of the first electrode, the intermediate layer, and the separator comprises a salt.

13. The printed energy storage device of Embodiment 12, wherein the salt comprises a zinc salt.

14. The printed energy storage device of Embodiment 12 or 13, wherein the anion of the ionic liquid is the same as an anion of the salt.

15. The printed energy storage device of any one of Embodiments 12 to 14, wherein the salt comprises zinc tetrafluoroborate and the ionic liquid comprises 1-ethyl-3-methylimidazolium tetrafluoroborate.

16. The printed energy storage device of any one of Embodiments 12 to 15, wherein the salt comprises zinc chloride.

17. The printed energy storage device of any one of Embodiments 12 to 16, wherein the salt comprises zinc bis(trifluoromethanesulfonyl)imide.

18. The printed energy storage device of any one of Embodiments 12 to 17, wherein the salt comprises zinc sulfate.

19. The printed energy storage device of any one of Embodiments 12 to 18, wherein the salt comprises zinc nitrate.

20. The printed energy storage device of any one of Embodiments 12 to 19, wherein the salt comprises zinc carbonate.

21. The printed energy storage device of any one of Embodiments 1 to 20, wherein at least one of the first electrode and the second electrode comprises polyvinylidene difluoride.

22. The printed energy storage device of any one of Embodiments 10 to 21, wherein at least one of the second electrode and the current collector comprises carbon nanotubes.

23. The printed energy storage device of Embodiment 22, wherein the carbon nanotubes comprise single-wall carbon nanotubes.

24. The printed energy storage device of Embodiment 22 or 23, wherein the carbon nanotubes comprise multi-wall carbon nanotubes.

25. The printed energy storage device of any one of Embodiments 22 to 24, wherein the second electrode comprises a homogeneous paste comprising the carbon nanotubes and the ionic liquid.

26. The printed energy storage device of any one of Embodiments 1 to 25, wherein the second electrode comprises manganese dioxide.

27. The printed energy storage device of any one of Embodiments 1 to 26, wherein the second electrode comprises a conductive carbon.

28. The printed energy storage device of Embodiment 27, wherein the conductive carbon comprises graphite.

29. The printed energy storage device of any one of Embodiments 10 to 28, wherein the current collector comprises at least one of nickel flakes, graphene flakes, and graphite powder.

30. The printed energy storage device of Embodiment 29, wherein the current collector comprises nickel flakes.

31. The printed energy storage device of Embodiment 29, wherein the current collector comprises graphene flakes.

32. The printed energy storage device of Embodiment 29, wherein the current collector comprises nickel flakes and graphene flakes.

33. The printed energy storage device of Embodiment 29, wherein the current collector comprises nickel flakes, graphene flakes, and graphite powder.

34. The printed energy storage device of Embodiment 29, wherein the current collector comprises nickel flakes and carbon nanotubes.

35. The printed energy storage device of Embodiment 29, wherein the current collector comprises nickel flakes, graphene flakes, and carbon nanotubes.

36. The printed energy storage device of Embodiment 29, wherein the current collector comprises nickel flakes, graphene flakes, carbon nanotubes, and graphite powder.

37. The printed energy storage device of Embodiment 29, wherein the current collector comprises nickel flakes, carbon nanotubes, and graphite powder.

38. The printed energy storage device of any one of Embodiments 10 to 37, wherein the current collector comprises polyvinylidene difluoride.

39. The printed energy storage device of any one of Embodiments 1 to 38, wherein the separator comprises microspheres.

40. The printed energy storage device of Embodiment 39, wherein the microspheres comprises at least one of glass, alumina, silica, polystyrene, and melamine.

41. The printed energy storage device of Embodiment 39 or 40, wherein one or more of the microspheres are hollow.

42. The printed energy storage device of any one of Embodiment 39 or 40, wherein one or more of the microspheres are solid.

43. The printed energy storage device of any one of Embodiments 39 to 42, wherein one or more of the microspheres have a diameter from about 0.5 microns to about 30 microns.

44. The printed energy storage device of any one of Embodiments 1 to 43, wherein the separator comprises polyvinylidene difluoride.

45. The printed energy storage device of any one of Embodiments 6 to 44, wherein the intermediate layer comprises polyvinyl alcohol.

46. The printed energy storage device of any one of Embodiments 1 to 45, wherein the printed energy storage device is a printed zinc-manganese dioxide battery.

47. A layer of a printed energy storage device, the layer comprising
a salt including an anion; and
an ionic liquid including the anion.

48. The layer of Embodiment 47, wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium.

49. The layer of Embodiment 47 or 48, wherein the anion is selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

50. The layer of any one of Embodiments 47 to 49, wherein the ionic liquid comprises 1-ethyl-3-methylimidazolium tetrafluoroborate ($C_2mimBF_4$).

51. The layer of any one of Embodiments 47 to 50, wherein the salt comprises a zinc salt.

52. The layer of any one of Embodiments 47 to 51, wherein the salt comprises zinc tetrafluoroborate.

53. The layer of any one of Embodiments 47 to 52, wherein the salt comprises zinc chloride.

54. The layer of any one of Embodiments 47 to 53, wherein the salt comprises zinc bis(trifluoromethanesulfonyl)imide.

55. The layer of any one of Embodiments 47 to 54, wherein the salt comprises zinc sulfate.

56. The layer of any one of Embodiments 47 to 55, wherein the salt comprises zinc nitrate.

57. The layer of any one of Embodiments 47 to 56, wherein the salt comprises zinc carbonate.

58. The layer of any one of Embodiments 47 to 57, wherein the printed energy storage device comprises a first electrode, a second electrode, and a separator between the first electrode and the second electrode.

59. The layer of any one of Embodiments 47 to 58, wherein the printed energy storage device comprises an intermediate layer.

60. The layer of Embodiment 59, wherein the intermediate layer is between the first electrode and the separator.

61. The layer of Embodiment 59, wherein the intermediate layer is between the second electrode and the separator.

62. The layer of any one of Embodiments 47 to 61, wherein the printed energy storage device further comprises a current collector electrically coupled to the first electrode or the second electrode.

63. The layer of any one of Embodiments 58 to 62, wherein the layer is the first electrode.

64. The layer of any one of Embodiments 58 to 62, wherein the layer is the separator.

65. The layer of any one of Embodiments 59 to 62, wherein the layer is the intermediate layer.

66. The layer of any one of Embodiments 62 to 64, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

67. The layer of any one of Embodiments 62 to 66, wherein at least one of the first electrode, the second electrode, the separator, and the current collector comprises polyvinylidene difluoride.

68. The layer of any one of Embodiments 62 to 67, wherein at least one of the second electrode and the current collector comprises carbon nanotubes 69. The layer of Embodiment 68, wherein the carbon nanotubes comprise single-wall carbon nanotubes.

70. The layer of Embodiment 68 or 69, wherein the carbon nanotubes comprise multi-wall carbon nanotubes.

71. The layer of any one of Embodiments 68 to 70, wherein the second electrode comprises a mixture of the carbon nanotubes and the ionic liquid.

72. The layer of any one of Embodiments 58 to 71, wherein the second electrode comprises manganese dioxide.

73. The layer of any one of Embodiments 58 to 72, wherein the second electrode comprises a conductive carbon.

74. The layer of Embodiment 73, wherein the conductive carbon comprises graphite.

75. The layer of any one of Embodiments 62 to 74, wherein the current collector further comprises at least one of nickel flakes, graphene flakes, and graphite powder.

76. The layer of Embodiment 75, wherein the current collector comprises nickel flakes.

77. The layer of Embodiment 76, wherein the current collector is electrically coupled to the first electrode.

78. The layer of Embodiment 75, wherein the current collector comprises graphene flakes.

79. The layer of Embodiment 75, wherein the current collector is electrically coupled to the second electrode.

80. The layer of Embodiment 75, wherein the current collector comprises nickel flakes and graphene flakes.

81. The layer of Embodiment 75, wherein the current collector comprises nickel flakes, graphene flakes, and graphite powder.

82. The layer of Embodiment 75, wherein the current collector comprises nickel flakes and carbon nanotubes.

83. The layer of Embodiment 75, wherein the current collector comprises nickel flakes, graphene flakes, and carbon nanotubes.

84. The layer of Embodiment 75, wherein the current collector comprises nickel flakes, graphene flakes, carbon nanotubes, and graphite powder.

85. The layer of Embodiment 75, wherein the current collector comprises nickel flakes, carbon nanotubes, and graphite powder.

86. The layer of any one of Embodiments 58 to 85, wherein the separator comprises microspheres.

87. The layer of Embodiment 86, wherein the microspheres comprises at least one of glass, alumina, silica, polystyrene, and melamine.

88. The layer of Embodiment 86 or 87, wherein one or more of the microspheres are hollow.

89. The layer of any one of Embodiments 86 or 87, wherein one or more of the microspheres are solid.

90. The layer of any one of Embodiments 86 to 89, wherein one or more of the microspheres have a diameter from about 0.5 microns to about 30 microns.

91. The layer of any one of Embodiments 59 to 90, wherein the intermediate layer comprises polyvinyl alcohol.

92. The layer of any one of Embodiments 47 to 90, wherein the printed energy storage device is a printed zinc-manganese dioxide battery.

93. A layer of a printed energy storage device, the layer comprising:
    a salt comprising zinc tetrafluoroborate; and
    an ionic liquid comprising 1-ethyl-3-methylimidazolium tetrafluoroborate.

94. The layer Embodiment 93, wherein the printed energy storage device comprises a first electrode, a second electrode, and a separator between the first electrode and the second electrode.

95. The layer of Embodiments 93 or 94, wherein the printed energy storage device comprises an intermediate layer.

96. The layer of Embodiment 95, wherein the intermediate layer is between the first electrode and the separator.

97. The layer of Embodiment 95, wherein the intermediate layer is between the second electrode and the separator.

98. The layer of any one of Embodiments 93 to 97, wherein the printed energy storage device further comprises a current collector coupled to the first electrode or the second electrode.

99. The layer of any one of Embodiments 93 to 98, wherein the layer is the first electrode.

100. The layer of any one of Embodiments 93 to 99, wherein the layer is the separator.

101. The layer of any one of Embodiments 93 to 100, wherein the layer is the intermediate layer.

102. The layer of any one of Embodiments 98 to 101, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

103. The layer of any one of Embodiments 98 to 102, wherein at least one of the first electrode, the second electrode, the separator, and the current collector comprises polyvinylidene difluoride.

104. The layer of any one of Embodiments 98 to 103, wherein at least one of the second electrode and the current collector comprises carbon nanotubes.

105. The layer of Embodiment 104, wherein the carbon nanotubes comprise single-wall carbon nanotubes.

106. The layer of Embodiment 104 or 105, wherein the carbon nanotubes comprise multi-wall carbon nanotubes.

107. The layer of any one of Embodiments 104 to 106, wherein the second electrode comprises a homogeneous paste comprising the carbon nanotubes and the ionic liquid.

108. The layer of any one of Embodiments 94 to 107, wherein the second electrode comprises manganese dioxide.

109. The layer of any one of Embodiments 94 to 108, wherein the second electrode comprises a conductive carbon.

110. The layer of Embodiment 109, wherein the conductive carbon comprises graphite.

111. The layer of any one of Embodiments 98 to 110, wherein the current collector further comprises at least one of nickel flakes, graphene flakes, and graphite powder.

112. The layer of Embodiment 111, wherein the current collector comprises nickel flakes.

113. The layer of Embodiment 112, wherein the current collector is coupled to the first electrode.

114. The layer of Embodiment 111, wherein the current collector comprises graphene flakes.

115. The layer of Embodiment 114, wherein the current collector is coupled to the second electrode.

116. The layer of Embodiment 111, wherein the current collector comprises nickel flakes and graphene flakes.

117. The layer of Embodiment 111, wherein the current collector comprises nickel flakes, graphene flakes, and graphite powder.

118. The layer of Embodiment 111, wherein the current collector comprises nickel flakes and carbon nanotubes.

119. The layer of Embodiment 111, wherein the current collector comprises nickel flakes, graphene flakes, and carbon nanotubes.

120. The layer of Embodiment 111, wherein the current collector comprises nickel flakes, graphene flakes, carbon nanotubes, and graphite powder.

121. The layer of Embodiment 111, wherein the current collector comprises nickel flakes, carbon nanotubes, and graphite powder.

122. The layer of any one of Embodiments 94 to 121, wherein the separator comprises microspheres.

123. The layer of Embodiment 122, wherein the microspheres comprises at least one of glass, alumina, silica, polystyrene, and melamine.

124. The layer of Embodiment 122 or 123, wherein one or more of the microspheres are hollow.

125. The layer of any one of Embodiments 122 or 123, wherein one or more of the microspheres are solid.

126. The layer of any one of Embodiments 122 to 125, wherein one or more of the microspheres have a diameter from about 0.5 microns to about 30 microns.

127. The layer of any one of Embodiments 95 to 126, wherein the intermediate layer comprises polyvinyl alcohol.

128. The layer of any one of Embodiments 93 to 127, wherein the printed energy storage device is a printed zinc-manganese dioxide battery.

129. A planarization adhesion layer of a printed energy storage device, the planarization adhesion layer comprising:
polyvinyl alcohol;
a salt; and
an ionic liquid,
wherein the ionic liquid comprises a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid comprises an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

130. The planarization adhesion layer of Embodiment 129, wherein the salt comprises an anion that is the same as the anion of the ionic liquid.

131. The planarization adhesion layer of Embodiment 129 or 130, wherein the salt comprises a zinc salt.

132. The planarization adhesion layer of any one of Embodiments 129 to 131, wherein the salt comprises zinc tetrafluorborate and the ionic liquid comprises 1-ethyl-3-methylimidazolium tetrafluoroborate.

133. The planarization adhesion layer of any one of Embodiments 129 to 132, wherein the salt comprises zinc chloride.

134. The planarization adhesion layer of any one of Embodiments 129 to 133, wherein the zinc salt comprises zinc bis(trifluoromethanesulfonyl)imide.

135. The planarization adhesion layer of any one of Embodiments 129 to 134, wherein the zinc salt comprises zinc sulfate.

136. The planarization adhesion layer of any one of Embodiments 129 to 135, wherein the zinc salt comprises zinc nitrate.

137. The planarization adhesion layer of any one of Embodiments 129 to 136, wherein the zinc salt comprises zinc carbonate.

138. The planarization adhesion layer of any one of Embodiments 129 to 137, wherein the printed energy storage device comprises a first electrode, a second electrode, and a separator between the first electrode and the second electrode.

139. The planarization adhesion layer of Embodiment 129 to 138, wherein the planarization adhesion layer is between the first electrode and the separator.

140. The planarization adhesion layer of Embodiment 129 to 138, wherein the planarization adhesion layer is between the second electrode and the separator.

141. The planarization adhesion layer of any one of Embodiments 129 to 140, wherein the printed energy storage device further comprises a current collector electrically coupled to the first electrode or the second electrode.

142. The planarization adhesion layer of any one of Embodiments 141, wherein at least one of the first electrode, the second electrode, the separator, the planarization adhesion layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

143. The planarization adhesion layer of any one of Embodiments 141 or 142, wherein at least one of the first electrode, the second electrode, the separator, and the current collector comprises polyvinylidene difluoride.

144. The planarization adhesion layer of any one of Embodiments 141 to 143, wherein at least one of the second electrode and the current collector comprises carbon nanotubes.

145. The planarization adhesion layer of Embodiment 144, wherein the carbon nanotubes comprise single-wall carbon nanotubes.

146. The planarization adhesion layer of Embodiment 144 or 145, wherein the carbon nanotubes comprise multi-wall carbon nanotubes.

147. The planarization adhesion layer of any one of Embodiments 138 to 146, wherein the second electrode comprises a mixture comprising the carbon nanotubes and the ionic liquid.

148. The planarization adhesion layer of any one of Embodiments 138 to 147, wherein the second electrode comprises manganese dioxide.

149. The planarization adhesion layer of any one of Embodiments 138 to 148, wherein the second electrode comprises a conductive carbon.

150. The planarization adhesion layer of Embodiment 149, wherein the conductive carbon comprises graphite.

151. The planarization adhesion layer of any one of Embodiments 141 to 150, wherein the current collector further comprises at least one of nickel flakes, graphene flakes, and graphite powder.

152. The planarization adhesion layer of Embodiment 151, wherein the current collector comprises nickel flakes.

153. The planarization adhesion layer of Embodiment 152, wherein the current collector is electrically coupled to the first electrode.

154. The planarization adhesion layer of Embodiment 151, wherein the current collector comprises graphene flakes.

155. The planarization adhesion layer of Embodiment 154, wherein the current collector is electrically coupled to the second electrode.

156. The planarization adhesion layer of Embodiment 151, wherein the current collector comprises nickel flakes and graphene flakes.

157. The planarization adhesion layer of Embodiment 151, wherein the current collector comprises nickel flakes, graphene flakes, and graphite powder.

158. The planarization adhesion layer of Embodiment 151, wherein the current collector comprises nickel flakes and carbon nanotubes.

159. The planarization adhesion layer of Embodiment 151, wherein the current collector comprises nickel flakes, graphene flakes, and carbon nanotubes.

160. The planarization adhesion layer of Embodiment 151, wherein the current collector comprises nickel flakes, graphene flakes, carbon nanotubes, and graphite powder.

161. The planarization adhesion layer of Embodiment 151, wherein the current collector comprises nickel flakes, carbon nanotubes, and graphite powder.

162. The planarization adhesion layer of any one of Embodiments 138 to 161, wherein the separator comprises microspheres.

163. The planarization adhesion layer of Embodiment 162, wherein the microspheres comprises at least one of glass, alumina, silica, polystyrene, and melamine.

164. The planarization adhesion layer of Embodiment 162 or 163, wherein one or more of the microspheres are hollow.

165. The planarization adhesion layer of any one of Embodiments 162 or 163, wherein one or more of the microspheres are solid.

166. The planarization adhesion layer of any one of Embodiments 162 to 165, wherein one or more of the microspheres have a diameter from about 0.5 microns to about 30 microns.

167. The planarization adhesion layer of any one of Embodiments 138 to 166, wherein at least one of the first electrode, separator, and second electrode comprises the ionic liquid.

168. The planarization adhesion layer of any one of Embodiments 138 to 167, wherein the printed energy storage device is a printed zinc-manganese dioxide battery.

169. An electrode of a printed energy storage device, the electrode comprising:
    carbon nanotubes; and
    an ionic liquid,
    wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
    wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

170. The electrode of Embodiment 169, wherein the carbon nanotubes comprise single-wall carbon nanotubes.

171. The electrode of Embodiment 169 or 170, wherein the carbon nanotubes comprise multi-wall carbon nanotubes.

172. The electrode of any one of Embodiments 169 to 171, wherein the ionic liquid comprises 1-ethyl-3-methylimidazolium tetrafluoroborate.

173. The electrode of any one of Embodiments 169 to 172, wherein the carbon nanotubes are ground.

174. The electrode of any one of Embodiments 169 to 173, wherein the carbon nanotubes and the ionic liquid form a homogeneous mixture.

175. The electrode of any one of Embodiments 169 to 174, wherein the electrode comprises manganese dioxide.

176. The electrode of any one of Embodiments 169 to 175, wherein the electrode comprises graphite powder.

177. The electrode of any one of Embodiments 169 to 176, wherein the printed energy storage device further comprises a second electrode and a separator between the electrode and the second electrode.

178. The electrode of any one of Embodiments 169 to 177, wherein the printed energy storage device further comprises an intermediate layer.

179. The electrode of Embodiment 178, wherein the intermediate layer is between the separator and the electrode.

180. The electrode of Embodiment 178, wherein the intermediate layer is between the separator and the second electrode.

181. The electrode of any one of Embodiments 177 to 180, wherein the printed energy storage device further comprises a current collector electrically coupled to the electrode or the second electrode.

182. The electrode of any one of Embodiments 178 to 181, wherein at least one of the second electrode, the separator, and the intermediate layer comprises the ionic liquid.

183. The electrode of any one of Embodiments 178 to 182, wherein at least one of the second electrode, the separator, and the intermediate layer comprises a salt.

184. The electrode of Embodiment 183, wherein the salt comprises an anion that is the same as an anion of the ionic liquid.

185. The electrode of Embodiment 183 or 184, wherein the salt comprises a zinc salt.

186. The electrode of any one of Embodiments 183 to 185, wherein the salt comprises zinc tetrafluorborate and the ionic liquid comprises 1-ethyl-3-methylimidazolium tetrafluoroborate.

187. The electrode of any one of Embodiments 183 to 186, wherein the salt comprises zinc chloride.

188. The electrode of any one of Embodiments 183 to 187, wherein the salt comprises zinc bis(trifluoromethanesulfonyl)imide.

189. The electrode of any one of Embodiments 183 to 188, wherein the salt comprises zinc sulfate.

190. The electrode of any one of Embodiments 183 to 189, wherein the salt comprises zinc nitrate.

191. The electrode of any one of Embodiments 183 to 190, wherein the salt comprises zinc carbonate.

192. The electrode of any one of Embodiments 181 to 191, wherein at least one of the electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxy ethylcellulose, cellulose ether, cellulose ethyl ether, and chitosan.

193. The electrode of any one of Embodiments 181 to 192, wherein at least one of the electrode, the second electrode, the separator, and the current collector comprises polyvinylidene difluoride.

194. The electrode of any one of Embodiments 181 to 193, wherein the current collector further comprises at least one of nickel flakes, graphene flakes, and graphite powder.

195. The electrode of Embodiment 194, wherein the current collector comprises nickel flakes.

196. The electrode of Embodiment 195, wherein the current collector is coupled to the second electrode.

197. The electrode of Embodiment 194, wherein the current collector comprises graphene flakes.

198. The electrode of Embodiment 197, wherein the current collector is coupled to the first electrode.

199. The electrode of Embodiment 194, wherein the current collector comprises nickel and graphene flakes.

200. The electrode of Embodiment 194, wherein the current collector comprises nickel flakes, graphene flakes, and graphite powder.

201. The electrode of Embodiment 194, wherein the current collector comprises nickel flakes and carbon nanotubes.

202. The electrode of Embodiment 194, wherein the current collector comprises nickel flakes, graphene flakes, and carbon nanotubes.

203. The electrode of Embodiment 194, wherein the current collector comprises nickel flakes, graphene flakes, carbon nanotubes, and graphite powder.

204. The electrode of Embodiment 194, wherein the current collector comprises nickel flakes, carbon nanotubes, and graphite powder.

205. The electrode of any one of Embodiments 177 to 204, wherein the separator comprises microspheres.

206. The electrode of Embodiment 205, wherein the microspheres comprises at least one of glass, alumina, silica, polystyrene, and melamine.

207. The electrode of Embodiment 205 or 206, wherein one or more of the microspheres are hollow.

208. The electrode of Embodiment 205 or 206, wherein one or more of the microspheres are solid.

209. The electrode of any one of Embodiments 205 to 208, wherein one or more of the microspheres have a diameter from about 0.5 microns to about 30 microns.

210. The electrode of any one of Embodiments 178 to 209, wherein the intermediate layer comprises polyvinyl alcohol.

211. The planarization adhesion layer of any one of Embodiments 169 to 210, wherein the printed energy storage device is a printed zinc-manganese dioxide battery.

212. A printed energy storage device comprising:
a first electrode comprising zinc;
a second electrode comprising manganese dioxide;
a separator between the first electrode and the second electrode; and
a current collector electrically connected to the first electrode or the second electrode, the current collector comprising conductive flakes.

213. The printed energy storage device of Embodiment 212, wherein the current collector further comprises carbon nanotubes.

214. The printed energy storage device of Embodiment 213, wherein the carbon nanotubes comprise single-wall carbon nanotubes.

215. The printed energy storage device of Embodiment 213 or 214, wherein the carbon nanotubes comprise multi-wall carbon nanotubes.

216. The printed energy storage device of any one of Embodiments 212 to 215, wherein the conductive flakes comprise at least one of nickel flakes, graphene flakes, and graphite powder.

217. The printed energy storage device of Embodiment 216, wherein the current collector comprises nickel flakes.

218. The printed energy storage device of Embodiment 217, wherein the current collector is electrically coupled to the first electrode.

219. The printed energy storage device of Embodiment 216, wherein the current collector comprises graphene flakes.

220. The printed energy storage device of Embodiment 219, wherein the current collector is electrically coupled to the second electrode.

221. The printed energy storage device of Embodiment 216, wherein the current collector comprises nickel and graphene flakes.

222. The printed energy storage device Embodiment 216, wherein the current collector comprises nickel flakes, graphene flakes, and graphite powder.

223. The printed energy storage device Embodiment 216, wherein the current collector comprises nickel flakes and carbon nanotubes.

224. The printed energy storage device of Embodiment 216, wherein the current collector comprises nickel flakes, graphene flakes, and carbon nanotubes.

225. The printed energy storage device of Embodiment 216, wherein the current collector comprises nickel flakes, graphene flakes, carbon nanotubes, and graphite powder.

226. The printed energy storage device of any one of Embodiments 212 to 225, wherein the printed energy storage device further includes an intermediate layer.

227. The printed energy storage device Embodiment 226, wherein the intermediate layer is between the first electrode and the separator.

228. The printed energy storage device Embodiment 226, wherein the intermediate layer is between the second electrode and the separator.

229. The printed energy storage device of any one of Embodiment 226 to 228, wherein the at least one of the first electrode, the second electrode, the separator and the intermediate layer comprises an ionic liquid,
  wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
  wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

230. The printed energy storage device of Embodiment 229, wherein the ionic liquid comprises 1-ethyl-3-methylimidazolium tetrafluoroborate ($C_2mimBF_4$).

231. The printed energy storage device of any one of Embodiments 226 to 230, wherein at least one of the first electrode, the separator, and the intermediate layer comprises a salt.

232. The printed energy storage device of Embodiment 231, wherein the salt comprises an anion that is the same as the anion of the ionic liquid.

233. The printed energy storage device of any one of Embodiment 231 or 232, wherein the salt comprises zinc tetrafluoroborate and the ionic liquid comprises 1-ethyl-3-methylimidazolium tetrafluoroborate.

234. The printed energy storage device of any one of Embodiments 231 to 233, wherein the salt comprises zinc chloride.

235. The printed energy storage device of any one of Embodiments 231 to 234, wherein the salt comprises zinc bis(trifluoromethanesulfonyl)imide.

236. The printed energy storage device of any one of Embodiments 231 to 235, wherein the salt comprises zinc sulfate.

237. The printed energy storage device of any one of Embodiments 231 to 236, wherein the salt comprises zinc nitrate.

238. The printed energy storage device of any one of Embodiments 231 to 237, wherein the salt comprises zinc carbonate.

239. The printed energy storage device of any one of Embodiments 212 to 250, wherein the first electrode comprises polyvinylidene difluoride.

240. The printed energy storage device of any one of Embodiments 226 to 239, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

241. The printed energy storage device of any one of Embodiments 213 to 240, wherein the second electrode comprises the carbon nanotubes.

242. The printed energy storage device of Embodiment 241, wherein the second electrode comprises a homogeneous paste comprising the carbon nanotubes and the ionic liquid.

243. The printed energy storage device of any one of Embodiments 212 to 242, wherein the second electrode further comprises a conductive carbon.

244. The printed energy storage device of Embodiment 243, wherein the conductive carbon comprises graphite powder.

245. The printed energy storage device of any one of Embodiments 212 to 244, wherein the separator comprises microspheres.

246. The printed energy storage device of Embodiment 245, wherein the microspheres comprises at least one of glass, alumina, silica, polystyrene, and melamine.

247. The printed energy storage device of Embodiment 245 or 246, wherein one or more of the microspheres are hollow.

248. The printed energy storage device of Embodiment 245 or 246, wherein one or more of the microspheres are solid.

249. The printed energy storage device of any one of Embodiments 245 to 248, wherein one or more of the microspheres have a diameter from about 0.5 microns to about 30 microns.

250. The printed energy storage device of any one of Embodiments 226 to 249, wherein the intermediate layer comprises polyvinyl alcohol.

251. The printed energy storage device of any one of Embodiments 212 to 250, wherein the printed energy storage device is a printed zinc-manganese dioxide battery.

252. A conductive paste for a layer of a printed energy storage device, the conductive paste comprising:
carbon nanotubes; and
an ionic liquid,
wherein the ionic liquid comprises a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid comprises an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

253. The paste of Embodiment 252, wherein the ionic liquid comprises 1-ethyl-3-methylimidazolium tetrafluoroborate ($C_2mimBF_4$).

254. The paste of Embodiment 252 or 253, wherein the carbon nanotubes are single-wall carbon nanotubes.

255. The paste of Embodiment 252 to 254, wherein the carbon nanotubes are multi-wall carbon nanotubes.

256. The paste of any one of Embodiments 252 to 255, wherein the carbon nanotubes are ground.

257. The paste of any one of Embodiments 252 to 256, wherein the carbon nanotubes and the ionic liquid form a homogeneous mixture.

258. The paste of any one of Embodiments 252 to 257, wherein the layer comprises a first electrode.

259. The paste of Embodiment 258, wherein the first electrode comprises manganese dioxide.

260. The paste of Embodiment 258 or 259, wherein the first electrode comprises graphite.

261. The paste of any one of Embodiments 252 to 260, wherein the printed energy storage device further comprises a second electrode and a separator between the first electrode and the second electrode.

262. The paste of any one of Embodiments 252 to 261, wherein the printed energy storage device further comprises an intermediate layer.

263. The paste of Embodiment 262, wherein the intermediate layer is between the first electrode and the separator.

264. The paste of Embodiment 262, wherein the intermediate layer is between the second electrode and the separator.

265. The paste of any one of Embodiments 252 to 264, wherein the printed energy storage device further comprises a current collector electrically coupled to the first electrode or the second electrode.

266. The paste of any one of Embodiments 262 to 265, wherein at least one of the second electrode, the separator, and the intermediate layer comprises the ionic liquid.

267. The paste of any one of Embodiments 262 to 266, wherein at least one of the second electrode, the separator, and the intermediate layer comprises a salt.

268. The paste of Embodiment 267, wherein the salt comprises a zinc salt.

269. The paste of Embodiment 267 or 268, wherein the salt comprises an anion that is the same as the anion of the ionic liquid.

270. The paste of any one of Embodiments 267 to 269, wherein the salt comprises zinc tetrafluoroborate and the ionic liquid comprises 1-ethyl-3-methylimidazolium tetrafluoroborate.

271. The paste of any one of Embodiments 267 to 270, wherein the salt comprises zinc chloride.

272. The paste of any one of Embodiments 267 to 271, wherein the salt comprises zinc bis(trifluoromethanesulfonyl)imide.

273. The paste of any one of Embodiments 267 to 272, wherein the salt comprises zinc sulfate.

274. The paste of any one of Embodiments 267 to 273, wherein the salt comprises zinc nitrate.

275. The paste of any one of Embodiments 267 to 274, wherein the salt comprises zinc carbonate.

276. The paste of any one of Embodiments 265 to 275, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

277. The paste of any one of Embodiments 265 to 276, wherein at least one of the first electrode, the second electrode, the separator, and the current collector comprises polyvinylidene difluoride.

278. The paste of any one of Embodiments 265 to 277, wherein the current collector comprises the carbon nanotubes.

279. The paste of any one of Embodiments 265 to 278, wherein the current collector further comprises at least one of nickel flakes, graphene flakes, and graphite powder.

280. The paste of Embodiment 279, wherein the current collector comprises nickel flakes.

281. The paste of Embodiment 280, wherein the current collector is electrically coupled to the second electrode.

282. The paste of Embodiment 279, wherein the current collector comprises graphene flakes.

283. The paste of Embodiment 282, wherein the current collector is electrically coupled to the first electrode.

284. The paste of Embodiment 279, wherein the current collector comprises nickel and graphene flakes.

285. The paste of Embodiment 279, wherein the current collector comprises nickel flakes, graphene flakes, and graphite powder.

286. The paste of Embodiment 279, wherein the current collector comprises nickel flakes and carbon nanotubes.

287. The paste of Embodiment 279, wherein the current collector comprises nickel flakes, graphene flakes, and carbon nanotubes.

288. The paste of Embodiment 279, wherein the current collector comprises nickel flakes, graphene flakes, carbon nanotubes, and graphite powder.

289. The paste of Embodiment 279, wherein the current collector comprises nickel flakes, carbon nanotubes, and graphite powder.

290. The paste of any one of Embodiments 261 to 289, wherein the separator comprises microspheres.

291. The paste of Embodiment 290, wherein the microspheres comprises at least one of glass, alumina, silica, polystyrene, and melamine.

292. The paste of Embodiment 290 or 291, wherein one or more of the microspheres are hollow.

293. The paste of Embodiment 290 or 291, wherein one or more of the microspheres are solid.

294. The paste of any one of Embodiments 290 to 293, wherein one or more of the microspheres have a diameter from about 0.5 microns to about 30 microns.

295. The paste of any one of Embodiments 262 to 294, wherein the intermediate layer comprises polyvinyl alcohol.

296. The paste of any one of Embodiments 252 to 295, wherein the printed energy storage device is a printed zinc-manganese dioxide battery.

297. A printed separator for a printed energy storage device, the separator comprising:
a porous separator including a plurality of pores; and
a liquid electrolyte in the plurality of pores, the liquid electrolyte comprising an ionic liquid,
wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

298. The printed separator of Embodiment 297, wherein a size of the plurality of pores is between about 0.1 microns and about 10 microns.

299. The printed separator of Embodiment 297 or 298, wherein the ionic liquid is 1-ethyl-3-methylimidazolium tetrafluoroborate ($C_2mimBF_4$).

300. The printed separator of any one of Embodiments 297 to 299, wherein the liquid electrolyte further comprises a salt including the anion of the ionic liquid.

301. The printed separator of Embodiment 300, wherein the salt comprises a zinc salt.

302. The printed separator of any one of Embodiments 297 to 301, wherein the porous separator comprises at least one of polytetrafluoroethylene (PTFE) and styrene butadiene rubber (SBR).

303. The printed separator of any one of Embodiments 297 to 302, wherein the printed energy storage device further comprises a first electrode and a second electrode, at least one of the first electrode and the second electrode comprising styrene butadiene rubber.

304. The printed separator of Embodiment 303, wherein at least one of the first electrode and the second electrode further comprises an electrolyte.

305. The printed separator of Embodiment 303 or 304, wherein the electrolyte comprises the ionic liquid.

306. The printed separator of any one of Embodiments 303 to 305, wherein the electrode further comprises carbon nanotubes.

307. The printed separator of Embodiment 306, wherein the carbon nanotubes comprise single-wall carbon nanotubes.

308. The printed separator of Embodiment 306 or 307, wherein the carbon nanotubes comprise multi-wall carbon nanotubes.

309. The printed separator of any one of Embodiments 306 to 308, wherein the carbon nanotubes are ground.

310. The printed separator of any one of Embodiments 306 to 309, wherein the carbon nanotubes and the ionic liquid form a homogeneous mixture.

311. The printed separator of any one of Embodiments 303 to 310, wherein the first electrode comprises zinc and the second electrode comprises manganese dioxide.

312. The printed separator of any one of Embodiments 303 to 311, wherein at least one of the first electrode and the second electrode comprises at least one of graphite and graphene.

313. The printed separator of any one of Embodiments 297 to 312, wherein the printed energy storage device further comprises a separator sealing layer between the printed separator and the first electrode.

314. The printed separator of any one of Embodiments 297 to 313, wherein the printed energy storage device further comprises a separator sealing layer between the printed separator and the second electrode.

315. The printed separator of Embodiment 313 or 314, wherein the separator sealing layer comprises an electrolyte.

316. The printed separator of any one of Embodiments 303 to 315, wherein the printed energy storage device further comprises at least one of a first current collector electrically coupled to the first electrode and a second current collector electrically coupled to the second electrode.

317. The printed separator of Embodiment 316, wherein at least one of the first electrode, the second electrode, the separator, the separator sealing layer, the first current collector and the second current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

318. The printed separator of Embodiment 316 or 317, wherein at least one of the first current collector and the second current collector further comprises at least one of nickel flakes, graphene flakes, and graphite powder.

319. The printed separator of any one of Embodiments 316 to 318, wherein at least one of the first current collector and the second current collector comprises carbon nanotubes.

320. The printed separator of any one of Embodiments 297 to 319, wherein the separator comprises microspheres.

321. The printed separator of Embodiment 320, wherein the microspheres comprises at least one of glass, alumina, silica, polystyrene, and melamine.

322. The printed separator of Embodiment 320 or 321, wherein one or more of the microspheres are hollow.

323. The printed separator of Embodiment 320 or 321, wherein one or more of the microspheres are solid.

324. A printed electrode for a printed energy storage device, the printed electrode comprising:
an electrolyte; and
a styrene butadiene rubber.

325. The printed electrode of Embodiment 324, wherein the electrolyte comprises an ionic liquid,
wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

326. The printed electrode of Embodiment 324 or 325, wherein the electrolyte comprises a zinc salt.

327. The printed electrode of any one of Embodiments 324 to 326, further comprising carbon nanotubes.

328. The printed electrode of Embodiment 327, wherein at least some of the carbon nanotubes comprise single-walled carbon nanotubes.

329. The printed electrode of Embodiment 327 or 328, wherein at least some of the carbon nanotubes comprise multi-walled carbon nanotubes.

330. The printed electrode of any one of Embodiment 324 to 329, further comprising at least one of zinc and a conductive carbon, wherein the printed electrode is an anode of a zinc manganese dioxide battery.

331. The printed electrode of any one of Embodiment 324 to 329, further comprising at least one of manganese dioxide and a conductive carbon, wherein the printed electrode is a cathode of a zinc manganese dioxide battery.

332. The printed electrode of any one of Embodiments 325 to 331, wherein the ionic liquid comprises 1-ethyl-3-methylimidazolium tetrafluoroborate ($C_2mimBF_4$).

333. The printed electrode of any one of Embodiments 324 to 332, wherein the electrolyte further comprises a salt including the anion of the ionic liquid.

334. The printed electrode of Embodiment 333, wherein the salt comprises a zinc salt.

335. The printed electrode of any one of Embodiments 324 to 334, wherein the printed energy storage device further comprises a separator layer.

336. The printed electrode of Embodiment 335, wherein the separator layer comprises a plurality of pores and the separator layer comprising a liquid electrolyte in the plurality of pores, 337. The printed electrode of Embodiment 335 or 336, wherein the liquid electrolyte comprises the ionic liquid.

338. The printed electrode of any one of Embodiments 335 to 337, wherein the separator comprises at least one of polytetrafluoroethylene (PTFE) and styrene butadiene rubber (SBR).

339. The printed electrode of any one of Embodiments 335 to 338, wherein the separator comprises microspheres.

340. The printed electrode of Embodiment 339, wherein the microspheres comprises at least one of glass, alumina, silica, polystyrene, and melamine.

341. The printed electrode of Embodiment 339 or 340, wherein one or more of the microspheres is hollow.

342. The printed electrode of Embodiment 339 or 340, wherein one or more of the microspheres is solid.

343. The printed electrode of any one of Embodiments 324 to 342, wherein the printed energy storage device further comprises a current collector, the current collector comprising at least one of nickel flakes, graphene flakes, graphite powder, and carbon nanotubes.

344. The printed electrode of any one of Embodiments 324 to 343, further comprising at least one of graphite and graphene.

345. The printed electrode of any one of Embodiments 327 to 344, wherein the carbon nanotubes are ground.

346. The printed electrode of any one of Embodiments 327 to 345, wherein the carbon nanotubes and the ionic liquid form a homogeneous mixture.

347. The printed electrode of any one of Embodiments 324 to 346, wherein the printed energy storage device further comprises a separator sealing layer between the separator and a first electrode.

348. The printed electrode of any one of Embodiments 324 to 347, wherein the printed energy storage device further comprises a separator sealing layer between the separator and a second electrode.

349. The printed electrode of Embodiment 347 or 348, wherein the separator sealing layer comprises an electrolyte.

350. The printed electrode of any one of Embodiments 347 to 349, wherein at least one of the printed electrode, the separator, the separator sealing layer, the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

351. A printed energy storage device, comprising:
a first electrode;
a second electrode;
a porous separator between the first electrode and the second electrode, the porous separator including a plurality of pores and a liquid electrolyte in the plurality of pores,
wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

352. The printed energy storage device of Embodiment 351, wherein a size of the plurality of pores is between about 0.1 microns and about 10 microns.

353. The printed energy storage device of Embodiment 351 or 352, wherein at least one of the porous separator, the first electrode and the second electrode comprises a styrene butadiene rubber.

354. The printed energy storage device of any one of Embodiments 351 to 353, wherein at least one of the first electrode and the second electrode comprises the ionic liquid.

355. The printed energy storage device of any one of Embodiments 351 to 354, wherein the electrode further comprises carbon nanotubes.

356. The printed energy storage device of Embodiment 355, wherein at least some of the carbon nanotubes comprise single-wall carbon nanotubes.

357. The printed energy storage device of Embodiment 355 or 356, wherein at least some of the carbon nanotubes comprise multi-wall carbon nanotubes.

358. The printed energy storage device of any one of Embodiments 355 to 357, wherein the carbon nanotubes are ground.

359. The printed energy storage device of any one of Embodiments 355 to 358, wherein the carbon nanotubes and the ionic liquid form a homogeneous mixture.

360. The printed energy storage device of any one of Embodiments 351 to 359, wherein at least one of the first electrode and the second electrode comprises graphite and graphene.

361. The printed energy storage device of any one of Embodiments 351 to 360, wherein the printed energy storage device is a zinc manganese dioxide battery.

362. The printed energy storage device of any one of Embodiments 351 to 361, wherein the ionic liquid comprises 1-ethyl-3-methylimidazolium tetrafluoroborate ($C_2mimBF_4$).

363. The printed energy storage device of any one of Embodiments 351 to 362, wherein the liquid electrolyte further comprises a salt including the anion of the ionic liquid.

364. The printed energy storage device of any one of Embodiments 351 to 363, wherein the separator comprises at least one of polytetrafluoroethylene (PTFE) and styrene butadiene rubber.

365. The printed energy storage device of any one of Embodiments 351 to 364, wherein the separator comprises microspheres.

366. The printed energy storage device of Embodiment 365, wherein the microspheres comprises at least one of glass, alumina, silica, polystyrene, and melamine.

367. The printed energy storage device of Embodiment 365 or 366, wherein one or more of the microspheres is hollow.

368. The printed energy storage device of any one of Embodiments 365-367, wherein one or more of the microspheres is solid.

369. The printed energy storage device of any one of Embodiments 351 to 368, wherein the printed energy storage device further comprises a separator sealing layer between the printed separator and the first electrode.

370. The printed energy storage device of any one of Embodiments 351 to 369, wherein the printed energy storage device further comprises a separator sealing layer between the printed separator and the second electrode.

371. The printed energy storage device of Embodiment 369 or 370, wherein the separator sealing layer comprises a plurality of pores and an electrolyte in the pores.

372. The printed energy storage device of any one of Embodiments 351 to 371, wherein the printed energy storage device further comprises at least one of a first current collector electrically coupled to the first electrode and a second current collector electrically coupled to the second electrode.

373. The printed separator of Embodiment 372, wherein at least one of the first current collector and the second current collector further comprises at least one of nickel flakes, graphene flakes, and graphite powder.

374. The printed separator of Embodiment 372 or 373, wherein at least one of the first current collector and the second current collector comprises carbon nanotubes.

375. The printed energy storage device of any one of Embodiments 372 to 374, wherein at least one of the first electrode, the second electrode, the separator, the separator sealing layer, the first current collector and the second current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

376. A method of fabricating a separator for a printed energy storage device, the method comprising:
forming an electrolyte layer over a separator layer comprising a plurality of pores; and
diffusing the electrolyte layer into the plurality of pores of the separator.

377. The method of Embodiment 376, wherein the electrolyte layer comprises an ionic liquid,
wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

378. The method of Embodiment 376 or 377, wherein the electrolyte layer further comprises a salt.

379. The method of any one of Embodiments 376 to 378, further comprising applying a centrifugal force to a solution to separate the solution into at least two substantially distinct phases, the at least two substantially distinct phases including a lower phase and an upper phase, the electrolyte layer comprising the lower phase.

380. The method of Embodiment 379, further comprising removing the lower phase from the upper phase.

381. The method of Embodiment 379 or 380, wherein forming the electrolyte layer over the separator layer comprises forming a layer comprising the lower phase over the separator layer.

382. The method of any one of Embodiments 379 to 381, wherein applying the centrifugal force comprises centrifuging the solution at a rate of about 3000 revolutions per minute to about 15000 revolutions per minute.

383. The method of any one of Embodiments 379 to 382, wherein applying the centrifugal force comprises centrifuging the solution for a duration of about 1 minute to about 10 minutes.

384. The method of Embodiment 382 or 383, further comprising selecting at least one of the rate and the duration based on a concentration and/or a specific gravity of the solution.

385. The method of any one of Embodiments 379 to 384, wherein applying the centrifugal force comprises centrifuging the solution at a rate of about 10000 revolutions per minute for a duration of about 5 minutes.

386. The method of any one of Embodiments 376 to 385, wherein diffusing the electrolyte layer into the separator layer comprises heating the electrolyte layer.

387. The method of Embodiment 386, wherein heating the electrolyte layer comprises heating the electrolyte layer to a temperature configured to reduce a viscosity of the electrolyte layer and substantially without evaporating the electrolyte layer.

388. The method of any one of Embodiments 378 to 387, wherein the salt comprises a zinc salt.

389. The method of Embodiment 388, wherein an anion of the zinc salt comprises the anion of the ionic liquid.

390. The method of any one of Embodiments 377 to 389, wherein the ionic liquid comprises 1-ethyl-3-methylimidazolium tetrafluoroborate ($C_2mimBF_4$).

391. The method of any one of Embodiments 376 to 390, the separator layer comprises at least one of polytetrafluoroethylene (PTFE) and styrene butadiene rubber (SBR).

392. The method of any one of Embodiments 376 to 391, wherein a size of the plurality of pores of the separator layer is about 0.1 micron to about 10 microns.

393. The method of any one of Embodiments 376 or 392, wherein the separator layer comprises microspheres.

394. The method of Embodiment 393, wherein the microspheres comprises at least one of glass, alumina, silica, polystyrene, and melamine.

395. The method of Embodiment 393 or 394, wherein at least one of the microspheres is hollow.

396. The method of any one of Embodiments 393 to 395, wherein at least one of the microspheres is solid.

397. The method of any one of Embodiments 376 to 396, further comprising providing a first electrode and a second electrode, at least one of the first electrode and the second electrode comprising styrene butadiene rubber.

398. The method of Embodiment 397, wherein providing the first electrode and the second electrode comprise providing at least one of the first electrode including an electrolyte and the second electrode including the electrolyte.

399. The method of Embodiment 398, wherein the electrolyte comprises the ionic liquid.

400. The method of any one of Embodiments 397 to 399, wherein providing the first electrode and the second electrode comprises providing at least one of the first electrode comprising carbon nanotubes and the second electrode comprising carbon nanotubes.

401. The method of Embodiment 400, wherein at least some of the carbon nanotubes comprise single-wall carbon nanotubes.

402. The method of Embodiment 400 or 401, wherein at least some of the carbon nanotubes comprise multi-wall carbon nanotubes.

403. The method of any one of Embodiments 400 to 402, further comprising grinding the carbon nanotubes.

404. The method of any one of Embodiments 400 to 403, further comprising forming a homogeneous mixture comprising the carbon nanotubes and the ionic liquid.

405. The method of any one of Embodiments 397 to 404, wherein providing the first electrode and providing the second electrode comprises providing the first electrode comprising zinc and the second electrode comprising manganese dioxide.

406. The method of any one of Embodiments 397 to 405, wherein providing the first electrode and the second electrode comprises providing at least one of the first electrode and the second electrode comprising at least one of graphite and graphene.

407. The method of any one of Embodiments 397 to 406, further comprising providing at least one of a separator sealing layer between the separator layer and the first electrode and a separator sealing layer between the separator layer and the second electrode.

408. The method of Embodiment 407, wherein providing the separator sealing layer comprises providing the separator sealing layer comprising an electrolyte.

409. The method of any one of Embodiments 397 to 408, further comprising providing at least one of a first current collector electrically coupled to the first electrode and a second current collector electrically coupled to the second electrode.

410. The method of Embodiment 409, wherein providing at least one of the first current collector and the second current collector comprises providing at least one of the first current collector and the second current collector comprising at least one of nickel flakes, graphene flakes, and graphite powder.

411. The method of Embodiment 409 or 410, wherein providing at least one of the first current collector and the second current collector comprises providing at least one of the first current collector and the second current collector comprising carbon nanotubes.

412. The method of any one of Embodiments 409 to 411, wherein at least one of the first electrode, the second electrode, the separator layer, the separator sealing layer, the first current collector and the second current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terephthalate, polyacrylonitrile, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

413. An energy storage device, comprising:
a printed collector layer, wherein the printed current collector layer comprises nickel flakes and a current collector conductive carbon additive; and
a printed electrode layer printed over the current collector layer, wherein the printed electrode layer comprises an ionic liquid and an electrode conductive carbon additive,
wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-1-propylpiperidinium, 1-butyl-2-methylpyridinium, 1-butyl-4-methylpyridinium, and 1-butyl-1-methylpyrrolidinium, and
wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

414. The device of Embodiment 413, wherein the printed electrode layer comprises a printed anode electrode layer and the energy storage device comprises a zinc manganese dioxide battery.

415. The device of Embodiment 413 or 414, wherein the current collector conductive carbon additive comprises graphene.

416. The device of any one of Embodiments 413 to 415, wherein the electrode conductive carbon additive comprises at least one of graphite, graphene, and carbon nanotubes.

417. The device of Embodiment 416, wherein the carbon nanotubes comprises multi-wall carbon nanotubes.

418. The device of any one of Embodiments 413 to 417, wherein the printed current collector layer comprises a polyester component formed in-situ from a polycarboxylic component and a polyol component.

419. The device of Embodiment 418, wherein the polycarboxylic component comprises glutaric acid and the polyol component comprises ethylene glycol.

420. The device of any one of Embodiments 413 to 419, further comprising an electrolyte comprising the ionic liquid.

421. The device of any one of Embodiments 413 to 420, wherein the electrolyte further comprises zinc tetrafluoroborate.

422. A method of fabricating an energy storage device, comprising:
printing a current collector layer over a substrate, wherein the current collector layer comprises nickel flakes and a current collector conductive carbon additive; and
printing an electrode layer over the current collector layer, wherein the electrode layer comprises an ionic liquid and an electrode conductive carbon additive,
wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-1-propylpiperidinium, 1-butyl-2-methylpyridinium, 1-butyl-4-methylpyridinium, and 1-butyl-1-methylpyrrolidinium, and
wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

423. The method of Embodiment 422, wherein the energy storage device comprises a zinc manganese dioxide battery.

424. The method of Embodiment 422 or 423, wherein printing the current collector layer comprises mixing the nickel flakes and the current collector conductive carbon additive with a polycarboxylic acid and a polyol.

425. The method of Embodiment 424, wherein mixing comprises forming a polyester in-situ from the polycarboxylic acid and the polyol.

426. The method of any one of Embodiments 422 to 425, further comprising providing a separator adjacent the electrode layer, wherein the separator comprises at least one of polypropylene, polyethylene, polytetrafluoroethylene, cellulose, and aramid.

427. The method of Embodiment 426, wherein the separator is a non-printed separator.

428. The method of any one of Embodiments 422 to 427, wherein the current collector conductive carbon additive comprises graphene.

429. The method of any one of Embodiments 422 to 428, wherein the electrode conductive carbon additive comprises at least one of graphite, graphene, and carbon nanotubes.

430. The method of any one of Embodiments 422 to 429, wherein the ionic liquid comprises 1-ethyl-3-methylimidazolium tetrafluoroborate ($C_2mimBF_4$).

431. The method of any one of Embodiments 422 to 430, wherein printing the electrode layer comprises printing the electrode layer with the electrode conductive carbon additive at a concentration of about 0.5 weight % to about 5 weight %.

432. The method of Embodiment 431, wherein the electrode layer comprises an anode electrode layer.

433. The method of any one of Embodiments 422 to 432, wherein printing the electrode layer comprises printing the electrode layer with the electrode conductive carbon additive at a concentration of about 1.5 weight % to about 24 weight %.

434. The method of Embodiment 433, wherein the electrode layer comprises a cathode electrode layer.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

The headings provided herein, if any, are for convenience only and do not necessarily affect the scope or meaning of the devices and methods disclosed herein.

What is claimed is:

1. An energy storage device, comprising:
   a printed collector layer, wherein the printed current collector layer comprises nickel flakes and a current collector conductive carbon additive; and
   a printed electrode layer printed over the current collector layer, wherein the printed electrode layer comprises an ionic liquid and an electrode conductive carbon additive,
   wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-1-propylpiperidinium, 1-butyl-2-methylpyridinium, 1-butyl-4-methylpyridinium, and 1-butyl-1-methylpyrrolidinium, and
   wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

2. The device of claim 1, wherein the printed electrode layer comprises a printed anode electrode layer and the energy storage device comprises a zinc manganese dioxide battery.

3. The device of claim 1, wherein the current collector conductive carbon additive comprises graphene.

4. The device of claim 1, wherein the electrode conductive carbon additive comprises at least one of graphite, graphene, and carbon nanotubes.

5. The device of claim 4, wherein the carbon nanotubes comprises multi-wall carbon nanotubes.

6. The device of claim 1, wherein the printed current collector layer comprises a polyester component formed in-situ from a polycarboxylic component and a polyol component.

7. The device of claim 6, wherein the polycarboxylic component comprises glutaric acid and the polyol component comprises ethylene glycol.

8. The device of claim 1, further comprising an electrolyte comprising the ionic liquid.

9. The device of claim 8, wherein the electrolyte further comprises zinc tetrafluoroborate.

10. A method of fabricating an energy storage device, comprising:
    printing a current collector layer over a substrate, wherein the current collector layer comprises nickel flakes and a current collector conductive carbon additive; and
    printing an electrode layer over the current collector layer, wherein the electrode layer comprises an ionic liquid and an electrode conductive carbon additive,
    wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-1-propylpiperidinium, 1-butyl-2-methylpyridinium, 1-butyl-4-methylpyridinium, and 1-butyl-1-methylpyrrolidinium, and wherein the ionic liquid includes an anion selected from the group consisting of tetrafluoroborate, tris(pentafluoroethyl)trifluorophosphate, trifluoromethanesulfonate, hexafluorophosphate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

11. The method of claim 10, wherein the energy storage device comprises a zinc manganese dioxide battery.

12. The method of claim 10, wherein printing the current collector layer comprises mixing the nickel flakes and the current collector conductive carbon additive with a polycarboxylic acid and a polyol.

13. The method of claim 12, wherein mixing comprises forming a polyester in-situ from the polycarboxylic acid and the polyol.

14. The method of claim 10, further comprising providing a separator adjacent the electrode layer, wherein the separator comprises at least one of polypropylene, polyethylene, polytetrafluoroethylene, cellulose, and aramid.

15. The method of claim 14, wherein the separator is a non-printed separator.

16. The method of claim 10, wherein the current collector conductive carbon additive comprises graphene.

17. The method of claim 10, wherein the electrode conductive carbon additive comprises at least one of graphite, graphene, and carbon nanotubes.

18. The method of claim 10, wherein the ionic liquid comprises 1-ethyl-3-methylimidazolium tetrafluoroborate ($C_2mimBF_4$).

19. The method of claim 10, wherein printing the electrode layer comprises printing the electrode layer with the electrode conductive carbon additive at a concentration of 0.5 weight % to 5 weight %.

20. The method of claim 19, wherein the electrode layer comprises an anode electrode layer.

21. The method of claim 10, wherein printing the electrode layer comprises printing the electrode layer with the electrode conductive carbon additive at a concentration of 1.5 weight % to 24 weight %.

22. The method of claim 21, wherein the electrode layer comprises a cathode electrode layer.

* * * * *